United States Patent
Zhang et al.

(10) Patent No.: US 12,085,629 B2
(45) Date of Patent: Sep. 10, 2024

(54) NONLINEAR AND SMART METAMATERIALS USEFUL TO CHANGE RESONANCE FREQUENCIES

(71) Applicant: Trustees of Boston University, Boston, MA (US)

(72) Inventors: Xin Zhang, Medford, MA (US); Stephan Anderson, Cambridge, MA (US); Xiaoguang Zhao, Charlestown, MA (US); Guangwu Duan, Cupertino, CA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 17/545,538

(22) Filed: Dec. 8, 2021

(65) Prior Publication Data

US 2022/0095944 A1 Mar. 31, 2022

Related U.S. Application Data

(63) Continuation of application No. 17/065,812, filed on Oct. 8, 2020, now Pat. No. 11,219,384.
(Continued)

(51) Int. Cl.
*G01R 33/3415* (2006.01)
*G01R 33/12* (2006.01)
*G01R 33/34* (2006.01)

(52) U.S. Cl.
CPC ......... *G01R 33/3415* (2013.01); *G01R 33/12* (2013.01); *G01R 33/34038* (2013.01)

(58) Field of Classification Search
CPC .... A61B 5/055; G01R 33/12; G01R 33/3415; G01R 33/34038
See application file for complete search history.

(56) References Cited

U.S. PATENT DOCUMENTS

| 4,680,549 A | 7/1987 | Tanttu |
| 4,714,886 A | 12/1987 | Halpern |

(Continued)

FOREIGN PATENT DOCUMENTS

| DE | 3500456 A1 | 7/1985 |
| DE | 19751017 A1 | 5/1999 |

(Continued)

OTHER PUBLICATIONS

Ali, H., et al., "Sub-Wavelength Imaging with BC-SRRs Metamaterial Lens for 1.5-T MRI," Applied Magnetic Resonance, vol. 27, pp. 539-554 (2016).

(Continued)

*Primary Examiner* — Dixomara Vargas
(74) *Attorney, Agent, or Firm* — Nutter McClennen & Fish LLP

(57) ABSTRACT

A passive MRI enhancing embodiment includes a plurality of resonators and increases signal-to-noise ratio of radiofrequency signals emitted by a specimen and captured by an MRI machine. The apparatus increases the magnetic field component of radiofrequency energy during signal transmission from the MRI machine to the specimen, and/or reception of signals from the specimen to the MRI machine. Use of the apparatus improves the images generated by the MRI machine, and/or reduces the time necessary for the MRI machine to capture the image. An isolator embodiment has a nonlinear resonator controllably configurable alternately into an isolation configuration and a transmission configuration, and a second resonator. The nonlinear resonator is coupled to a communications port and is substantially communicatively isolated from the second resonator when the nonlinear resonator is in the isolation configuration, and is communicatively coupled to the second resona- (Continued)

tor when the nonlinear resonator is in the transmission configuration.

10 Claims, 28 Drawing Sheets

Related U.S. Application Data

(60) Provisional application No. 62/912,369, filed on Oct. 8, 2019.

(56) References Cited

U.S. PATENT DOCUMENTS

| | | | |
|---|---|---|---|
| 5,243,289 | A | 9/1993 | Blum et al. |
| 5,489,847 | A | 2/1996 | Nabeshima et al. |
| 6,002,311 | A | 12/1999 | Wey et al. |
| 6,157,193 | A | 12/2000 | Renz et al. |
| 7,176,840 | B1 | 2/2007 | Kelley |
| 7,420,371 | B2 | 9/2008 | Zhang |
| 7,800,368 | B2 | 9/2010 | Vaughan et al. |
| 7,800,370 | B2 | 9/2010 | Du et al. |
| 7,945,322 | B2 | 5/2011 | Stevenson et al. |
| 8,159,223 | B2 | 4/2012 | Luekeke et al. |
| 9,678,183 | B2 | 6/2017 | Bulumulla et al. |
| 9,766,192 | B2 | 9/2017 | Derby |
| 10,031,192 | B2 | 7/2018 | Fackelmeier |
| RE47,026 | E | 9/2018 | Vaughan et al. |
| 10,075,025 | B2 | 9/2018 | Ichikawa |
| 10,324,153 | B2 | 6/2019 | Li et al. |
| 10,401,446 | B2 | 9/2019 | Lips |
| 10,761,159 | B2 | 9/2020 | Jones |
| 10,884,089 | B2 | 1/2021 | Zhang et al. |
| 11,219,384 | B2 * | 1/2022 | Zhang ............... G01R 33/36 |
| 2003/0028095 | A1 | 2/2003 | Tulley et al. |
| 2003/0088181 | A1 | 5/2003 | Gleich |
| 2006/0173284 | A1 | 8/2006 | Ackerman et al. |
| 2007/0152668 | A1 * | 7/2007 | Zhang ............... G01R 33/34061 |
| | | | 324/318 |
| 2008/0129298 | A1 * | 6/2008 | Vaughan ............... G01R 33/583 |
| | | | 324/322 |
| 2009/0072825 | A1 | 3/2009 | Prammer et al. |
| 2009/0096456 | A1 | 4/2009 | Biber et al. |
| 2009/0118608 | A1 | 5/2009 | Koay |
| 2009/0128152 | A1 | 5/2009 | Dannels et al. |
| 2009/0140740 | A1 | 6/2009 | Du et al. |
| 2009/0219020 | A1 | 9/2009 | Kurokawa et al. |
| 2009/0302846 | A1 * | 12/2009 | Wong ............... G01R 33/34023 |
| | | | 324/322 |
| 2010/0060509 | A1 | 3/2010 | Chambers et al. |
| 2010/0127707 | A1 | 5/2010 | Lee et al. |
| 2010/0253352 | A1 | 10/2010 | Hulbert |
| 2010/0256481 | A1 | 10/2010 | Mareci et al. |
| 2011/0059716 | A1 | 3/2011 | Cork |
| 2011/0204891 | A1 | 8/2011 | Drake et al. |
| 2011/0309832 | A1 | 12/2011 | Alagappan et al. |
| 2012/0286582 | A1 * | 11/2012 | Kim ............... H02J 50/50 |
| | | | 307/104 |
| 2013/0141096 | A1 | 6/2013 | Bottomley et al. |
| 2013/0179083 | A1 | 7/2013 | Gruber et al. |
| 2013/0251227 | A1 | 9/2013 | Wang et al. |
| 2014/0066753 | A1 | 3/2014 | Qian et al. |
| 2014/0139218 | A1 | 5/2014 | Findeklee et al. |
| 2014/0333144 | A1 | 11/2014 | Ikeuchi et al. |
| 2015/0015259 | A1 | 1/2015 | Duan et al. |
| 2015/0043793 | A1 | 2/2015 | Pagel et al. |
| 2015/0247908 | A1 | 9/2015 | Liu et al. |
| 2015/0302579 | A1 | 10/2015 | Griswold et al. |
| 2015/0323630 | A1 | 11/2015 | Weingartner et al. |
| 2016/0033592 | A1 | 2/2016 | Demir et al. |
| 2016/0047869 | A1 | 2/2016 | Bulumulla et al. |
| 2016/0077182 | A1 | 3/2016 | Wang et al. |
| 2016/0087334 | A1 | 3/2016 | Sayama et al. |
| 2016/0087687 | A1 | 3/2016 | Kesler et al. |
| 2016/0141882 | A1 * | 5/2016 | Ichikawa ............... H04B 5/0037 |
| | | | 307/104 |
| 2016/0169990 | A1 | 6/2016 | Lips |
| 2016/0313419 | A1 | 10/2016 | Vernickel et al. |
| 2017/0045593 | A1 * | 2/2017 | Müller ............... H01P 5/026 |
| 2017/0126063 | A1 | 5/2017 | Pan et al. |
| 2017/0176563 | A1 | 6/2017 | Yablonskiy et al. |
| 2017/0307717 | A1 | 10/2017 | Geraghty et al. |
| 2018/0017647 | A9 | 1/2018 | Yablonskiy et al. |
| 2018/0045795 | A1 | 2/2018 | Bertet et al. |
| 2018/0246047 | A1 | 8/2018 | Miljak et al. |
| 2018/0356483 | A1 * | 12/2018 | Zhang ............... G01R 33/3642 |
| 2019/0004128 | A1 | 1/2019 | Zens |
| 2019/0041476 | A1 | 2/2019 | Otake et al. |
| 2019/0302209 | A1 * | 10/2019 | Zhang ............... G01R 33/3415 |
| 2019/0317164 | A1 * | 10/2019 | Leussler ............... G01R 33/3453 |
| 2021/0100475 | A1 * | 4/2021 | Zhang ............... G01R 33/34038 |

FOREIGN PATENT DOCUMENTS

| | | |
|---|---|---|
| JP | H05-015509 A | 1/1993 |
| JP | 2005533537 A | 11/2005 |
| JP | 2013/210370 A | 10/2013 |
| WO | 2014142772 A2 | 9/2014 |
| WO | 2016011227 A1 | 1/2016 |
| WO | 2017017181 A1 | 2/2017 |
| WO | 2018065745 A1 | 4/2018 |

OTHER PUBLICATIONS

Aydin, K., et al., "Investigation of Magnetic Resonance for Different Split-Ring Resonator Parameters and Designs," New Journal of Physics, vol. 7, Issue No. 168, 15 pages (2005).

By, S., et al., "A 16-Channel Receive, Forced Current Excitation Dual-Transmit Coil for Breast Imaging at 7T," PLOS One, pp. 1-16 (Nov. 2014).

Darnell, A., et al., "Liver Imaging Reporting and Data System with MR Imaging: Evaluation in Nodules 20 mm or Smaller Detected in Cirrhosis at Screening US," Radiology, vol. 275, Issue No. 3, pp. 698-707 (Jun. 2015).

Duan, G., et al., "Boosting magnetic resonance imaging signal-to-noise ratio using magnetic metamaterials," Communication Physics, vol. 2, Issue No. 1, 8 pages (Mar. 2019).

Duke, E., et al., "A Systematic Review and Meta-Analysis of Diagnostic Performance of MRI for Evaluation of Acute Appendicitis," Am. J. Roentgenol., vol. 206, Issue No. 3, pp. 508-517 (Mar. 2016).

European Patent Office, Supplementary European Search Report for Application No. 18813970.3, dated Jan. 29, 2021, 17 pages.

Freire, M., et al., "Experimental demonstration of a μ=-1 metamaterial lens for magnetic resonance imaging," Appl. Phys. Lett., vol. 93, Issue 23, 12 pages (2008).

Freire, M., et al., "On the applications of μ=-1 metamaterial lenses for magnetic resonance imaging," Journal of Magnetic Resonance, vol. 203, Issue No. 1, pp. 81-90 (Mar. 2010).

Hawkes, A.M., et al., "A microwave metamaterial with integrated power harvesting functionality," Applied Physics Letters, vol. 103, Issue No. 16, p. 163901-1-163901-3 (Sep. 2013).

International Search Report and Written Opinion for Application No. PCT/US20/54726, together with Written Opinion of the International Searching Authority, 12 pages (dated Dec. 30, 2020).

Kollia, K., et al., "First Clinical Study on Ultra-High-Field MR Imaging in Patients with Multiple Sclerosis: Comparison of 1.5T and 7T," AJNR Am. J. of Neuroradiology, vol. 30, Issue No. 4, pp. 699-702 (Apr. 2009).

Kratt, K., et al., "3-D Microcoils as a Metamaterial with Electric and Magnetic Response," 2011 16th International Solid-State Sensors, Actuators and Microsystems Conference (Transducers) pp. 2666-2669 (Jun. 2011).

Krauker, D., "Anatomy of a Digital Isolator," Analog Device, Inc., 3 pages (Oct. 2011).

Le Bihan, D., et al., "Diffusion Magnetic Resonance Imaging: What Water Tells US About Biological Tissues," PLOS Biology, vol. 13, Issue No. 7, pp. 1-13 (Jul. 2015).

(56) References Cited

OTHER PUBLICATIONS

Lopez, M., et al., "Nonlinear split-ring metamaterial slabs for magnetic resonance imaging," Applied Physics Letters, 2011, vol. 98, pp. 133508-1-133508-3 (Apr. 2011).
Marques, R., et al., "Left-Handed-Media Simulation and Transmission of EM Waves in Subwavelength Split-Ring-Resonator-Loaded Metallic Waveguides," Physical Review Letters, vol. 89, Issue No. 18, pp. 183901-1-183901-4 (Oct. 2002).
Mazaheri, Y., et al., "Image Artifacts on Prostate Diffusion-weighed Magnetic Resonance Imaging:Trade-offs at 1.5 Tesla and 3.0 Tesla," Academic Radiology, vol. 20, Issue No. 8, pp. 1041-1047 (Aug. 2013).
Nguyen, F., et al., "MR Imaging-based Diagnosis and Classification of Meniscal Tears," RadioGraphics, vol. 34, Issue No. 4, pp. 981-999 (Jul.-Aug. 2014).
Pendry, J.B., et al. "Magnetism from Conductors and Enhanced Nonlinear Phenomena," IEEE Transactions on Microwave Theory and Techniques, vol. 47, Issue No. 11, pp. 2075-2084 (Nov. 1999).
Poutrina, E., et al., "Analysis of nonlinear electromagnetic metamaterials," New Journal of Physics, vol. 12, 27 pages (2010).
Radu, X., et al., "Design of Compact Loop-Wire Medium at Radio Frequencies for Magnetic Resonance Imaging," Antennas and Propagation, EUCAP, First European Conference on IEEE, 5 pages (2006).
Radu, X., et al., "Toward a wire medium endoscope for MRI imaging," Science Direct, Metamaterials, vol. 3, Issue No. 2, pp. 90-99 (Oct. 2009).
Riascos, R., et al., "Imaging of Atlanto-Ocipital and Atlantoaxial Traumatic Injuries: What the Radiologist Needs to Know," RadioGraphics, vol. 35, Issue No. 7, pp. 2121-2134 (Nov.-Dec. 2015).
Robinson, S., et al., "Combining Phase Images from Multi-Channel RF Coils Using 3D Phase Offset Maps Derived From a Dual-Echo Scan," Magnetic Resonance in Medicine, vol. 65, Issue No. 6, pp. 1638-1648 (Jun. 2011).
Saha, S., et al., "A smart switching system to enable automatic tuning and detuning of metamaterial resonators in MRI scans," Scientific Reports, vol. 10, Issue No. 1, 9 pages (2020).
Shadrivov, I.V., et al., "Nonlinear magnetic metamaterials," Optics Express, vol. 16, Issue No. 25, pp. 20266-20271 (Dec. 2008).
Shelby, R.A., et al., "Experimental Verification of a Negative Index of Refaction," Science, vol. 292, Issue No. 5514, pp. 77-79 (Apr. 2001).
Slobozhanyuk, A., et al., "Enhancement of Magnetic Resonance Imaging with Metasurfaces," (with supporting information), Advanced Materials, 22 pages (2016).
Slobozhanyuk, A., et al., "Enhancement of Magnetic Resonance Imaging with Metasurfaces," Physics Med., 6 pages (Jul. 2015).
Slobozhanyuk, A.P, et al., "Enhancement of Magnetic Resonance Imaging with Metasurfaces," Advanced Materials, vol. 28, Issue No. 9, pp. 1832-1838 (Jul. 2015).
Stahl, R., et al., "Assessment of Cartilage-Dedicated Sequences at Ultra-High-Field MRI: Comparison of Imaging Performance and Diagnostic Confidence Between 3.0 and 7.0 T with Respect to Osteoarthritis-Induced Changes at the Knee Joint," SkeletalRadiol., vol. 38, pp. 771-783, 2009.
Syms, R.R.A., et al., "Flexible magnetoinductive ring MRI detector: Design for invariant nearest-neighbour coupling," Science Direct, Metamaterials, vol. 4, Issue No. 1, pp. 1-14 (May 2010).
Tao, H, et al., "Metamaterials on Paper as a Sensing Platform," Advanced Materials, vol. 23, Issue No. 28, pp. 3197-3201 (Jul. 2011).
Tao, H., et al., "MEMS Based Structurally Tunable Metamaterials at Terahertz Frequencies," Journal Infared. Milli. Terhz. Waves, vol. 32, Issue No. 5, pp. 580-595 (May 2011).
Tao, H., et al., "Microwave and Terahertz wave sensing with metamaterials," Optics Express, vol. 19, Issue No. 22, pp. 21620-21626 (Oct. 2011).
Tolouee, A., et al., "Compressed Sensing Reconstruction of Cardiac Cine MRI Using Golden Angle Spiral Trajectories," Journal of Magnetic Resonance, vol. 260, pp. 10-19, Nov. 2015.
Turpin, J., et al., "Reconfigurable and Tunable Metamaterials: A Review of the Theory and Applications," International Journal of Antennas and Propagation, vol. 11, Issue No. 4, 19 pages (Jan. 2014).
Veselago, V.G., "The Electrodynamics of Substances with Simultaneously Negative Values of € and µ," Soviet Physics Uspekhi, vol. 10, Issue No. 4, pp. 509-514 (Jan.-Feb. 1968).
Wang B., "Nonlinear properties of split-ring resonators," Optics Express, vol. 16, Issue No. 20, pp. 16058-16063 (Sep. 2008).
Weintraub, M., et al., "Biologic Effects of 3 Tesla (T) MR Imaging Comparing Traditional 1.5 T and 0.6 T in 1023 Consecutive Outpatients," American Society of Neuroimaging, vol. 17, Issue No. 3, pp. 241-245 (Jul. 2007).
Wiltshire, M.C.K., et al., "Microstructured Magnetic Materials for Radio Frequency Operation in Magnetic Resonance Imaging (MRI)," MRI Paper Final, 10 pages, filed on Dec. 10, 2000.
Wiltshire, M.C.K., et al., "Microstructured Magnetic Materials for RF Flux Guides in Magnetic Resonance Imaging," Science, vol. 291, Issue No. 5505, pp. 849-851 (Feb. 2001).
Zhao, X., et al., "Intelligent Metamaterials Based on Nonlinearity for Magnetic Resonance Imaging," Advanced Materials, vol. 31, Issue No. 49, pp. 1905461-1-1905461-7 (Oct. 2019).
Zhao, X., et al., "Optically tunable metamaterial perfect absorber on highly flexible substrate," Sensors and Actuators A: Physical, vol. 231, pp. 74-80 (Jul. 2015).
Canadian Patent Office, Office Action dated Jan. 27, 2023, 4 pages.
International Search Report and Written Opinion for Application No. PCT/US20/54726, of the International Searching Authority, 12 pages (dated Dec. 30, 2020).
Japan Patent Office, Notice of Reasons for Refusal for Japanese Patent Application No. 2022-521127 dated Apr. 26, 2024, with English Translation (6 pages).

\* cited by examiner

Signal Strength (Mean)

| 1 | 2 | 3 | 4 | |
|---|---|---|---|---|
| 157.2 | 173.2 | 178.5 | 178.1 | |
| 5 | 6 | 7 | 8 | 9 |
| 158.5 | 166.3 | 172.3 | 151.3 | 184.8 |

Noise Level (StdDev)

| 10 | 11 | 12 | Avrg |
|---|---|---|---|
| 4.4 | 4.6 | 5.2 | 4.7 |

SNR

| 1 | 2 | 3 | 4 | |
|---|---|---|---|---|
| 33.2 | 36.6 | 37.7 | 37.6 | |
| 5 | 6 | 7 | 8 | 9 |
| 33.5 | 35.1 | 36.4 | 32.0 | 39.0 |

Signal Strength (Mean):

| 1 | 2 | 3 | 4 | |
|---|---|---|---|---|
| 1174 | 640.4 | 546.6 | 481.1 | |
| 5 | 6 | 7 | 8 | 9 |
| 193.1 | 404.5 | 428.6 | 267.6 | 289.7 |

Noise level (StdDev):

| 10 | 11 | 12 | Avrg |
|---|---|---|---|
| 4.1 | 4.7 | 3.9 | 4.2 |

SNR

| 1 | 2 | 3 | 4 | |
|---|---|---|---|---|
| 277.3 | 151.3 | 129.1 | 113.6 | |
| 5 | 6 | 7 | 8 | 9 |
| 45.6 | 95.5 | 101.2 | 63.2 | 68.4 |

Signal Strength (Mean):

| 1 | 2 | 3 | 4 |
|---|---|---|---|
| 1258.0 | 605.9 | 498.2 | 381.7 |
| 5 | 6 | 7 | 8 | 9 |
| 95.9 | 363.6 | 343.1 | 156.6 | 144.9 |

Noise level (StdDev):

| 10 | 11 | 12 | Avrg |
|---|---|---|---|
| 2.7 | 3.5 | 3.2 | 3.1 |

SNR

| 1 | 2 | 3 | 4 |
|---|---|---|---|
| 401.5 | 193.4 | 159.0 | 121.8 |
| 5 | 6 | 7 | 8 | 9 |
| 30.6 | 116.0 | 109.5 | 50.0 | 46.2 |

39 MHz  55 MHz  63 MHz

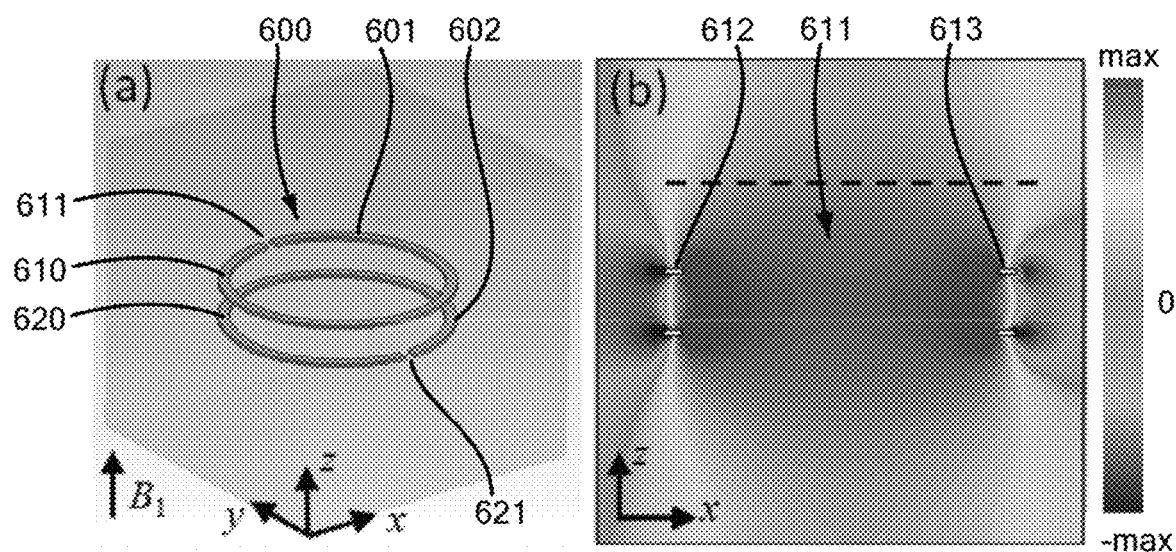
Fig. 6A  Fig. 6B
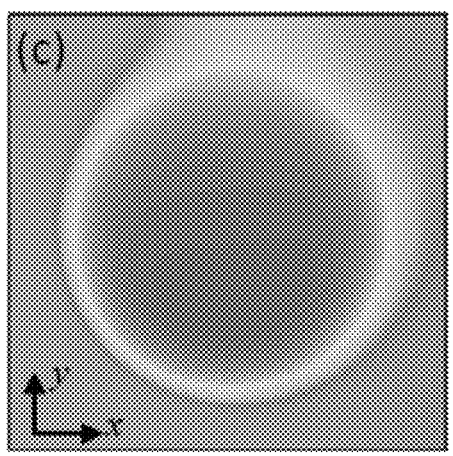
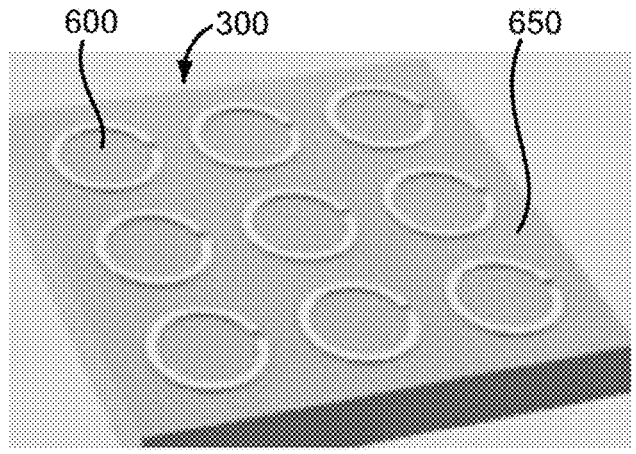
Fig. 6C  Fig. 6E
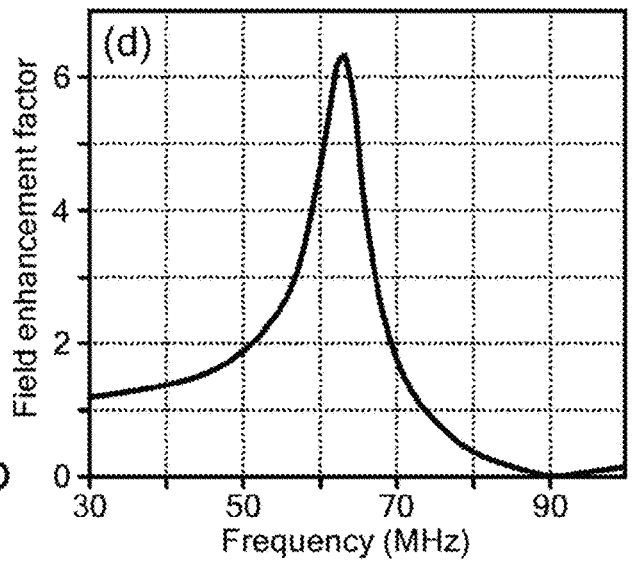
Fig. 6D (a)

(b)

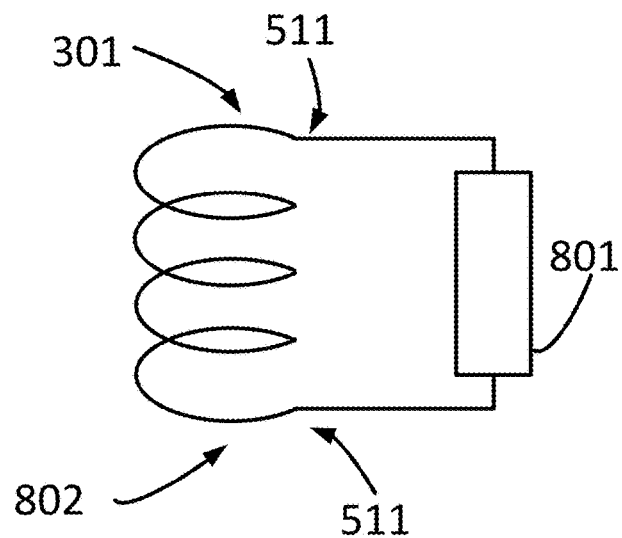
Fig. 8A
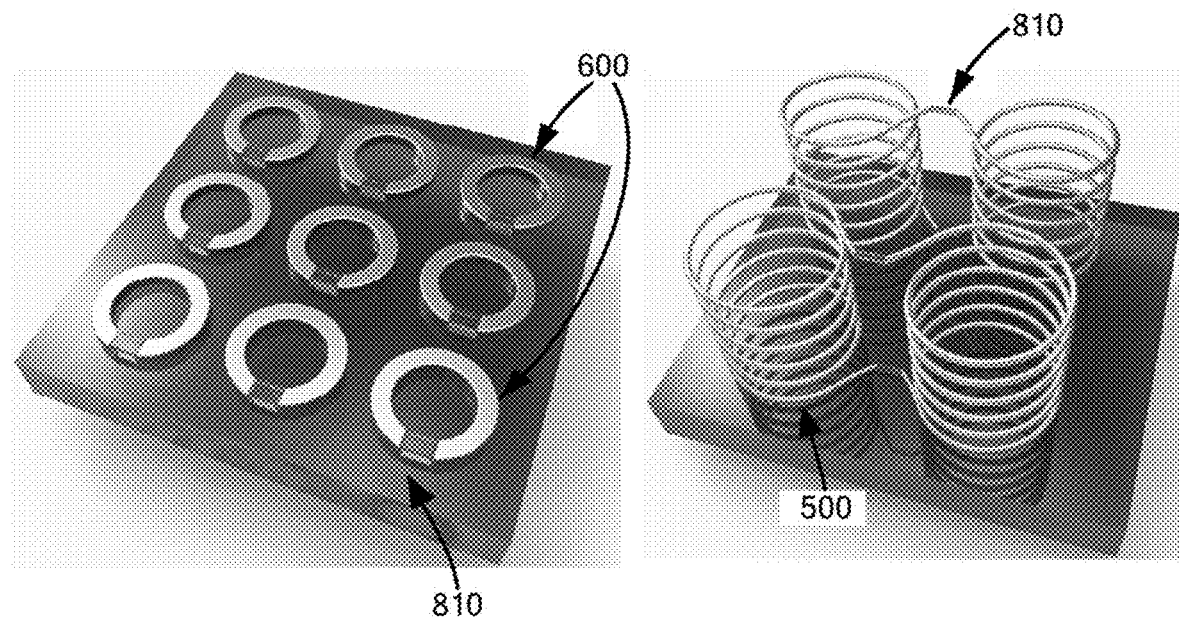
Fig. 8B
Fig. 8C

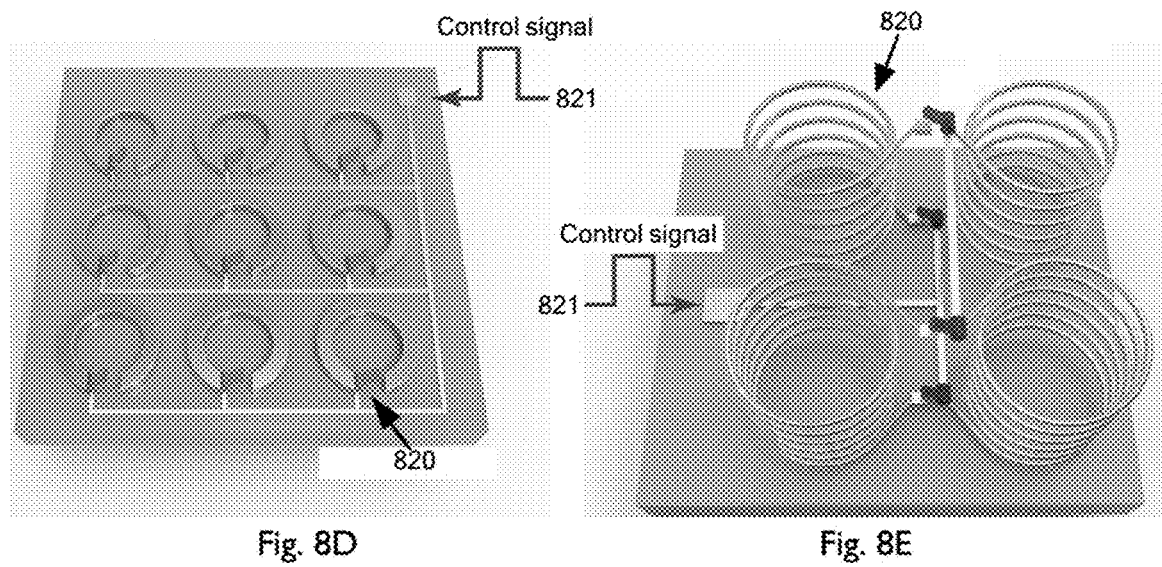
Fig. 8D  Fig. 8E
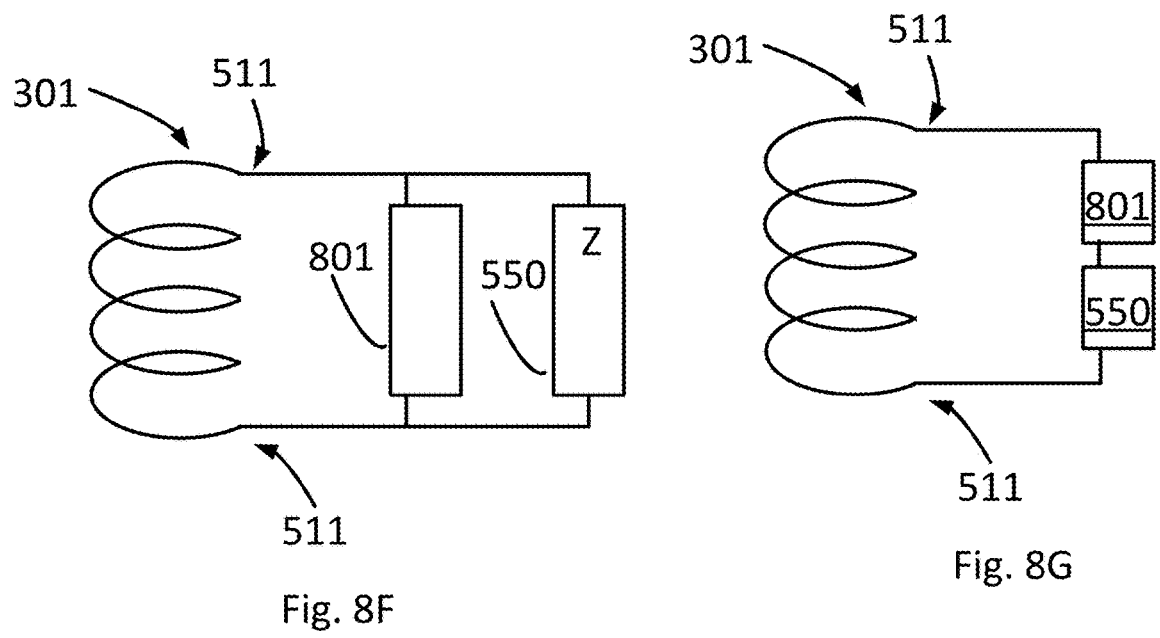
Fig. 8F
Fig. 8G

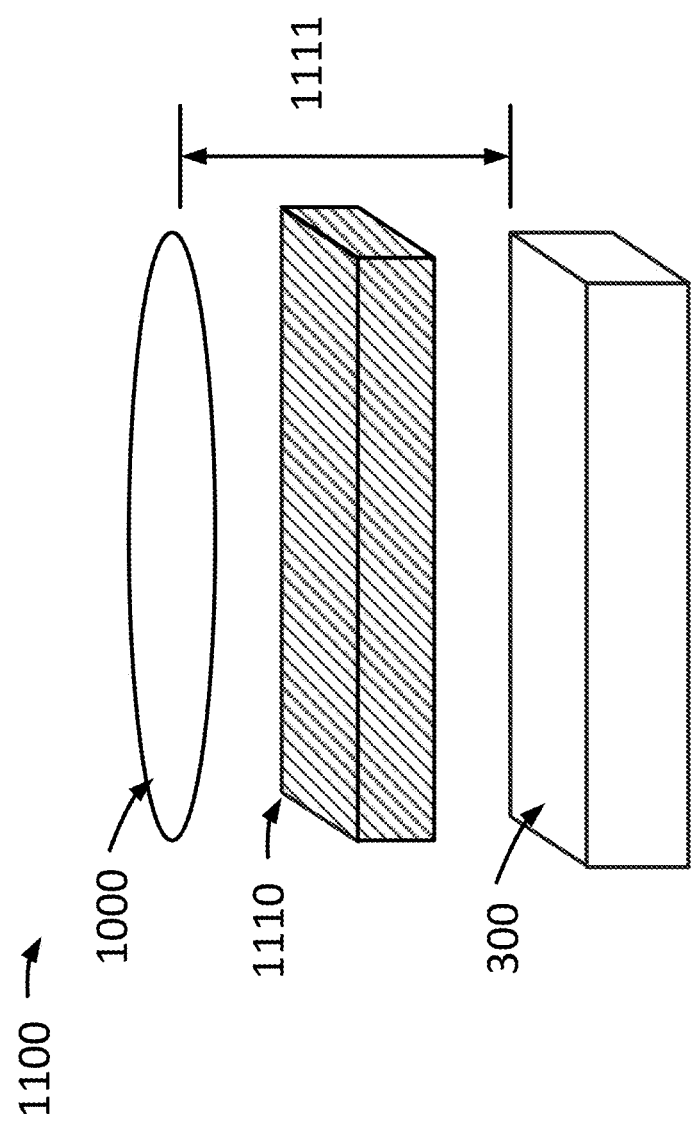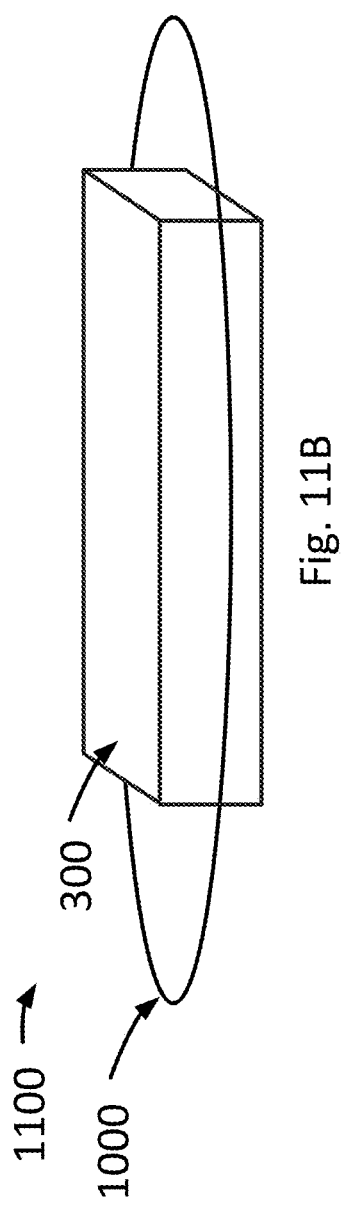

Helix array

NONLINEAR AND SMART METAMATERIALS USEFUL TO CHANGE RESONANCE FREQUENCIES

RELATED APPLICATIONS

This patent application is a continuation application of U.S. non-provisional patent application Ser. No. 17/065,812 filed Oct. 8, 2020, entitled "Nonlinear and Smart Metamaterials Useful to Change Resonance Frequencies," and naming Xin Zhang, Stephan Anderson, Xiaoguang Zhao, and Guangwu Duan as inventors, and claims priority to U.S. provisional patent application No. 62/912,369 filed Oct. 8, 2019 and entitled "Nonlinear and Smart Metamaterials Useful to Change Resonance Frequencies," and naming Xin Zhang, Stephan Anderson, Xiaoguang Zhao, and Guangwu Duan as inventors; and is also is related to U.S. non-provisional patent application Ser. No. 16/443,126 filed Jun. 17, 2019 entitled, "Apparatus for Improving Magnetic Resonance Imaging," and naming Xin Zhang, Stephan Anderson, Guangwu Duan, and Xiaoguang Zhao as inventors [practitioner's file 32730-12503], which is a continuation of U.S. non-provisional patent application Ser. No. 16/002,458, filed Jun. 7, 2018, entitled, "Apparatus for Improving Magnetic Resonance Imaging," and naming Xin Zhang, Stephan Anderson, Guangwu Duan, and Xiaoguang Zhao as inventors, now U.S. Pat. No. 10,324,152 [practitioner's file 32730-12501], which claims priority to provisional U.S. patent application No. 62/516,376, filed Jun. 7, 2017, entitled, "Apparatus for Improving Magnetic Resonance Imaging," and naming Xin Zhang, Stephan Anderson, Guangwu Duan, and Xiaoguang Zhao as inventors [practitioner's file 32730-11901], the disclosure of each of the foregoing is incorporated herein, in its entirety, by reference.

GOVERNMENT SUPPORT

This invention was made with Government Support under Contract No. EB024673 awarded by the National Institutes of Health. The Government has certain rights in the invention.

TECHNICAL FIELD

The present invention relates to resonating circuits, more particularly to circuits with controllable resonant frequencies.

BACKGROUND ART

Magnetic resonance imaging ("MRI") is a medical imaging technique that captures an image of a specimen's internal structures without the use of X-rays. An MRI machine applies a strong magnetic field and electromagnetic stimulus to the specimen, causing atoms of the specimen to emit electromagnetic signals in response. The MRI machine captures the electromagnetic signals emitted by the specimen and from those captured signals constructs the image.

A known limitation of MRI machines is the signal-to-noise ratio (SNR) of the captured signals. Noise is generated by a variety of sources, including the circuitry of the MRI machine itself, and corrupts and obscures the signals emitted by the specimen. SNR may be improved by either boosting the signal, for example by increasing the strength of the static magnetic field, or by reducing the noise, for example by improving the MRI machine's signal processing circuitry, or by a combination of both. Such approaches are less than ideal, however, there are limits to the amount of power that can be safely applied to some specimens, such as a living animal, and noise cannot be completely eliminated.

SUMMARY OF VARIOUS EMBODIMENTS

Illustrative embodiments disclose a signal magnifying accessory for use within a bore of an MRI machine. The MRI machine has a transmitting coil disposed to transmit, to a specimen in the bore, an excitation signal having a transmission frequency in a transmitting mode, and reception coil disposed to receive, from the specimen, a response signal having a response frequency in a receiving mode.

In a first embodiment, the accessory includes a resonator array having a plurality of metamaterial resonators, each of the metamaterial resonators having a resonant frequency, the metamaterial resonators disposed to inductively couple to one another in response to an applied electromagnetic signal. Illustrative embodiments of the array include at least two metamaterial resonators, but may include more than two metamaterial resonators, such as a N×M array of such resonators, where N and M are integers (e.g., 2, 3, 4, 5, 6, 7, 8).

The accessory also includes a non-linear control resonator having (a) a resonator coil; and (b) a controllable impedance coupled to the resonator coil. The control resonator has a first resonant frequency when the controllable impedance is in a first impedance state, and a second resonant frequency when the controllable impedance is in a second impedance state.

The resonator coil and the controllable impedance selected so that the control resonator is configured (i) to produce, in concert with the resonator array when the MRI machine is in the transmitting mode, a first array resonant frequency offset from the transmission frequency; and (ii) to produce, in concert with the resonator array when the MRI machine is in a receiving mode, a second array resonant frequency equal to the response frequency, so as to magnify the response signal.

Illustrative embodiments also include a spacer layer disposed between the array of resonators and the non-linear resonator, the spacer layer defining a gap (d) between the array of resonators and the non-linear resonator.

In some embodiments, the resonator coil has a first end and a second end, and the controllable impedance is electrically coupled between the first end and the second end. For example, in some embodiments, the controllable impedance is a varactor diode, the varactor diode configured to assume the first impedance state in response to receipt by the varactor diode of the excitation signal from the MRI machine when the MRI machine is in the transmitting mode. As another example, in some embodiments, the resonator coil includes a split ring resonator, and the controllable impedance is or includes a varactor, the varactor configured to assume a first capacitance in response to receipt of a radiofrequency excitation signal from the MRI machine in a transmission mode, and to assume a second capacitance when the MRI machine is in a reception mode. In some such embodiments, the varactor diode is configured to assume the second impedance state in the absence of the excitation signal from the MRI machine when the MRI machine is in the receiving mode.

The resonator array in illustrative embodiments defines a resonator plane, and the control resonator is disposed substantially parallel to the resonator plane at a non-zero distance (d) from the resonator plane. For example, in some embodiments, the control resonator is disposed substantially parallel to the resonator plane a distance (d) of 2 centimeters from the resonator plane. In other embodiments, the control resonator is disposed substantially parallel to the resonator plane a distance (d) of zero centimeters from the resonator plane. In such embodiments, the control resonator surrounds the resonator array.

Some embodiments further include a spacer apparatus disposed in the spacer layer between the resonator array and the control resonator. The spacer apparatus is, in preferred embodiments, a non-metal and non-magnetic solid material. The spacer apparatus holds the control resonator at a defined distance from the array.

Another embodiment discloses a method of amplifying a response signal from a specimen in the bore of an MRI machine.

The method includes providing, in the bore of the MRI machine having a working frequency, a controllable array assembly, for example such as the controllable array assemblies described above. In some embodiments, controllable array assembly includes (a) a resonator array including a plurality of metamaterial resonators configured to inductively couple to one another at the operating frequency of the MRI machine; and (b) a nonlinear control resonator having a controllable impedance.

The method includes configuring the controllable array assembly into a passthrough mode when the MRI machine is in a transmitting mode; and configuring the controllable array assembly into an amplifying mode when the MRI machine is in a receiving mode.

In some embodiments, configuring the controllable array assembly into a passthrough mode includes automatically configuring the nonlinear control resonator into a first resonance mode, wherein the nonlinear control resonator in the first resonator mode couples with the resonator array to produce, in the controllable array assembly, an assembly resonant frequency offset from the working frequency of the MRI machine. In some such embodiments, automatically configuring the nonlinear control resonator into a first resonance mode includes providing, to the controllable impedance, a radiofrequency excitation signal transmitted from the MRI machine.

In some embodiments, configuring the controllable array assembly into an amplifying mode includes automatically configuring the nonlinear control resonator into a second resonance mode, wherein the nonlinear control resonator in the second resonator mode couples with the resonator array to produce, in the controllable array assembly, an assembly resonant frequency at the working frequency of the MRI machine. In some such embodiments, automatically configuring the nonlinear control resonator into the second resonance mode includes withholding, from the controllable impedance, an excitation signal transmitted from the MRI machine.

Yet other embodiments provide isolator circuits.

In one embodiment, such a circuit includes a first resonator having a characteristic resonant frequency; and a non-linear resonator controllably configurable into a first resonance state in which the non-linear resonator has a first resonant frequency equal to the characteristic resonant frequency, and a second resonance state in which the non-linear resonator has a second resonant frequency distinct from the first resonant frequency.

In some such embodiments, the first resonator is configured to couple to a first port and the non-linear resonator is configured to couple to a second port, and wherein in the first resonance state, the non-linear resonator is configured to inductively couple to the first resonator so as to communicatively couple a signal from the first resonator to the second port, and in the second resonance state, the non-linear resonator is configured to isolate the second port from the first resonator.

To that end, the non-linear resonator in some embodiments includes a metamaterial resonator having a first end and a second end, and a coupler electrically disposed between the first end and the second end, wherein the coupler is controllably configurable into a plurality of impedance states, including: a first impedance state, which first impedance state configures the non-linear resonator into the first resonance state, and a second impedance state, which second impedance state configures the non-linear resonator into the second resonance state.

In some such embodiments, the metamaterial resonator includes a split-ring resonator.

In some embodiments, the coupler includes a varactor, the varactor configured: (a) to have the second impedance state in response to a radio-frequency signal incident on the coupler from the second port, such that the non-linear resonator is in the second resonant state and the second port is isolated from the first resonator, and (b) to have the first impedance state in the absence of such radio-frequency signal at the carrier frequency from the second port, such that the non-linear resonator is in the first resonant state and is configured to communicatively couple the first resonator to the second port.

In other embodiments, the coupler includes a varactor configured: (a) to have the first impedance state in response to a radio-frequency signal incident on the coupler from the second port, such that the non-linear resonator is in the first resonant state and is configured to communicatively couple the second port to the first resonator, and (b) to have the second impedance state in the absence of such radio-frequency signal at the carrier frequency from the second port, such that the non-linear resonator is in the second resonant state and the second port is isolated from the first resonator.

In other embodiments, the coupler includes a switch, which may be, for example, a transistor or a MEMS switch.

As for the linear resonator, in some embodiments, the first resonator is a linear resonator, such as a helix resonator for example.

Another embodiments provides a method that includes providing a nonlinear resonator and a second resonator, wherein: the nonlinear resonator is controllably configurable into an isolation configuration having an isolation mode resonant frequency, and a reception configuration having a reception mode resonant frequency distinct from the isolation mode resonant frequency, and wherein the second resonator has a second resonant frequency equal to the reception mode resonant frequency; and in a first mode, configuring the nonlinear resonator into the isolation configuration, such that the nonlinear resonator is substantially communicatively isolated from the second resonator.

Some such methods also include, in a second mode, configuring the nonlinear resonator in the reception configuration such that the nonlinear resonator is configured for resonant communication with the second resonator.

Moreover, in some embodiments, the method also includes, after configuring the nonlinear resonator in the reception configuration, providing a signal to the second resonator; and receiving the signal at the nonlinear resonator.

In some embodiments, the method also includes, after receiving the signal at the nonlinear resonator, configuring the nonlinear resonator into the isolation configuration so as to isolate the nonlinear resonator from a signal on the second resonator, and to isolate the second resonator from another signal on the nonlinear resonator. In some such embodiments, resonant coupling between the second resonator and the nonlinear isolator in the isolation configuration is at least 9 dB less than resonant coupling between the second resonator and the nonlinear isolator in the reception configuration.

Another embodiment provides a circuit that includes a first resonating means for resonating in response to an applied electromagnetic signal, the first resonating means having a characteristic resonant frequency; and a non-linear resonating means for selectively communicating in resonance with the first resonating means, the non-linear resonating means configurable into a first resonance state having a first resonant frequency equal to the characteristic resonant frequency, and a second resonance state having a second resonant frequency distinct from the first resonant frequency.

In some embodiments, when the non-linear resonating means is in the second resonance state, the non-linear resonating means is substantially communicatively isolated from the first resonating means.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing features of embodiments will be more readily understood by reference to the following detailed description, taken with reference to the accompanying drawings, in which:

FIGS. 6A, 6B, 6C, 6D and 6E schematically illustrate an embodiment of, and some characteristics of, a broadside-coupled split ring resonator;

FIGS. 8A, 8B, 8C, 8D, 8E, 8F and 8G schematically illustrate embodiments of tunable unit cells;

FIG. 11A schematically illustrates an embodiment of a controllable array assembly;

FIG. 11B schematically illustrates another embodiment of a controllable array assembly;

DETAILED DESCRIPTION OF SPECIFIC EMBODIMENTS

An apparatus having a plurality of resonators increases signal-to-noise ratio of radiofrequency ("RF") signals emitted by a specimen and captured by an MRI machine, and does so without increasing the power transmitted by the MRI machine. In some embodiments, the apparatus increases the magnetic field component of radiofrequency energy during both signal transmission of radiofrequency energy from the MRI machine to the specimen, and transmission of radiofrequency signals from the specimen to the MRI machine, while in other embodiments, the apparatus increases the magnetic field component of radiofrequency energy only during transmission of radiofrequency signals from the specimen to the MRI machine, and not during transmission of radiofrequency energy from the MRI machine to the specimen. Moreover, the apparatus enhances specimen safety by substantially avoiding unwanted generation or, or increase in, an electric field. Use of the apparatus improves the images generated by the MRI machine, and/or reduces the time necessary for the MRI machine to capture the image.

Definitions

The term "transmission mode" in connection with an MRI machine means a mode in which the MRI machine provides an excitation signal to a specimen in the bore of the MRI machine.

The term "reception mode" (or "receiving" mode) in connection with an MRI machine means a mode in which the MRI machine receives a response signal from a specimen in the bore of the MRI machine.

The term "excitation signal" in connection with an MRI machine means a signal provided by the MRI machine to a specimen in the bore of the MRI machine in order to elicit, from the specimen, a response signal.

The term "response signal" (or "specimen response signal") in connection with an MRI machine means a signal generated, in response to an excitation signal, by a specimen in the bore of the MRI machine.

Figure 1A:
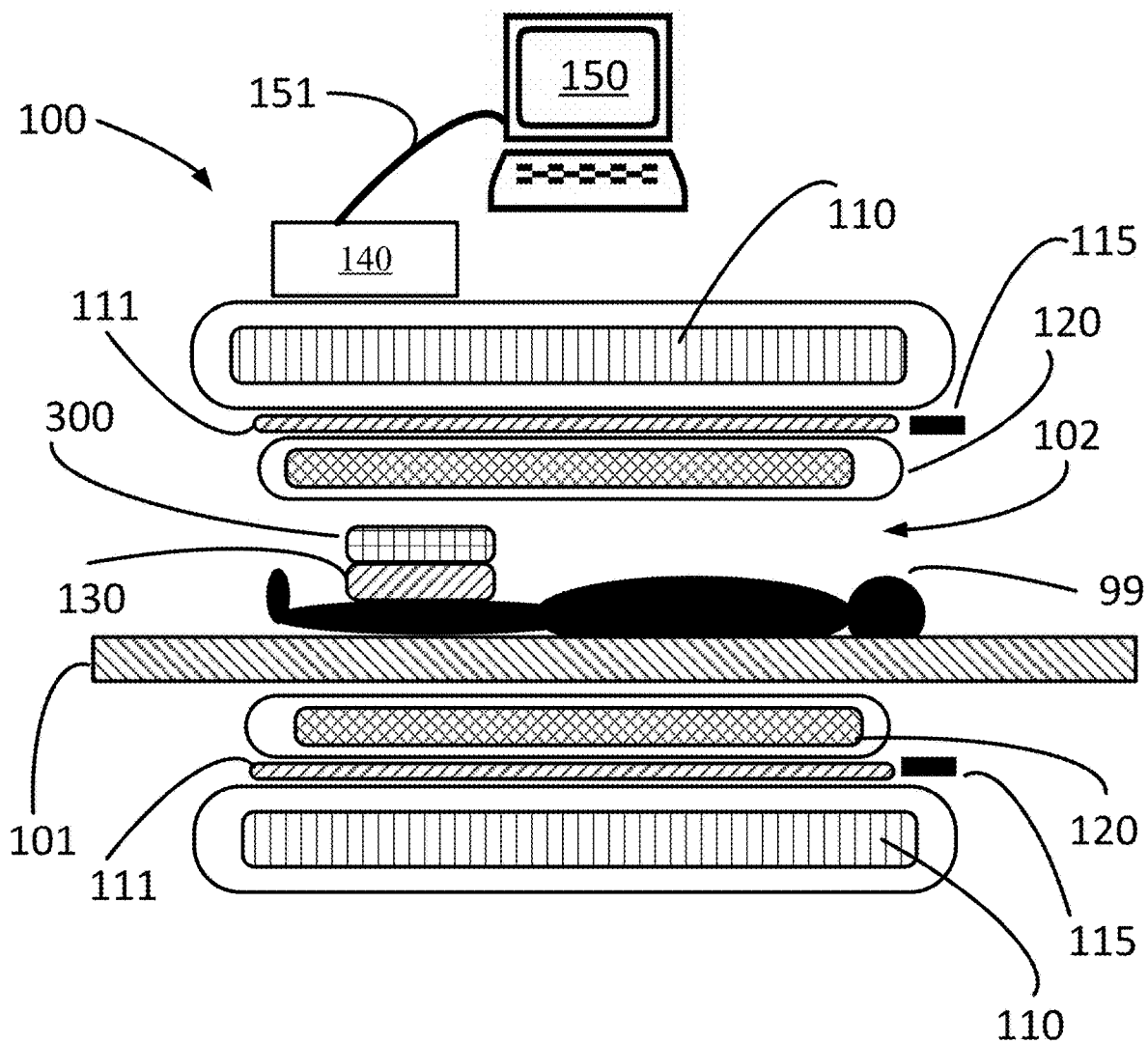
FIGS. 1A, 1B, 1C and 1D schematically illustrate an embodiment of an MRI machine.

FIG. 1A schematically illustrates an MRI machine 100 in cross-section, and shows several well-known features of such machines. A specimen 99 being scanned by the MRI machine lays on a table 101. Typically, the specimen 99 must lay as still as possible for the duration of the scan, which can be 30 minutes or more.

MRI machines include a "main" magnet 110 that produces a magnetic field (which may be referred-to as a "main" magnetic field) around and through the specimen 99. In illustrative embodiments, the main magnetic field is a static and uniform magnetic field. In some MRI machines 100, the main magnet 100 is a permanent magnet. In other MRI machines 100, the main magnet includes main field coils 110 that produce a magnetic field around and through the specimen 99. Some MRI machines 100 also include one or more or shim coils 111 for correcting shifts in the homogeneity of the main magnetic field produced by the main field coils 110. Some MRI machines 100 also include one or more gradient coils 115 that create a variable magnetic field that is in addition to the magnetic field produced by main field coils 110, and which are used to localize the region to be scanned.

The MRI machine 100 has one or more systems (which may be referred to, generally, as "RF coils" or "radiofrequency coils") to transmit radiofrequency excitation signals to a specimen 99, and to receive MR signals (e.g., specimen response signals) produced by the specimen 99 in response to an excitation signal. Some RF coils may be referred-to as "birdcage" coils. Historically, MRI machines included coils that each had both transmit and receive capabilities. Some MRI machines, however, include a system (e.g., a set of one or more coils) for transmitting radiofrequency signals to a specimen 99, and a separate system (e.g., a set of one or more coils) to receive MR signals produced by the specimen 99. Illustrative embodiments described below include body coils 120 that perform both transmit radiofrequency signals to a specimen 99, and receive MR signals produced by the specimen 99. Some embodiments include transmit coils to transmit excitation signals to the specimen 99, and receive coils separate from the transmit coils to receive response signals from the specimen 99. Some examples of RF coils as components of MRI machines are found in U.S. patent application publication no. US 2019/0041476 A1 to Otake et al., and in U.S. patent application publication no. US 2009/0096456 to Biber et al.

In a transmission mode, body coils 120 transmit a radiofrequency signal, and thereby subject the specimen 99 to electromagnetic (e.g., radio frequency) stimulus. Consequently, when referred-to in their capacity as transmitters, body coils 120 may be referred to as "transmit" coils, "transmitter" coils or "drive" coils).

In response, atoms of the specimen emit electromagnetic pulses (or "MR" signals) that may be detected by the body coils 120 (in a reception mode), and/or specimen coils 130. Specimen coils 130 (which may sometimes be referred-to as "surface" coils) may be preferred in some situations because they can be disposed closer to the specimen 99, and may produce signals with greater signal-to-noise ratio ("SNR") than the signals produced by the more remote body coils 120.

A computer 150 is in data communication with the MRI machine 100, such as by communications link 151, and receives and processes the signals received by the body coils 120, and/or specimen coils 130, to produce an image of internal structures of the specimen. The body coils 120 and specimen coils 130 are wired to the MRI machine 100. The body coils 120 are in power communication and control communication with the MRI machine 100 to receive power and control signals required to produce the electromagnetic stimulus. Both the body coils 120 and specimen coils 130 are in data communication with the MRI machine 100 to provide to the MRI machine 100 the signals they detect from the specimen 99. To that end, some embodiments of an MRI machine include a controller 140 configured to provide control signals to the MRI machine, and/or to an array as described below in connection with control signal 821, and/or to receive signals from the body coils 120 and specimen coils 130.

The quality of the image, and the time needed for the MRI machine 100 to collect a sufficient number of emitted signals to produce the image, depend in part on the signal-to-noise ratio ("SNR") of the signals received. As known in the art signal-to-noise ratio is the ratio of the signals emitted by the specimen 99 in response to excitation of the specimen 99 by the MRI machine 100. Signal-to-noise ratio is a dimensionless ratio of signal power (e.g., power in the signal emitted by the specimen 99, which may be referred-to as "signal power" or "$P_S$") to the power of noise in a signal received by the MRI machine which may be referred-to as "noise power" or "$P_N$"). Signal-to-noise ratio is typically written as SNR=$P_S/P_N$. Signal-to-noise ratio may be expressed in decibels (dB) according to the formula: SNR(dB)=10 $\log_{10}$ $P_S/P_N$, but does not have to be expressed in decibels.

An increase in the SNR may improve the MRI's output and/or reduce the time required to collect signals emitted by the specimen 99.

Figure 1B:
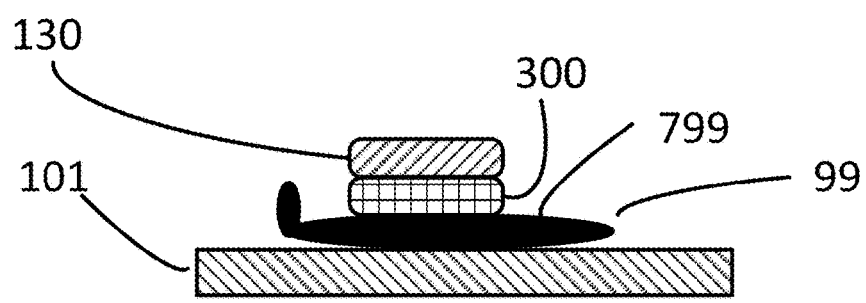

FIG. 1A and FIG. 1B each schematically illustrates an embodiment of a resonator array 300 for improving the operation of, and results produced by, an MRI machine. In use, the resonator array 300 is disposed between the specimen 99 and the main field 110 and the body coils 120 and the shim coils 111 and the gradient coils 115. In illustrative embodiments, in use, the resonator array 300 is disposed radially outward of the specimen 99, and radially inward of the main field 110 and the body coils 120 and the shim coils 111 and the gradient coils 115.

In FIG. 1A, specimen coils 130 are placed between the specimen 99 and the resonator array 300, and in FIG. 1B, the resonator array 300 is disposed between the specimen 99 (in this illustration, a limb or appendage 799 of specimen 99) and the specimen coils 130. In some embodiments, the resonator array 300 may be positioned in the bore 102 of the MRI machine without specimen coils 130, for example when the MRI machine 100 uses body coils 120 to receive electromagnetic pulses emitted by the specimen 99. As used herein, the term "bore" 102 of an MRI machine 100 means the place in which the specimen 99 is disposed when being imaged by the MRI machine 100. For example, in a closed MRI machine 100, the bore 102 is the interior of the machine's toroid section; in an open MRI machine 100, the bore 102 is the space between the machine's top and bottom magnetic areas; and in an open upright MRI machine 100, the bore 102 is the space between the machines left and right magnetic areas. In illustrative embodiments, the bore 102 of an MRI machine 100 is defined by components of the MRI machine 100. For example, in illustrative embodiments, components of the MRI machine 100 [e.g., magnet 110 (including, without limitation main field coils 110), shim coils 111, gradient coils 115, body coils 120, although specimen coils 130 (if present) may be disposed within the bore 102)].

Figure 1C:
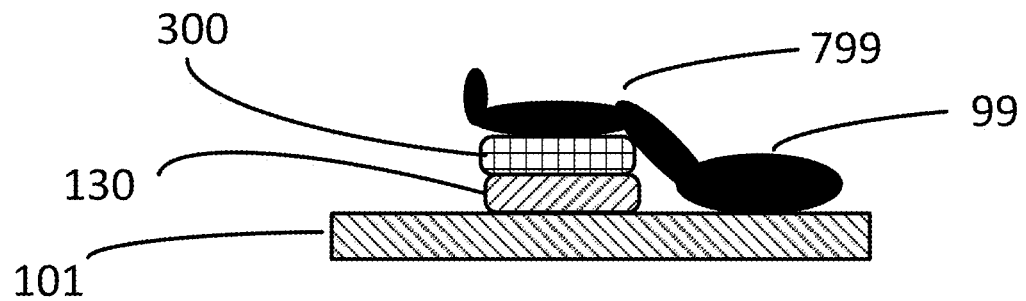
Figure 1D:
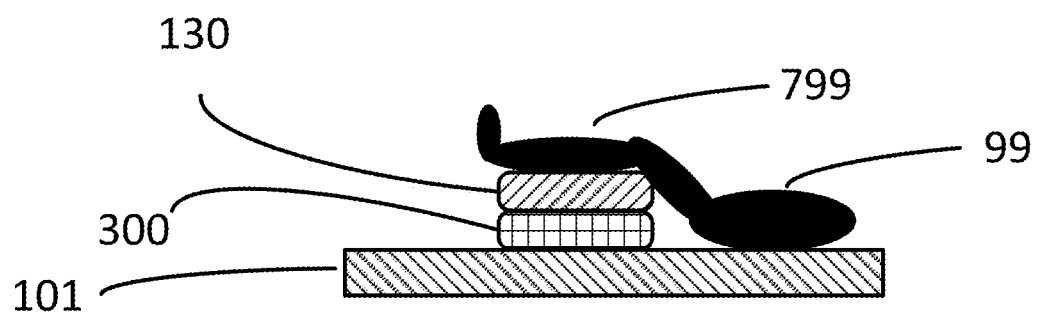

Although FIG. 1A and FIG. 1B illustrate the specimen 99 between the specimen coils 130 and resonator array 300 and the table, that is not a limitation on the use of the resonator array 300, which may be placed, with or without specimen coils 130, between the specimen 99 and the table 101, as schematically illustrated in FIG. 1C and FIG. 1D.

In contrast to the body coils 120, the resonator array 300 is passive in that it does not require or receive power signals, and in some embodiments does not require or receive control signals, in order to perform its function. As can be understood from the figures and text, illustrative embodiments of the resonator array 300 are capable of passive operation, for example to increase signal-to-noise ratio of signals emitted by the specimen. In illustrative embodiments, the resonator array 300 (including its unit cells 301) is separate from, not part of, the MRI machine 100. In other words, in illustrative embodiments, the resonator array 300 is in addition to the components of the MRI machine 100 [e.g., in addition to: magnet 110 (including, without limitation, main field coils 110), shim coils 111, gradient coils 115, body coils 120, and (if present) specimen coils 130].

Moreover, in illustrative embodiments, the resonator array 300 (including its unit cells 301) is physically separate from the MRI machine 100 (e.g., body coils 120 or specimen coils 130, main field coils 110, shim coils 111 and gradient coils 115), and is not wired to MRI machine 100 (e.g., body coils 120 or specimen coils 130, main field coils 110, shim coils 111 and gradient coils 115). Also, in contrast to both the body coils 120 and the specimen coils 130, the resonator array 300 is not in data communication with the MRI machine 100.

The inventors have discovered that use of a resonator array 300 as schematically illustrated in FIG. 1A-FIG. 1D, with or without a specimen coil 130, improves the SNR of radiofrequency signals transmitted from the MRI machine 100 to the specimen 99, and improves the SNR of signals emitted by the specimen 99 and received by the MRI machine 100, and can increase the quality of the MRI's output image, and/or reduce the time required to scan a specimen 99, each of which represents an improvement over existing MRI technologies. Due to its unusual properties, the resonator array 300, and/or its resonators 301, may be thought of as a metamaterial. However, that does not require that the resonator array 300, and/or its unit cells 301, have a negative index of refraction, negative permittivity, and/or negative permeability. In various embodiments, the resonator array 300, and/or its unit cells 301, may have a positive index of refraction, positive permittivity, and/or positive permeability.

Figure 2A:
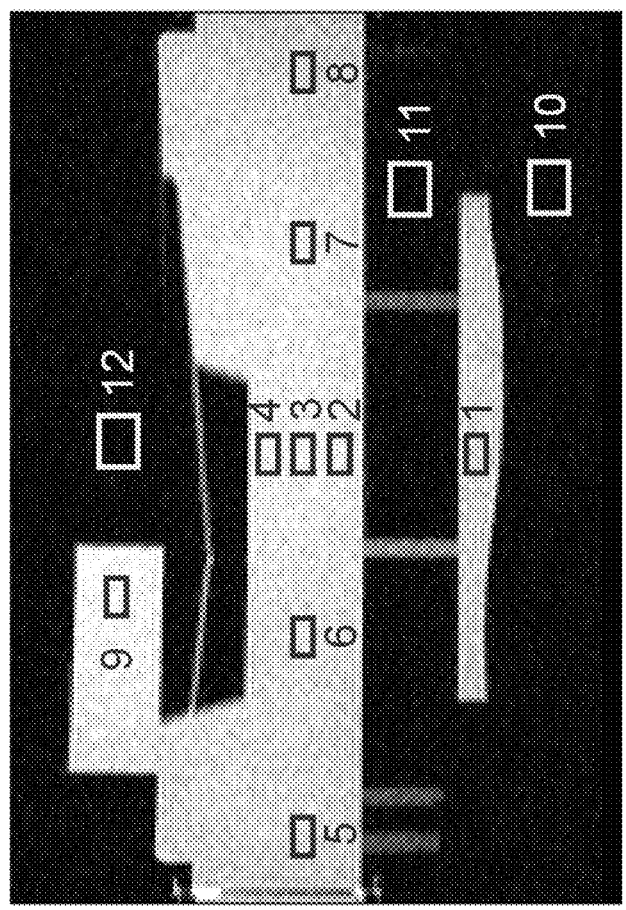
FIG. 2A is an MRI image captured without the use of a resonator array.

For example, FIG. 2A shows results of an MRI scan using conventional MRI technology without a resonator array 300. To produce these results, the inventors measured the strength of a signal at nine positions (numbered 1-9 in FIG. 2A) within the bore 102 of a 1.5 T MRI machine, and measured the noise at three positions (numbered 10-11) of the MRI machine. The inventors then calculated the average of the noise measurements, and then calculated the SNR of each signal measurement to the average of the noise measurement. The results are shown below, and reveal SNRs ranging from 33.2 to 39.0. These results may be referred-to as the "baseline" SNRs.

| Signal Strength (Mean) | | | | |
|---|---|---|---|---|
| 1 | 2 | 3 | 4 | |
| 157.2 | 173.2 | 178.5 | 178.1 | |
| 5 | 6 | 7 | 8 | 9 |
| 158.5 | 166.3 | 172.3 | 151.3 | 184.8 |

| Noise Level (StdDev) | | | |
|---|---|---|---|
| 10 | 11 | 12 | Avrg |
| 4.4 | 4.6 | 5.2 | 4.7 |

| SNR | | | | |
|---|---|---|---|---|
| 1 | 2 | 3 | 4 | |
| 33.2 | 36.6 | 37.7 | 37.6 | |
| 5 | 6 | 7 | 8 | 9 |
| 33.5 | 35.1 | 36.4 | 32.0 | 39.0 |

Figure 2B:
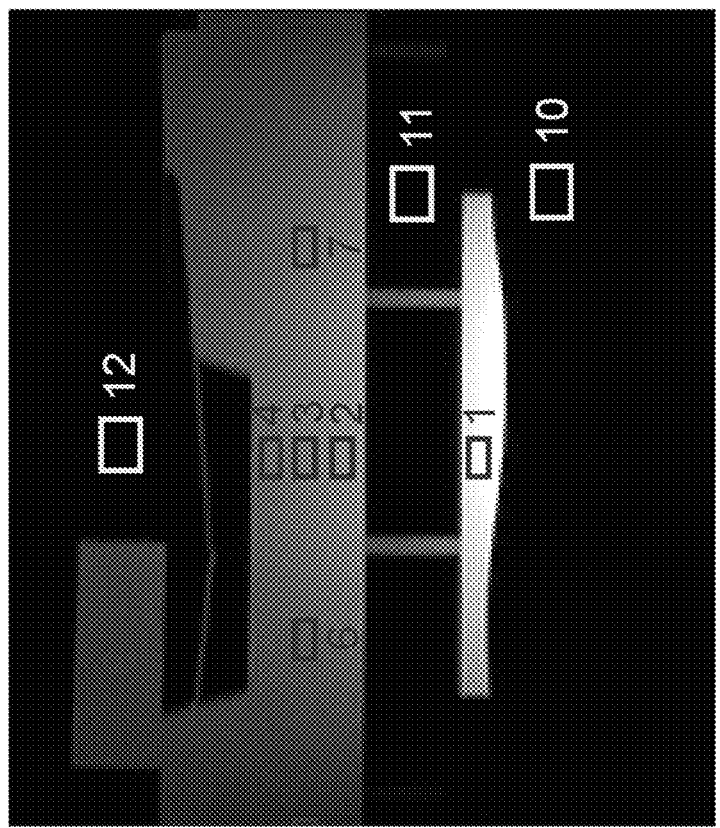
FIG. 2B is an MRI image captured with use of an embodiment of a resonator array.
Figure 2C:
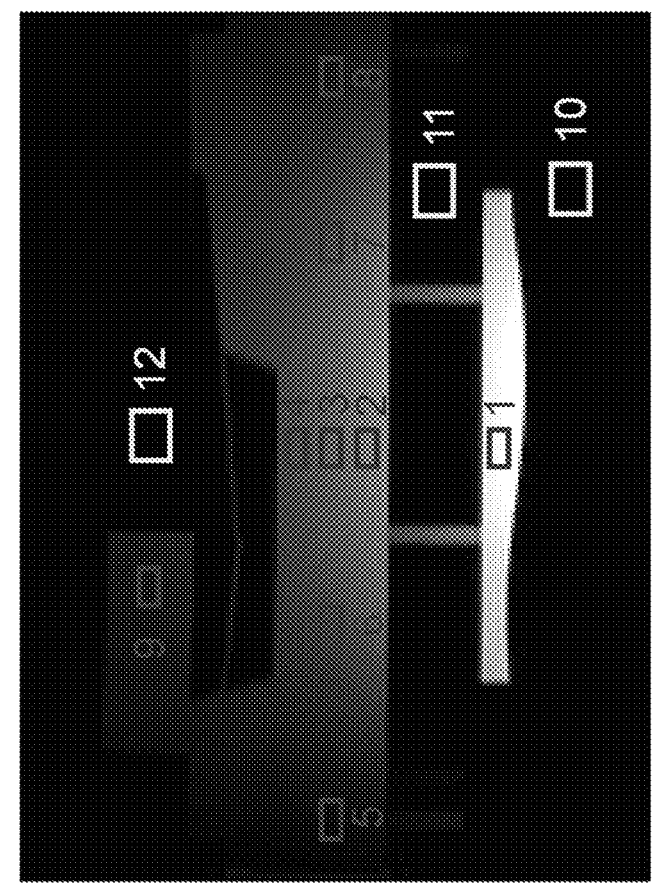
FIG. 2C is an MRI image captured with use of another embodiment of a resonator array.
Figure 5A:
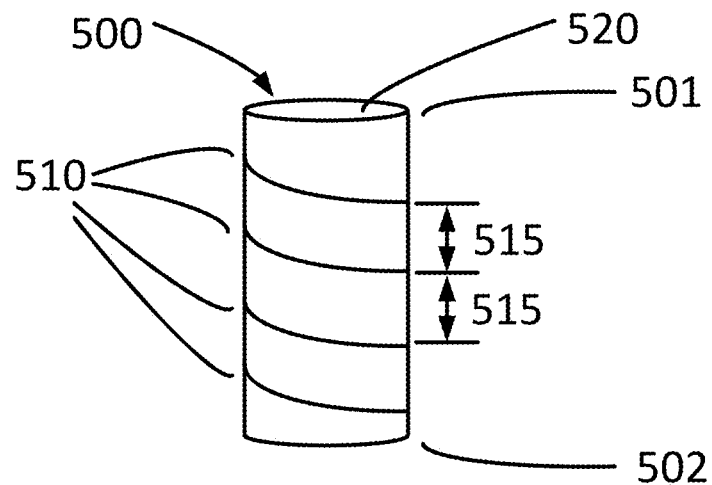
FIGS. 5A, 5B and 5C schematically illustrate an embodiment of a helical resonator.
Figure 5B:
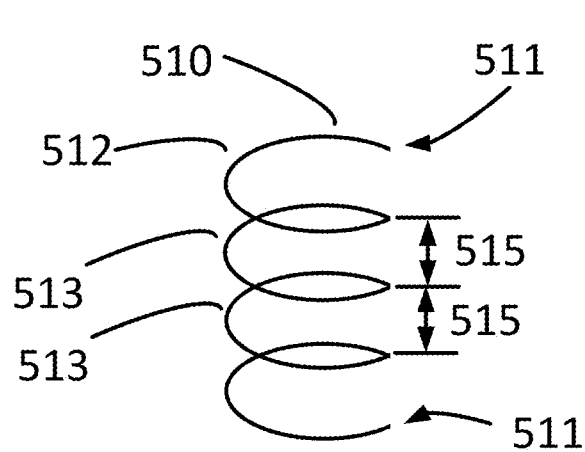
Figure 5C:
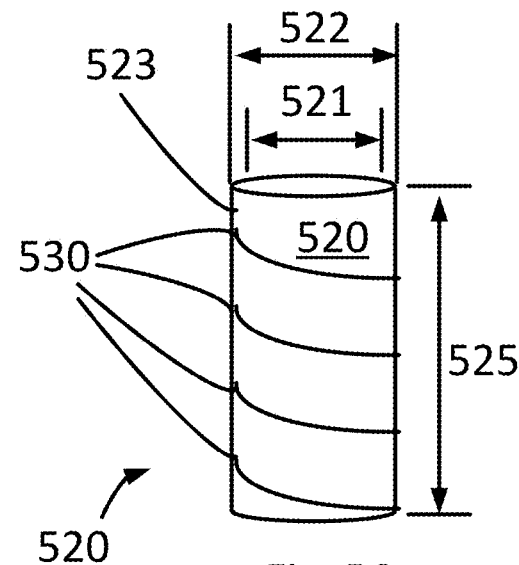

In contrast to the results shown in FIG. 2A, FIG. 2B and FIG. 2C each shows results of an MRI scan at the same nine positions using the same 1.5 T MRI machine with the resonator array 300 having unit cells 301 that are helical resonators 500 (e.g., FIG. 5A-5C). To produce these results, the inventors measured signal and noise in the way described above in connection with FIG. 2A, but obtained significantly improved SNRs.

In the embodiment for FIG. 2B, the SNRs were considerably higher than the baseline SNRs. The results are shown below, and reveal SNRs ranging from 68.4 to 277.3. Comparing the SNR for location 1 in FIG. 2B to the results for location 1 in FIG. 2A shows a large increase in SNR—from a baseline SNR of 33.2 to an improved SNR of 277.3.

| Signal Strength (Mean) | | | | |
|---|---|---|---|---|
| 1 | 2 | 3 | 4 | |
| 1174 | 640.4 | 546.6 | 481.1 | |
| 5 | 6 | 7 | 8 | 9 |
| 193.1 | 404.5 | 428.6 | 267.6 | 289.7 |

| Noise Level (StdDev): | | | |
|---|---|---|---|
| 10 | 11 | 12 | Avrg |
| 4.1 | 4.7 | 3.9 | 4.2 |

| SNR | | | | |
|---|---|---|---|---|
| 1 | 2 | 3 | 4 | |
| 277.3 | 151.3 | 129.1 | 113.6 | |
| 5 | 6 | 7 | 8 | 9 |
| 45.6 | 95.5 | 101.2 | 63.2 | 68.4 |

In the embodiment for FIG. 2C employed an array 300 in which the unit cells 301 had different periodicity (i.e., different spacing relative to one another) than the array employed to generate FIG. 2B. That embodiment also produced SNRs at the same nine positions that are considerably higher than the baseline SNRs. The results are shown below, and reveal SNRs ranging from 46.2 to 401.5 Comparing the SNR for location 1 in FIG. 2C to the results for location 1 in FIG. 2A shows a large increase in SNR—from a baseline SNR of 33.2 to an improved SNR of 401.5.

| Signal Strength (Mean) | | | | |
|---|---|---|---|---|
| 1 | 2 | 3 | 4 | |
| 1258.0 | 605.9 | 498.2 | 381.7 | |
| 5 | 6 | 7 | 8 | 9 |
| 95.9 | 363.6 | 343.1 | 156.6 | 144.9 |

| Noise Level (StdDev): | | | |
|---|---|---|---|
| 10 | 11 | 12 | Avrg |
| 2.7 | 3.5 | 3.2 | 3.1 |

| SNR | | | | |
|---|---|---|---|---|
| 1 | 2 | 3 | 4 | |
| 401.5 | 193.4 | 159.0 | 121.8 | |
| 5 | 6 | 7 | 8 | 9 |
| 30.6 | 116.0 | 109.5 | 50.0 | 46.2 |

In general, a resonator array 300 increases the SNR of signals emitted by a specimen. For a given MRI machine, relative to the SNR of signals received by that MRI machine without use of a resonator array, embodiments of a resonator array 300 increases the SNR of such signals to at least 45.6, 50, 60, 95, 100, 120, 150, and/or at least 193.4, or any point between 45 and 401.

Resonator Array

Figure 3A:
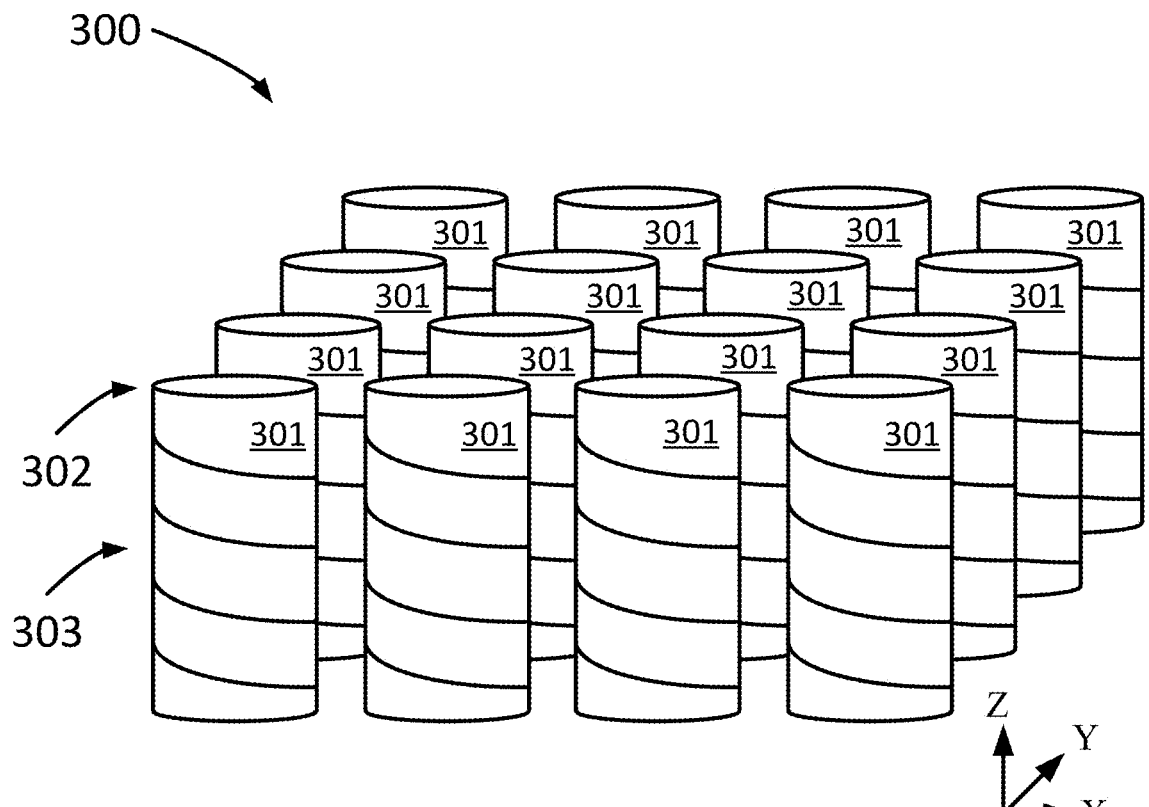
FIG. 3A and FIG. 3B schematically illustrate an embodiment of a resonator array.
Figure 3B:
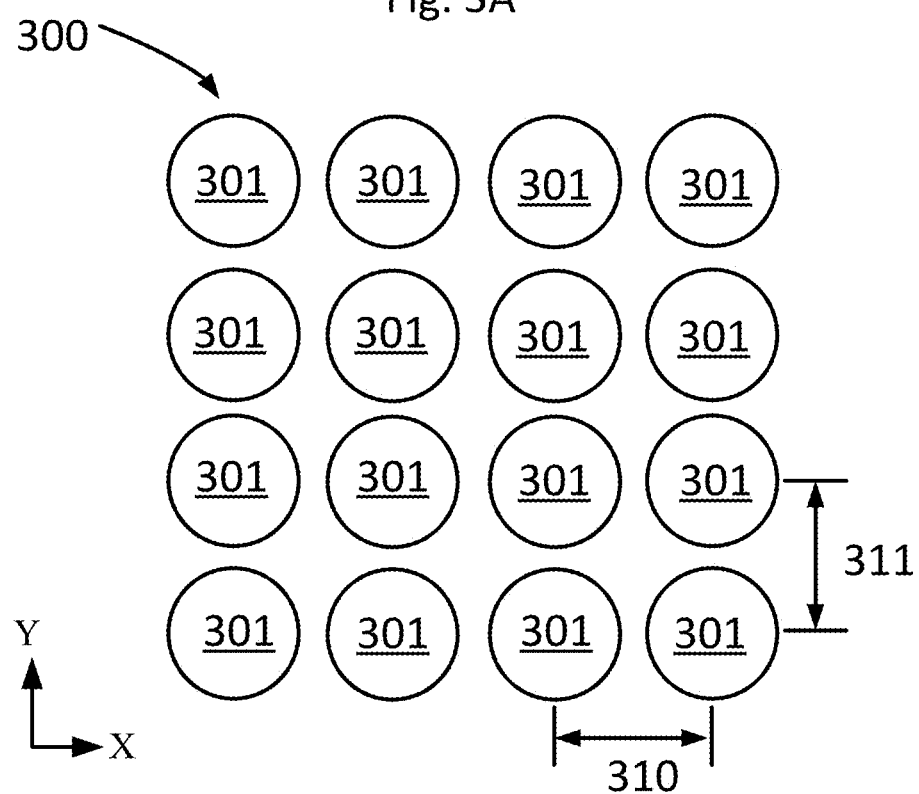
Figure 3C:
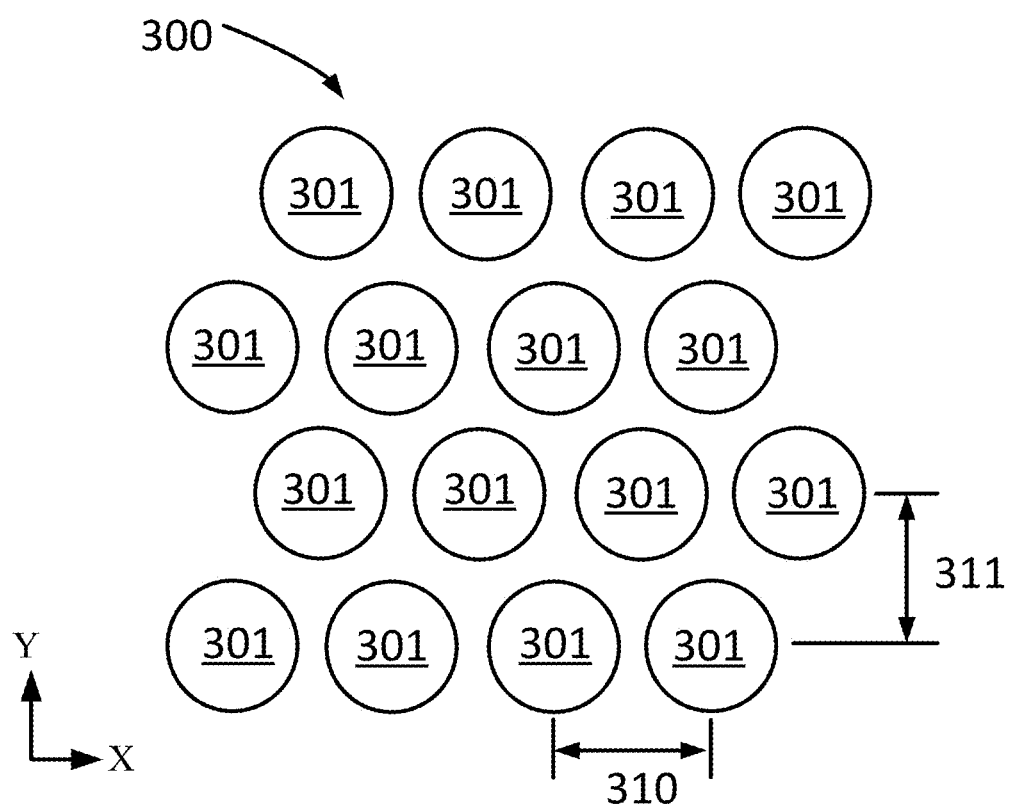
FIG. 3C schematically illustrates an embodiment of a honeycomb resonator array.

An illustrative embodiment of a resonator array 300 is schematically illustrated in FIG. 3A and FIG. 3B. The array 300 in this embodiment includes 16 unit cells 301, in a 4×4 array, but other embodiments may use more or fewer unit cells 301, and may be arranged in different arrangements, such as square, honeycomb [FIG. 3C], or rectangular for example.

Each unit cell 301 may also be referred to as a "resonator," because it is configured to resonate in response to applied electromagnetic signals, such as signals applied to a specimen 99 by an MRI machine 100, and/or signals received by the unit cell 301 from a specimen 99 in the MRI machine 100. For example, each unit cell may have an inductance (L) and a capacitance (C), and therefore resonate as do LC resonators known in the electrical engineering arts. Each unit cell 301 has a resonant frequency, and has a Q, as described in connection with FIG. 4A.

Figure 4A:
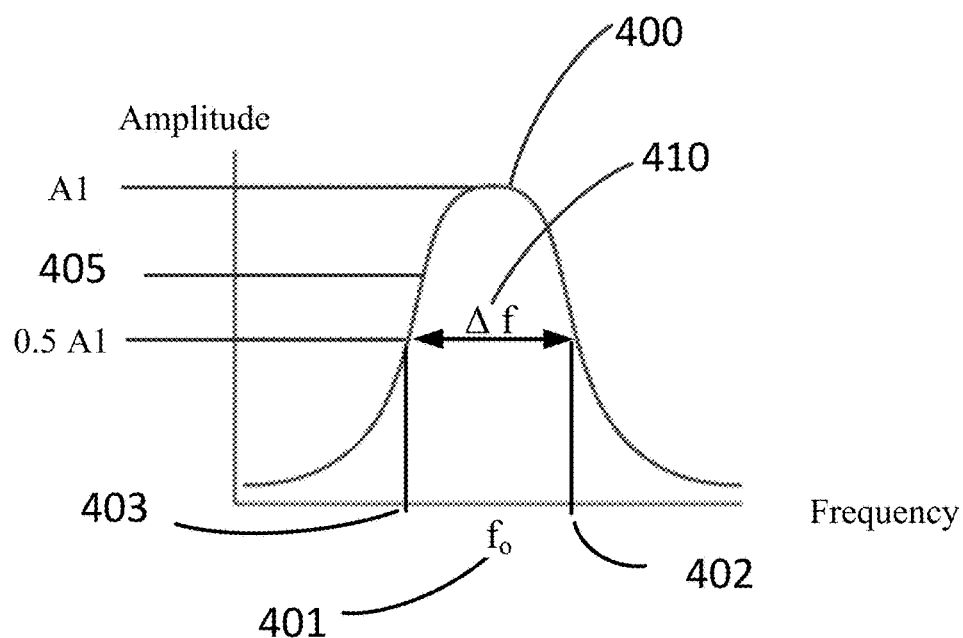
FIG. 4A is a graph illustrating quality factor of a resonating structure.

FIG. 4A graphically illustrates quality factor of a resonating device. A resonating unit cell may be characterized, in part, by its quality factor, which may be referred to as its "Q-factor," or simply as its "Q." A unit cell's Q-factor is a measure of its resonance characteristics.

For example, unit cell 301 may receive an electromagnetic signal emitted by an atom of a specimen 99 in an MRI machine 100, or from the MRI machine itself, and that electromagnetic energy may include energy at one or more frequencies. The energy will resonate in the unit cell 301, in ways known from LC circuits from the art of electrical engineering.

Ideally, the energy resonates at the resonant frequency $f_o$ (401) of the unit cell, although the unit cell 301 may resonate to some degree at lower frequencies as well, as illustrated by the curved spectrum in FIG. 4A. The maximum energy may be at frequency $f_o$ (401), which may be referred-to as the center frequency, represented by amplitude A1. At other frequencies, the energy is less than that at the center frequency 401, as also schematically illustrated in FIG. 4A. At some frequency 402 above the center frequency 401 (which may be known as the upper 3 dB frequency), and at another frequency 403 below the center frequency (which may be known as the lower 3 dB frequency), the energy in the resonating signal will be half of the energy at the center frequency 401. The spectrum 400 in FIG. 4A shows that some of the energy resonating in the unit cell 301 is above a noise floor, indicated at point 405.

The Q of the unit cell 301 is then defined as the ratio of the center frequency ($f_o$) divided by difference (Δf or delta-f) between the upper 3 dB frequency and the lower 3 dB frequency. In FIG. 4A, the Q is the center frequency 401 divided by the frequency difference 410 between upper 3 dB frequency 402 and lower 3 dB frequency 403. As such, Q is a dimensionless parameter.

In operation, a unit cell 301 may receive a packet of electromagnetic energy (e.g., RF energy) from one or more atoms in a specimen 99, the electromagnetic energy having a frequency at or near the working frequency of the MRI machine. For example, in preferred embodiments the electromagnetic energy having a frequency within +/−5% (inclusive) of the working frequency of the MRI machine is defined as being at or near the working frequency of the MRI machine. Over time (e.g., during the operation of the MRI machine), each unit cell 301 will receive many packets of electromagnetic energy, and store the sum of that energy. The higher the Q of the unit cell 301, the more efficiently the unit cell 301 stores the energy it receives.

In addition, as the unit cell 301 resonates, it amplifies the magnetic field component of that received electromagnetic energy, and increases the signal-to-noise ratio of the received electromagnetic energy. As such, each unit cell 301, individually, has the ability to resonate, without regard to other unit cells (if any) that may be nearby, and has some ability to amplify the magnetic field component of received electromagnetic energy.

The inventors have discovered, however, some limitations on the usefulness of individual unit cells 301. First, a single unit cell 301 has limited capacity to amplify the magnetic field component of received electromagnetic energy. Second, a unit cell 301 may have a resonant frequency that is not well matched to the MRI machine 100, in which case its ability to amplify the magnetic field component of received electromagnetic energy is less efficient than it would otherwise be. Third, it is not possible to change the resonant frequency, and/or the Q, of an individual unit cell 301, at least without disassembling and rebuilding the unit cell 301.

The inventors have also discovered, however, that an array 300 of unit cells 301 has characteristics that are different from a mere aggregation of the characteristics of its constituent unit cells 301. In other words, the resonator array 300 exhibits a synergy.

Figure 5D:
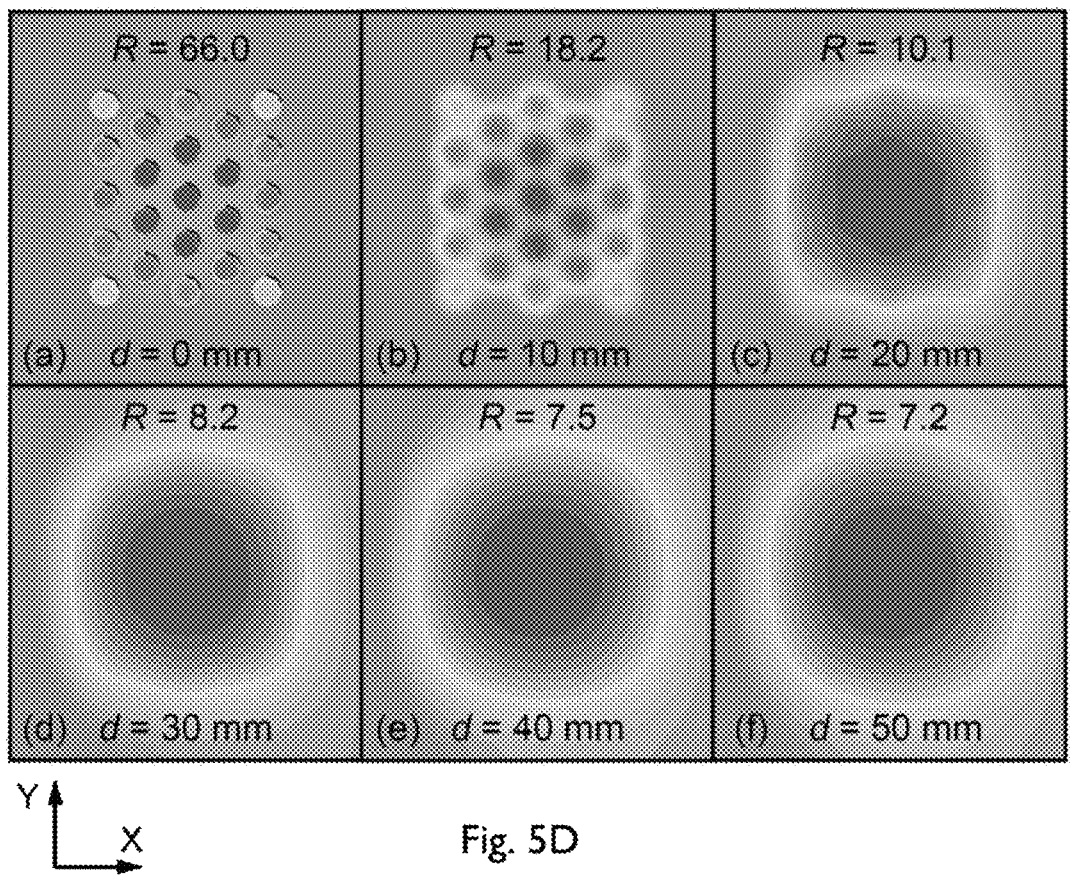
FIG. 5D and FIG. 5E schematically illustrate operating characteristics of an embodiment of an array of helical resonators.

For example, an array 300 of unit cells provides a homogenous amplification of the magnetic field component of received electromagnetic energy (see, e.g., FIG. 5D and the text that describes that figure).

In addition, the resonant frequency of the array 300 may not be the same as the resonant frequencies, respectively, of its constituent unit cells 301. Rather, the unit cells 301 couple to one another to produce the resonant frequency of the array 300. To that end, in preferred embodiments, the unit cells 301 magnetically couple to one another, and are not wired to one another.

Moreover, the resonant frequency of the array 300 may be tuned by adapting the spacing of the unit cells 301 within the array 300.

In addition, the array 300 is modular, in that unit cells 301 may be added to an array 300 at the same periodicity (i.e., X-pitch 310 and/or Y-Pitch 311) of unit cells 301 already in the array 300, without significantly changing the resonance characteristics of the array 300. Adding unit cells 301 to an array 300 at the same periodicity of unit cells 301 already in the array 300 does not change the resonance characteristics of the array as much as changing the periodicity of the unit cells 301 of the array 300. Adding unit cells in this way may be desirable, for example, to increase the size of the array 300 to image a larger specimen 99, or a larger portion of a specimen 99.

Similarly, unit cells 301 already in an array 300 with a given periodicity may be removed from the array 300 without significantly changing the resonance characteristics of the array 300. Removing unit cells 301 from an array 300 with a given periodicity does not change the resonance characteristics of the array as much as changing the periodicity of the unit cells 301 of the array 300. Removing unit cells may be desirable, for example, to reduce the size of the array to fit into the bore 102 of an MRI machine 100, or to image a smaller specimen 99, or a smaller portion of a specimen 99.

The resonator array 300 is configured to have a resonance frequency at or near the working frequency of the MRI machine 100 (i.e., the resonance frequency of the array is within +/−5%, inclusive, of the working frequency of the MRI machine 100). For example, the working frequency (or "operating frequency") of a 1.5 Tesla (i.e., 1.5 T) MRI machine is approximately 64 MHz (which is a radiofrequency for purposes of this disclosure), and the working frequency of a 3 Tesla (i.e., 3 T) MRI machine is approximately 128 MHz (which is also a radiofrequency for purposes of this disclosure).

The resonance frequency of the resonator array 300 is partially determined by the periodicity (spacing) of the unit cells 301 of the array 300, and also by the resonance frequency of the individual unit cells 301. In the illustrative resonator array 300 of FIG. 3A and FIG. 3B, the resonators are evenly spaced: each unit cell 301 is separated by a dimension, the X-pitch 310, of 37.33 mm in the X-axis, and by a dimension, the Y-pitch 311, of 37.33 mm in the Y-axis. In this configuration, the resonance frequency 463 of the resonator array 300 is centered at the working frequency 452 of the MRI machine 100. In general, the difference between the working frequency 452 of the MRI machine and the resonance frequency of the resonator array 300 may be specified by the designer or operator of the MRI machine. In preferred embodiments, the resonance frequency of the resonator array 300 is within +/−5% (inclusive) of the working frequency 452 of the MRI machine.

Figure 4B:
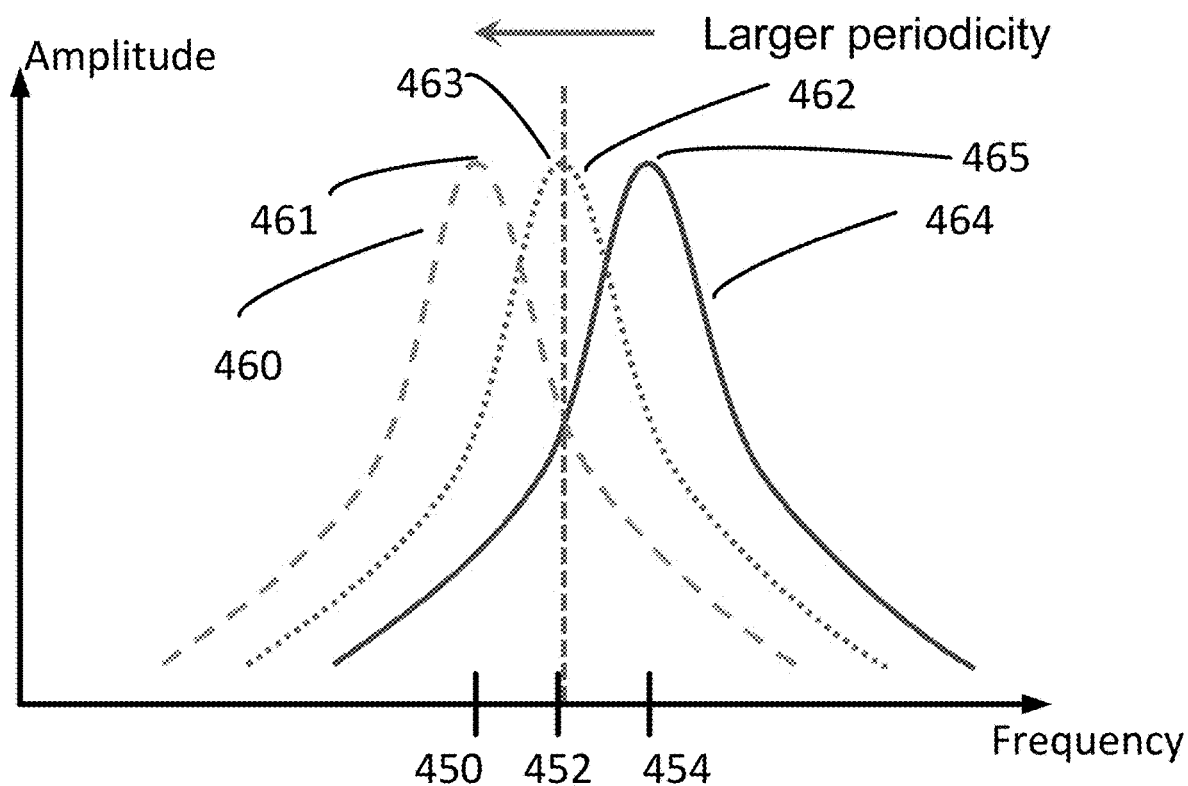
FIG. 4B graphically illustrates the relationship between the periodicity of a resonator array and its frequency response relative to the working frequency of an MRI machine.

At a larger periodicity (i.e., greater X-pitch 310 and Y-pitch 311), the resonance frequency of the resonator array 300 is reduced, and at a lower periodicity (i.e., smaller X-pitch 310 and Y-pitch 311), the resonance frequency of the resonator array 300 is increased. FIG. 4B graphically illustrates the relationship between the periodicity of a resonator array 300 and its frequency response relative to the working frequency 452 of an MRI machine. Curve 462 schematically illustrates the resonance of an array 300 tuned to the working frequency 452 of the MRI machine 100, with a resonant frequency at point 463. In contrast, curve 460 schematically illustrates the resonance of the array 300 tuned to a frequency 450 slightly below the working frequency 452 of the MRI machine 100, with its resonant frequency at point 461, and curve 464 schematically illustrates the resonance of the array 300 tuned to a frequency 454 slightly higher than the working frequency 452 of the MRI machine, with its resonant frequency at point 465.

Consequently, the resonance frequency of the resonator array 300 can be adjusted and established as necessary or desired for a given MRI machine or application. For example, the inventors have realized that the presence of soft tissue near the array 300 may change the permittivity of the area surrounding the array 300. If such a change of permittivity interferes with or degrades the operation of the MRI machine 100 or resonator the resonance frequency of the resonator array 300 may be adjusted by changing the spacing of the unit cells 301 of the resonator array 300.

Helical Unit Cell

An illustrative embodiment 500 of a unit cell 301 in the form of a helical resonator 500 is schematically illustrated in FIG. 5A, and FIG. 5B, and FIG. 5C. The resonator 500 includes a helical conductor 510 around a low-dielectric core 520.

The helical conductor 510, which may be copper, is wrapped around the core 520 so that each successive turn (513) (or "loop") around the core is separated from its predecessor by a gap 515.

The unit cell 301 has both inductance (L) and capacitance (C). The inductance arises from the coiled conductor 510, and the capacitance arises in the gap 515 between successive turns 513 of the conductor 510. Consequently, the resonant frequency of the unit cell 301 is determined, at least in part, by the number of turns 513 of the conductor 510 and the dimensions of the gap 515 between turns 513. A designer may therefore establish the resonant characteristics of the unit cell 301 to suit a desired application by establishing the inductance and capacitance through specification of its properties (e.g., the number of turns 513 and/or the gap 515) of the coiled conductor 510 and/or the dielectric constant (k) and/or loss angle of the core 520. Moreover, the resonant frequency of an array 300 of unit cells 301 may be tuned by specifying, or adapting, the resonant characteristics of the unit cells 301 by, for example, increasing or decreasing the number of turns 513 of the conductor 510, and/or increasing or decreasing the gap 515 between turns 513 of the conductor 510.

In some embodiments, the conductor 510 does not overlap itself, but in other embodiments the conductor 510 may overlap itself as long as there is no direct electrical contact between different regions of the conductor 510. For example, the conductor 510 may overlap itself if it includes an electrically insulating coating 512.

FIG. 5C schematically illustrates a core 520 without the conductor 510. In some embodiments, the outer surface 523 of the core 520 includes a helical groove 530 to receive the conductor 510 and define its helical shape.

The ends 511 of the conductor 510 do not connect to one another, or to another conductor, or to the conductor 510 of another resonator. Consequently, the conductor 510 may be referred to as an open-loop resonator or an open-loop coil or an open-loop helical resonator.

In preferred embodiments, the core 520 has a low dielectric constant (k) and a low loss angle. For example, the core 520 may be made of materials such as polyvinylchloride ("PVC"), which as a dielectric constant of 3 (k=3). As used herein, a dielectric constant (relative permittivity) lower than 15 is considered a "low-dielectric constant" (or "low relative permittivity") and dielectric constant (relative permittivity) greater than or equal to 15 is considered a "high-dielectric constant" (or "high relative permittivity").

Figure 5E:
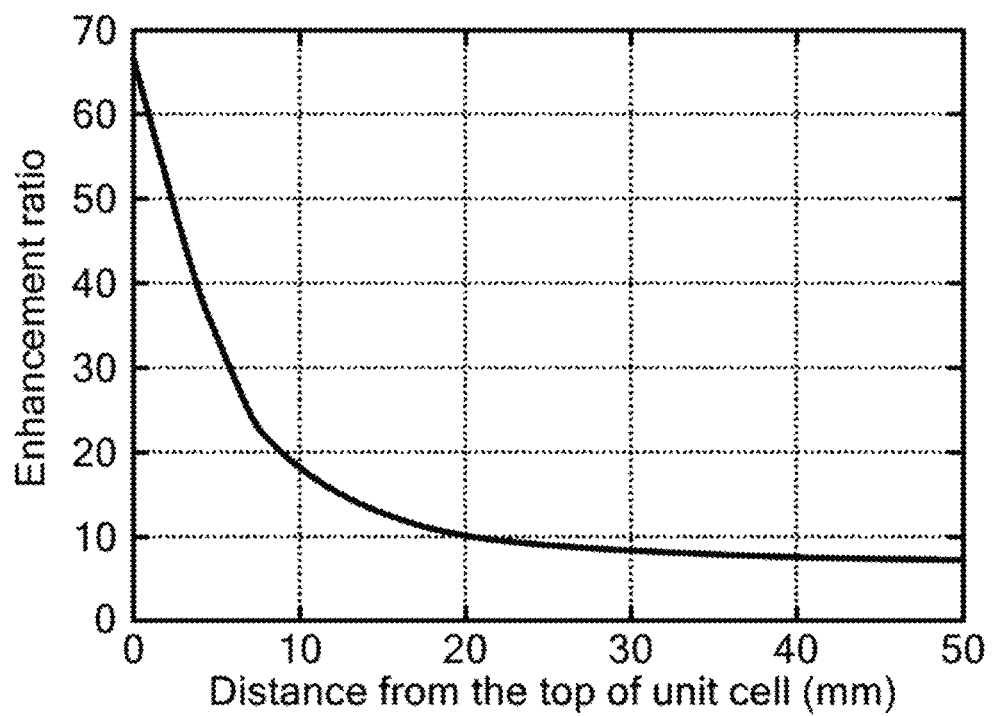

The core 520 in some embodiments may, however, have a dielectric constant of greater than 3, which reduces the size of the unit cell 301 while, possibly with adjustments of other properties of the unit cell 301, maintaining the same resonant characteristics. For example, the inventors experimented with water, which has a permittivity of approximately 80 at 20 degrees Celsius, as schematically illustrated in FIG. 5G and FIG. 5H and FIG. 5I. Unit cell 500 is placed in a dish 560 encircled by a coupling loop 561 which is coupled to a network analyzer. When the dish 560 is filled only with air, the unit cell 500 has a resonant frequency of 63 MHz, as shown by point 567 in FIG. 5I. However, when the dish contains water such that water fills about ten percent (10%) of the core 520 (the surface 566 of the water at 10%), the unit cell 500 has a resonant frequency of 55 MHz, as shown by point 568 in FIG. 5I. When the dish contains water such that water fills about twenty percent (20%) of the core 520 (the surface 566 of the water at 20%), the unit cell 500 has a resonant frequency of 39 MHz, as shown by point 569 in FIG. 5I. Consequently, it can be understood that including within a given unit cell 500 a material with a permittivity higher than the permittivity of air, the resonant frequency of the unit coil 500 is reduced. Conversely, to produce a unit cell 500 having a given resonant frequency, the unit cell 500 can be made smaller (e.g., have fewer turns 513), relative to a unit cell 500 having air in its core 520, of the interior 503 of the unit cell 500 has a relatively higher relative permittivity, for example between 86 and 173. For example, some embodiments include a core with a permittivity of between 86 and 173. In some embodiments, the relative permittivity may be even greater than 173. In some such embodiments include a core 520 made of titanium dioxide.

Some embodiments omit the core 520, and include a conductor 510 fixed into a helical shape (see, for example, FIG. 5B). In such embodiments, in air, the volume within the helical coil 510 has a dielectric constant of air, which is near one (k=1).

The characteristics of a helical resonator 500 may be determined by the type of MRI machine in which they will be used. In the embodiment of FIG. 5A, the core 520 is a hollow cylinder with an outside diameter 522, and an inside diameter 521, and a height 525. That shape and those dimensions, however, are not limitations of all embodiments, and other solid or hollow shapes may be used, including shapes having cross-sections that are square or triangular, to name but a few examples. Characteristics of illustrative embodiments of helical resonators 500 are given below for 1.5 T MRI machines and 3 T MRI machines.

| Characteristic | 1.5 T | 3 T |
| --- | --- | --- |
| Outside diameter 522 | 3.0 cm | 2.0 cm |
| Height 525 | 3.2 cm | 3.0 cm |
| Number of turns of conductor 510 | 25 | 25 |
| X-pitch 310 | 3.7 cm | 2.3 cm |
| Y-pitch 311 | 3.7 cm | 2.3 cm |

Operation of Resonator Array

In operation, the resonator array 300 is placed on or near a specimen 99 in an MRI machine 100, as schematically illustrated for example in FIG. 1A, FIG. 1B, FIG. 1C and FIG. 1D.

The resonator array 300 resonates at or near the working frequency 452 of the MRI machine 100, and thereby increases the magnetic field strength of the RF signals emitted by the specimen 99. In this way, the SNR of the RF signals is increased.

The resonator array 300 increases the magnetic field component of radiofrequency energy during signal transmission by the MRI machine 100 to the specimen 99, and reception of radiofrequency energy from the specimen 99 to the MRI machine.

For example, FIG. 5D graphically illustrates the magnetic field intensity at various elevations, above the top 302 of the unit cells 301 (e.g., in the Z axis), within an embodiment of a resonator array 300 in which the unit cells 301 are helical resonators 500. FIG. 5E graphically illustrates the magnetic field enhancement ratio at the center point of said array 300 as a function of distance from the middle 303 of the unit cells 301, and shows that the enhancement is greatest near the middle 303 of the unit cells 301, and decreases with distance from the middle 303 of the unit cells. It should be noted, from FIG. 5D, that the magnetic field enhancement is substantially uniform across the resonator array 300. In the helical resonator 500, magnetic field enhancement arises due to the overlap between the self-resonant frequency of the helical resonator 500 and the frequency of excitation of the magnetic field.

Beneficially, the resonator array 300 also substantially avoids generation of an electric field, or minimizes an increase in the electrical field component of those RF signals. For example, an electric field created at one end 501 of a resonator 500 very nearly completely cancels an electric field at the other end 502. Also, in various embodiments increase in the electrical field component of those RF signals less than the increase the magnetic field component of those RF signals. This is beneficial for specimen safety, since electrical fields may cause burns to the specimen, for example. Specifically, the helical resonators 500 are configured such that they do not couple with the electric field of the RF signals, thereby mitigating amplification by the helical resonators 500, and the array 300, of the electric field component of RF signals.

Figure 5F:
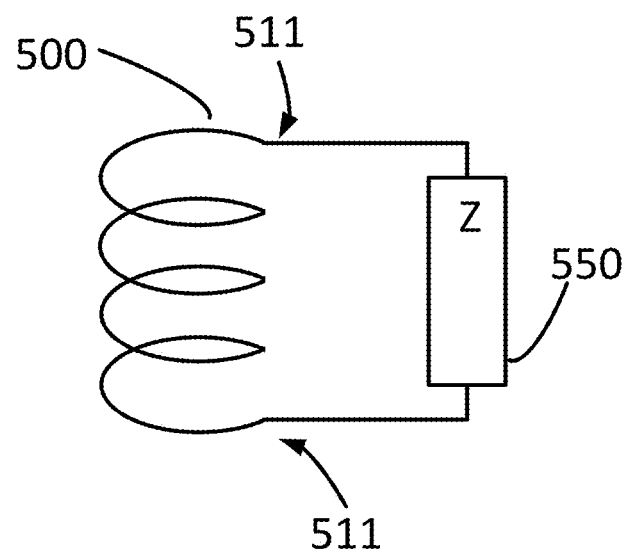
FIG. 5F schematically illustrates a helical resonator cell having an additional impedance.
Figure 5G:
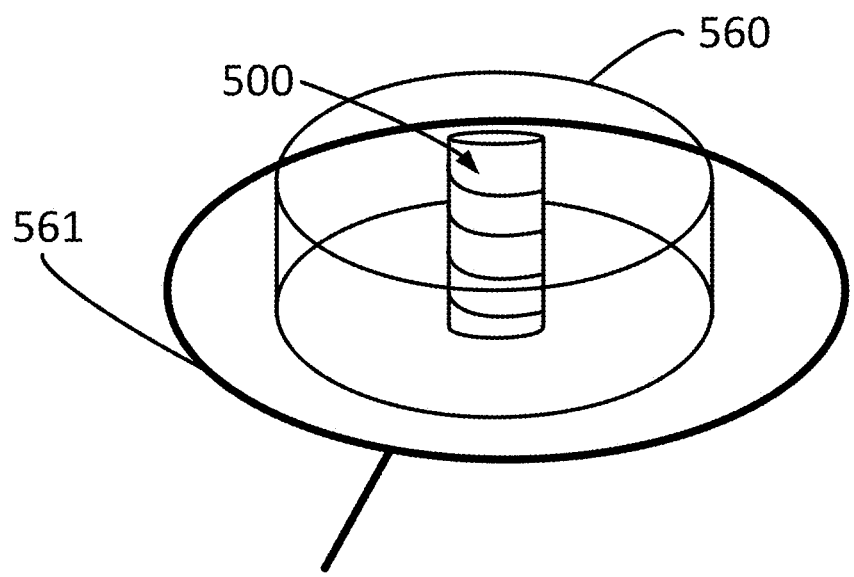
FIG. 5G and FIG. 5H schematically illustrate an embodiment of a unit cell with water in a dish to demonstrate the relationship between the unit cell's resonant frequency and the permittivity of the volume of the interior of the unit cell.
Figure 5H:
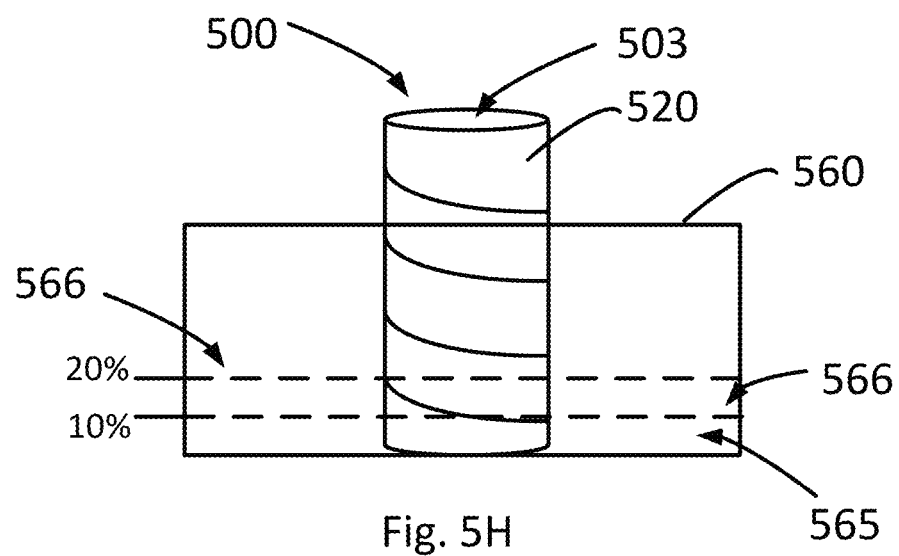
Figure 5I:
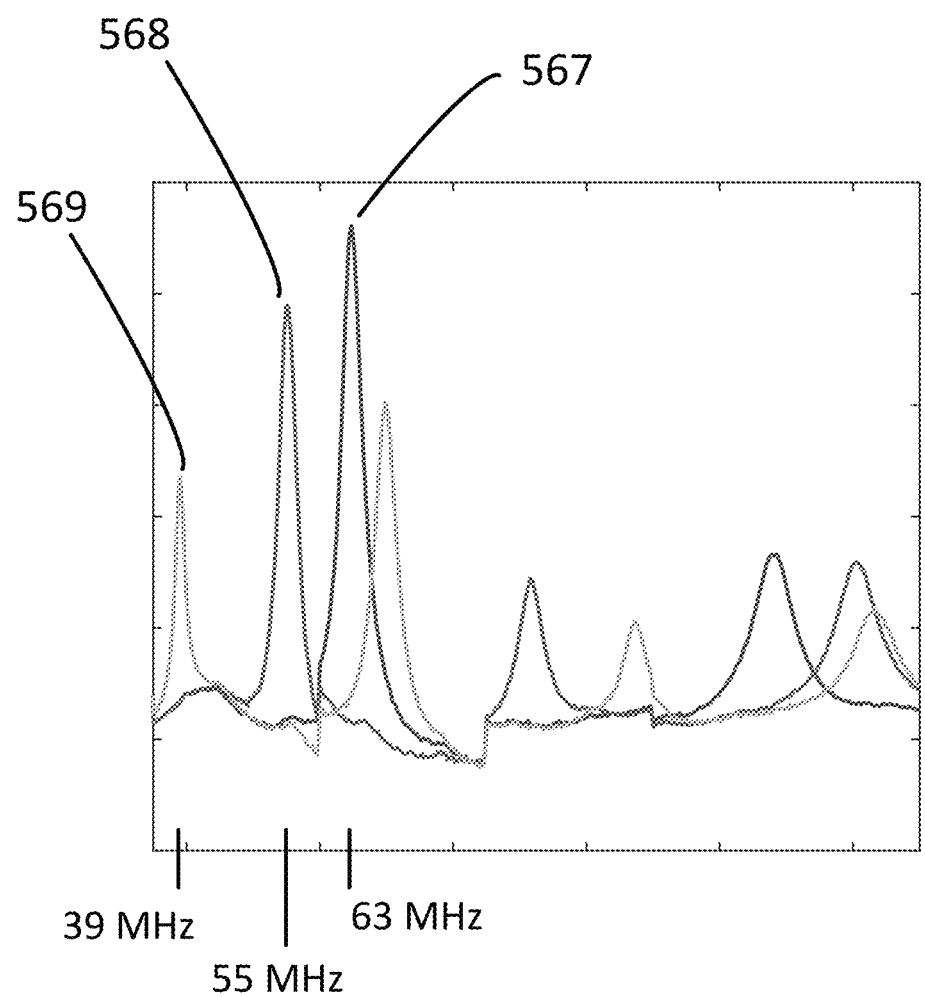
FIG. 5I schematically illustrates the relationship between the unit cell's resonant frequency and the permittivity of the volume of the interior of the unit cell.

FIG. 5F schematically illustrates an alternate embodiment of a helical resonator 500, including an additional fixed reactance 550 electrically coupled between the ends 511 of the unit cell's conductor 510. The additional reactance 550 is in addition to the inductance and/or capacitance of the conductor 510. The additional reactance 550 may be a capacitance (C), or an inductance (L). In practice, the additional reactance 550 interacts with the capacitance or inductance of the other structures of the helical resonator 500. For example, because the resonant frequency of the helical resonator 500 is dominated by $1/\sqrt{LC}$, inclusion of an inductor (L) in the additional reactance 550 produces a helical conductor 500 with the same resonant characteristics described above, but with a fewer number of turns 513 or/and a smaller diameter 521 of the helix. Likewise, inclusion of a capacitor (C) in the additional reactance 550 produces a helical conductor 500 with the same resonant characteristics described above, but requires less capacitance from the helical conductor 510.

BC-SRR Unit Cell

An embodiment of a unit cell 301, in the form of a broadside-coupled split ring resonator 600 ("BC-SRR"), is schematically illustrated in FIG. 6A. The BC-SRR resonator 600 includes two "C" shaped split-ring resonators 610, 620, each defining a gap 611 and 621, respectively. The split-ring resonators 610, 620 are disposed parallel to one another in the X-Y plane of FIG. 6A, and do not intersect or physically contact one another. As illustrated in FIG. 6A, the split-ring resonators 610, 620 are positioned such that their gaps, 611 and 621, are diametrically opposed to one another (i.e., 180 degrees from one another). The BC-SRR unit cells resonate well even if the gaps 611 and 621 are not 180 degrees from one another, but this is the preferred arrangement because the inventors have discovered that this arrangement produces the lowest electrical field. The top split-ring resonator 610 defines a top surface 601 of the BC-SRR 600, and a bottom surface 602 of the BC-SRR 600, for reference.

In the BC-SRR unit cell 600, magnetic field enhancement arises due to the overlap between the self-resonant frequency of the unit cells 600 and the frequency of excitation of the magnetic field. The BC-SRR unit cells are configured so that excited electric dipoles exhibit cancellation, thereby mitigating amplification by the unit cells 301, and the array 300, of the electric field component of RF signals.

FIGS. 6B-6D schematically illustrate operating characteristics of a BC-SRR 600 configured for resonance at 64 Mhz.

FIG. 6B schematically illustrates the magnetic field (Bz) distribution in a cross-section in the X-Z plane, of a single unit cell BC-SRR 600, and FIG. 6C schematically illustrates that magnetic field distribution in the X-Y plane 10 millimeters away from the top surface 601 of the BC-SRR 600. FIG. 6D schematically illustrates the magnetic field enhancement factor at a point 10 millimeters away from the top surface 601 of the BC-SRR 600. In this embodiment, an electric field created at one end of the BC-SRR 600 (i.e., the end nearest the top surface 601) very nearly completely cancels an electric field at the other end (i.e., the end nearest the bottom surface 602).

FIG. 6E schematically illustrates an array 300 of BC-SRR unit cells 600. In this embodiment, the BC-SRRs are photolithographically fabricated on a high-permittivity substrate 650.

Figure 7A:
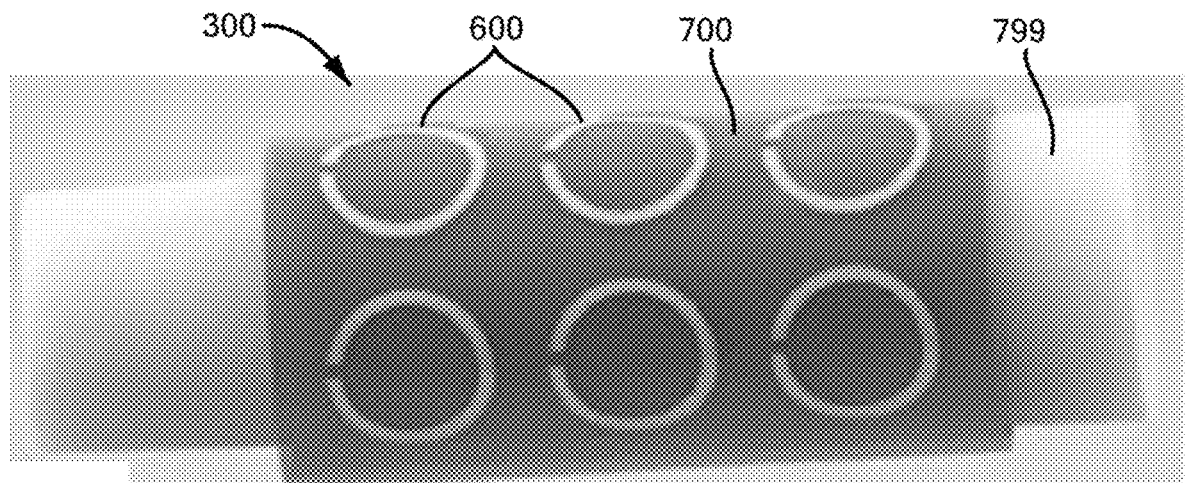
FIG. 7A and FIG. 7B schematically illustrate embodiments of flexible resonator arrays.
Figure 7B:
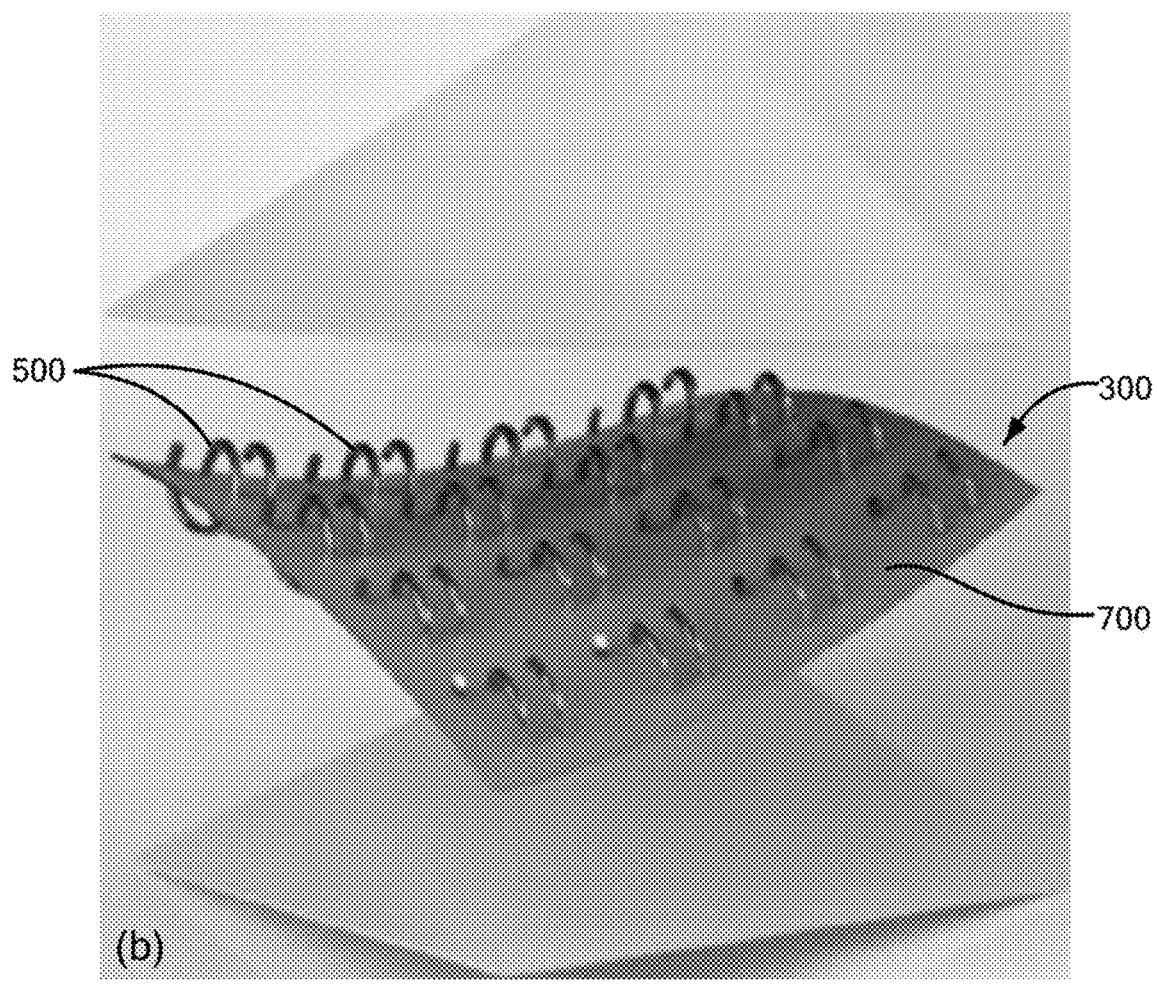

Embodiments of resonator arrays 300 may be rigid or flexible. For example, the array 300 of BC-SRR resonators in FIG. 6E may be rigid, while the arrays 300 of FIG. 7A and FIG. 7B are flexible. The BC-SRR array 300 of FIG. 7A has a flexible substrate 700, and as shown in FIG. 7A may even be wrapped around the limb 799 of a specimen 99, for example. Similarly, the array 300 of helical resonators 500 has a flexible substrate 700, and may be contoured to a portion of the body of a specimen 99, or even formed into a cone.

In some applications, it may be desirable to increase the magnetic field component of radiofrequency energy only during transmission of radiofrequency signals from the specimen to the MRI machine, and not during transmission of radiofrequency energy from the MRI machine 100 to the specimen 99. To that end, some embodiments include a tunable array 300 and tunable unit cells 301.

FIGS. 8A-8G schematically illustrate embodiments of tunable unit cells 301. An array 300 with tunable unit cells 301 is tunable by tuning its constituent unit cells 301.

FIG. 8A schematically illustrates a tunable unit cell 301. The tunable unit cell 301 may include, for example, a helical coil 500 as described above, or a BC-SRR 600 as described above, along with a coupler 801.

The coupler 801 has at least two electrical states (or "impedance" states), including a first state in which the electrical conductivity of the coupler 801 is lower than its electrical conductivity in the second state. Stated alternately, the electrical impedance of the coupler 801 is higher in the first state than it is in the second state. The resonant properties of the unit cell 301 vary depending on the state of the coupler 801.

In the embodiment of FIG. 8A, the coupler 801 is electrically coupled between the two ends 511 of a helical coil (e.g., 500), but may be coupled to one or more unit cells in several ways, as described below. In its first state, the impedance of the coupler 801 is sufficiently high that the operation of the unit cell 301 is as described above. In the second state, however, the impedance of the coupler is lower, creating an electrical connection via a conductive path between the two ends 511 of the coil 500. That electrical connection changes the properties of the helical coil 500 so that it no longer resonates, or so that its resonant frequency is shifted to a frequency away from the working frequency 452 of the MRI machine. In general, the difference between the working frequency 452 of the MRI machine and the helical coil's resonant frequency, when the coupler 801 is in the second state, may be specified by the designer or operator of the MRI machine. For example, in preferred embodiments, when the coupler 801 is in the second state, the resonant frequency of the helical coil 500 changes such that—if it resonates at all—its resonant frequency is at least +/−15 percent different than the working frequency 452 of the MRI machine, and/or at least +/−15 percent different than its resonant frequency when the coupler 801 is in the first state. Consequently, changing the state of the coupler 801 changes the resonant properties of the unit cell 301. In general, when the resonant frequency of a unit cell 300 (in this example, the helical coil 500) is at least +/−15 percent different than the working frequency 452 of the MRI machine, and/or at least +/−15 percent different than its resonant frequency when the coupler 801 is in the first state, the unit cell is said to be "effectively non-resonant."

Moreover, in an array 300 of such unit cells 301, changing the state of the coupler 801 changes the operating properties of the array 300. For example, when the coupler 801 is in the first state, each unit cell 301, and an array 300 of such unit cells 301, operate as described above in connection with FIGS. 3A-3C, 4A-4B, 5A-5F and 6A-6E. When the coupler 801 is in the second state, the resonant properties of the array 300 are changed such that amplification of the magnetic field produced by the array 300 is reduced. In effect, each unit cell 301, and the array 300, and can be "turned on" by placing the coupler 801 in the first state, and "turned off" by placing the coupler 801 in the second state. A variety of couplers 801, unit cell 301 configurations, and array 300 configurations, are described below. In general, the coupler 801 may be referred to as a non-linear material or non-linear device.

FIG. 8B schematically illustrates an array 300 of BC-SRRs 600. Each BC-SRR unit cell includes at least one coupler 801, and in some embodiments more than one coupler 801. The coupler 801 in FIG. 8B is referred to as a semiconductor patch 810. The semiconductor patch 810 may be, for example, doped silicon that changes its impedance in response to RF energy from the MRI machine 100, but not in response to the generally much lower amount of RF energy of signals from the specimen 99. The semiconductor patch may be said to be nonlinear.

In illustrative embodiments, the semiconductor material of the semiconductor patch 810 may be GaAs, InAs, or InSb, to name but a few examples. A preferred embodiment uses GaAs as the semiconductor material. Intrinsic GaAs, without doping, has a carrier density of $2.1*10^6$ cm$^{-3}$.

The properties of the semiconductor are tuned by doping. Doping is known in the semiconductor arts. In illustrative embodiments, the GaAs is doped it to have a carrier density of $3*10^7$ cm$^{-3}$.

In illustrative embodiments, a semiconductor patch 810 may be prepared from a 2 inch or 4 inch wafer (0.5 mm thick) of doped semiconductor (e.g., GaAs doped as above). The wafer is diced into patches with 3 mm by 5 mm in size, and two electrodes are patterned onto the patch in ways known in the semiconductor art, with micrometer size gap such as $2*10^{-6}$ m.

As schematically illustrated in FIG. 8A, the semiconductor patch 810 is electrically coupled (e.g., soldered) to unit cell 301. By applying alternating magnetic field (e.g., a radiofrequency electromagnetic signal), a strong electric field can be induced at the micrometer size gap as high as 400 kV/cm to excite the impact ionization at the gap.

In illustrative embodiments, when the MRI machine 100 is not applying such an alternating magnetic field (e.g., a radiofrequency electromagnetic signal), the conductivity of the semiconductor patch 810 is approximately $1*10^{-7}$ (ohm cm)$^{-1}$ (in illustrative embodiments, with carrier density up to $10^7$ cm$^{-3}$). In contrast, when the MRI machine 100 applies stimulus as described above, the conductivity of the doped GaAs of the semiconductor patch 810 increases to approximately 20 (ohm cm)$^{-1}$ (in illustrative embodiments, with carrier density up to $10^{18}$ cm$^{-3}$), resulting in the resonant frequency shift of the unit cell 301 described herein.

Taking a doped semiconductor patch 810 as an example, during transmission of RF energy by the MRI machine 100, the electric field at the gap of the BC-SRR 600 or inside the metallic helices 500 is very high, and so the carrier density of the doped silicon semiconductor patch 810 is excited to a much higher level than in the absence of such RF energy. In this state, the doped silicon semiconductor patch 810 can be treated as a conductor. Consequently, during transmission of RF energy by the MRI machine 100, the resonant frequency of the unit cells 301 deviates from the frequency of RF energy transmitted by the MRI machine 100.

In contrast, during reception by a unit cell 301 of RF signals from the specimen 99—which occurs when the MRI machine 100 is not transmitting RF energy—the above-mentioned electric field strength is much lower, and so the doped silicon semiconductor patch 810 is not an effective conductor. Consequently, the resonant frequency of each unit cell 301 remains aligned with the working frequency 452 of the MRI machine 100, as the doped silicon semiconductor patch 810 is functioning as an isolator.

The semiconductor patch 810 is disposed within the first gap 611 of the first SRR 610 in the BC-SRR 600, and changes its state in response to RF energy from the MRI machine 100. More specifically, in the absence of RF energy from the MRI machine 100, the semiconductor patch 810 is in the first state (high impedance), so the BC-SRR 600 behaves as described above in connection with FIGS. 6A-6E. When the MRI machine transmits RF energy, however, the semiconductor patch 810 changes its impedance to the second state (low impedance), thus electrically coupling the opposing ends 612, 612 of the first gap 611, thereby changing the physical and resonant characteristics of the BC-SRR 600, and thereby changing the operating characteristics of the array 300, as described above.

In some embodiments, each of the SRRs 610, 620 of a BC-SRR 600 includes a semiconductor patch 810 as described above, to even further change the characteristics of each unit cell 301 and of the array 300.

FIG. 8C schematically illustrates an array 300 of helical unit cells 500. In this embodiment, a semiconductor patch 810 is coupled between the respective ends 511 of adjacent unit cells 301, and preferably is disposed within the interior 802 if the helical coil itself—e.g., surrounded by the helical turns 513. In this configuration, in the absence of RF energy from the MRI machine 100, the semiconductor patch 810 is in the first state (high impedance), so the resonator 500 behaves as described above in connection with FIGS. 5A-5F. When the MRI machine transmits RF energy, however, the semiconductor patch 810 changes its impedance to the second state (low impedance), thus coupling together the adjacent unit cells 301, and thereby changing the operating characteristics of the array 300, as described above.

FIG. 8D and FIG. 8E schematically illustrate an alternate embodiment of a coupler 801, in which the coupler 801 is a switch 820, and alternate embodiments of arrays 300 with such couplers 801. Although the unit cells 301 in these embodiments respond to the control signal 821 (and therefore may be said to be in control communication with the MRI machine 100 or its controller 140), each of the arrays 300 may still be considered passive in that it does not require input of external energy in order to amplify the magnetic field and increase the SNR of signals from the specimen 99.

In FIG. 8D, at least one SRR 610 of each BC-SRR 600 has a switch 820 disposed in its gap 611. A control signal 821 from the MRI machine (e.g., from controller 140) changes the switch 820 between its first state (high impedance) and second state (low impedance), thus electrically coupling the opposing ends 612, 612 of the first gap 611. Those two states change the resonant characteristics of the BC-SRR 600, and thereby change the operating characteristics of the array 300, as described above in connection with FIG. 8B. In some embodiments, each of the SRRs 610, 620 of a BC-SRR 600 includes a switch 820 as described above, to even further change the characteristics of each unit cell 301 and of the array 300.

FIG. 8E schematically illustrates an array 300 of helical unit cells 500. In this embodiment, a switch 820 is coupled between the respective ends 511 of adjacent unit cells 301. A control signal 821 from the MRI machine changes the switch 820 between its first state (high impedance) and second state (low impedance). Those two states change the resonant characteristics of the helical cell 500, and thereby change the operating characteristics of the array 300, as described above in connection with FIG. 8C.

Figure 9:
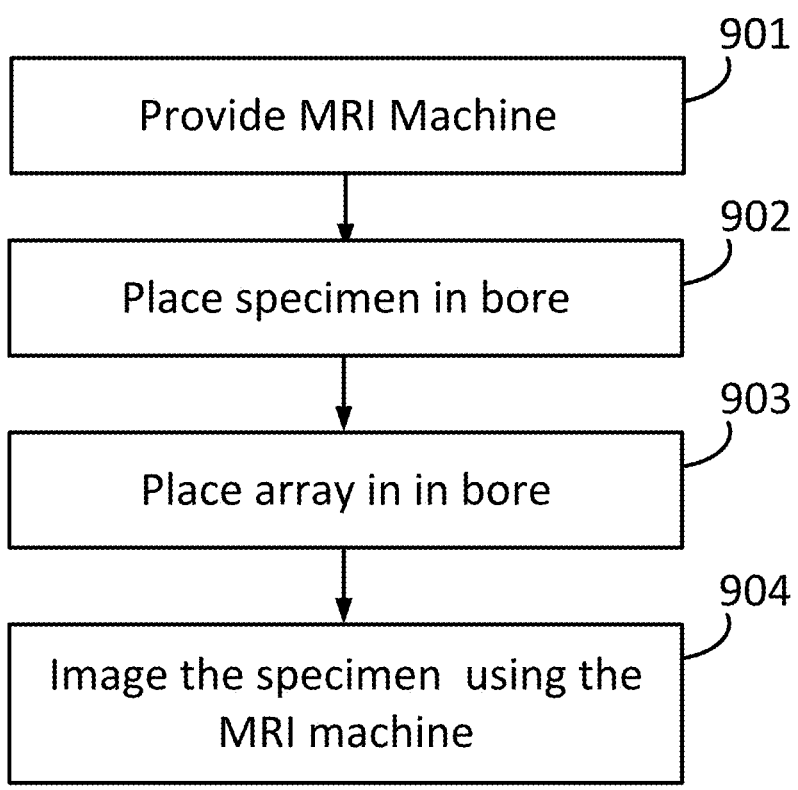
FIG. 9 is a flow chart for a method of imaging a specimen.

FIG. 9 is a flow chart for an embodiment of a method of magnetic resonant imaging a specimen 99. Step 901 requires providing an MRI machine 100 having a bore 102 and a working frequency. The MRI machine 100 may be, for example, a 1.5 Tesla MRI machine having a working frequency of 64 MHz or a 3 Tesla MRI machine having a working frequency of 128 MHz.

Step 902 includes placing the specimen in the bore 102, and step 903 includes placing, in the bore with the specimen, an array 300 of unit cells 301. It should be noted that steps 902 and 903 may be performed in any order with respect to one another.

In preferred embodiments, the array 300 is sized to be disposed within the bore 102 of the MRI machine 100 along with a specimen 99 in the bore 102, when the MRI machine 100 is imaging the specimen 99. For example, the array 300 of unit cells 301 may be any of the arrays 300 disclosed above.

In preferred embodiments, each unit cell 301 of the array 300 has a resonant frequency, and the array 300 has a resonance frequency at or near the working frequency of the MRI machine 100.

At step 904, the method images the specimen 99 with the MRI machine in ways known in the art.

In some embodiments, step 904 further includes controlling the coupler 801 to be in its first state (high-impedance) when the MRI machine is not applying electromagnetic (e.g., radio frequency) stimulus to the specimen 99, and to be in its second state (low impedance) when the MRI machine is applying such stimulus to the specimen. For example, if the coupler 801 is a switch 820, step 904 may include controlling the switch 820 with a control signal 821 from controller 140, as described above. As another example, if the coupler 801 is a semiconductor patch 810, step 904 may include controlling the semiconductor patch 810 to be in its first state (high-impedance) by withholding electromagnetic stimulus from the MRI machine 100, and controlling the semiconductor patch 810 to be in its second state (low-impedance) by applying electromagnetic stimulus from the MRI machine 100. In such embodiments, the coupler 801 is in a high-impedance state (and so the unit cells 301 resonate) when the MRI is not applying electromagnetic stimulus to the specimen, and the coupler 801 is in a low-impedance state (and so the unit cells 301 are effectively non-resonant) when the MRI is applying such electromagnetic stimulus to the specimen.

Nonlinear Controllable Array

In some applications, it may be desirable to control a metamaterial array 300 to cause the metamaterial array 300 to amplify a response signal from a specimen 99 in an MRI machine 100 without amplifying the excitation signal provided to the specimen 99 by the MRI machine 100. Moreover, it may be desirable to automatically control the metamaterial array 300 to that end, without requiring the MRI machine or a separate controller to coordinate the control of the metamaterial array with the operation of the transmission and reception modes of the MRI machine.

To those ends, embodiments described below describe a controllable array assembly 1100 (which may be referred-to as a nonlinear metamaterial, or "NLMM") that includes a linear metamaterial ("LMM") 300 (such as one or more of the metamaterial arrays described above in this application) in conjunction with a nonlinear control resonator 1000, such as a varactor loaded split-ring resonator ("VLSRR").

The nonlinear metamaterial 1100 is configured to be deployed within the bore 102 of an MRI machine 100, and operates to enhance the SNR of the MRI, achieving marked improvements in performance. It should be understood that the linear metamaterial 300, and/or the nonlinear metamaterial 1100 are not part of the MRI machine 1000 (e.g., they are not part of the body coils 102, or other coils, of the MRI machine 100). Instead, the nonlinear metamaterial 1100 may be described as an accessory for use with an MRI machine 1000.

In illustrative embodiments, the resonance of the controllable array assembly 1100 is suppressed in response to higher degrees of radiofrequency excitation strength (from the MRI machine 100) and recovers during a subsequent low excitation strength phase (from the MRI machine 100), thereby exhibiting an intelligent, or nonlinear, behavior by passively sensing the strength of the excitation signal from the MRI machine 100 and responding accordingly. The nonlinear response of the NLMM 1100 enables such embodiments to boost the signal-to-noise ratio during magnetic resonance imaging to an unprecedented degree. Such embodiments demonstrate an intelligent and nonlinear metamaterial, capable of adaptively varying its resonance response according to the excitation strength.

Some embodiments may be described as "self-adaptive" or having a "self-adaptive" response. In the RF transmission phase of the MRI machine 100, the strong excitation RF magnetic field induces a nonlinear response in the controllable array assembly 1100, effectively turning off its magnetic field enhancement performance due to its resonance shift. During the RF reception phase stage of the MRI machine 100, the controllable array assembly 1100 becomes active, operating at the resonance frequency of the MRI machine 100 and enhancing the received RF response signal.

Figure 10A:
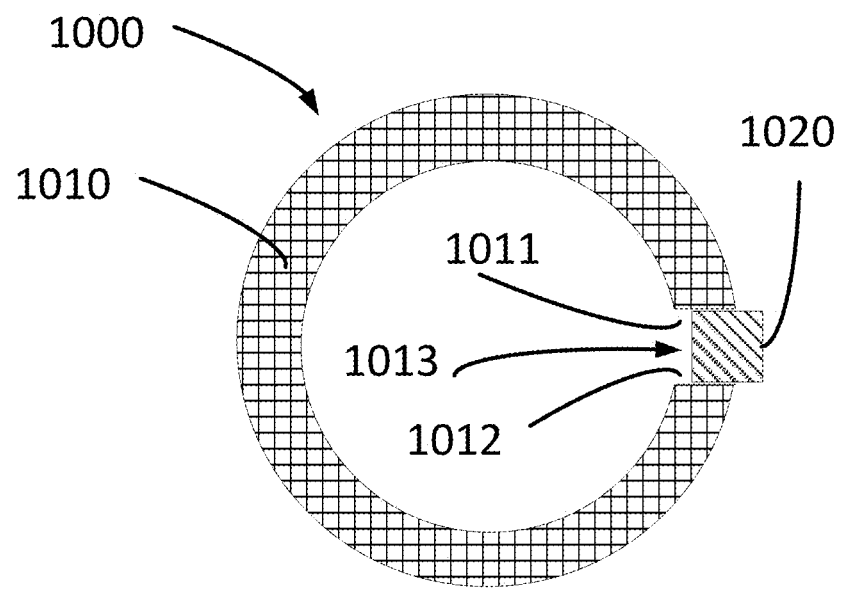
FIG. 10A schematically illustrates an embodiment of a non-linear resonator.

FIG. 10A schematically illustrates an embodiment of a non-linear resonator 1000, which may be referred-to as a control resonator. The non-linear characteristics of the non-linear resonator 1000 derive from its resonating characteristics, in that it has at least two distinct resonance frequencies, and can be controlled to assume a first one of the resonance frequencies, and then to switch to a second one of the resonance frequencies.

To that end, the non-linear resonator 1000 includes a resonator coil 1010, having a first end 1011 and a second end 1012. The resonator coil 1010 has an inductance and a capacitance, and an electrical resonant frequency.

Figure 10B:
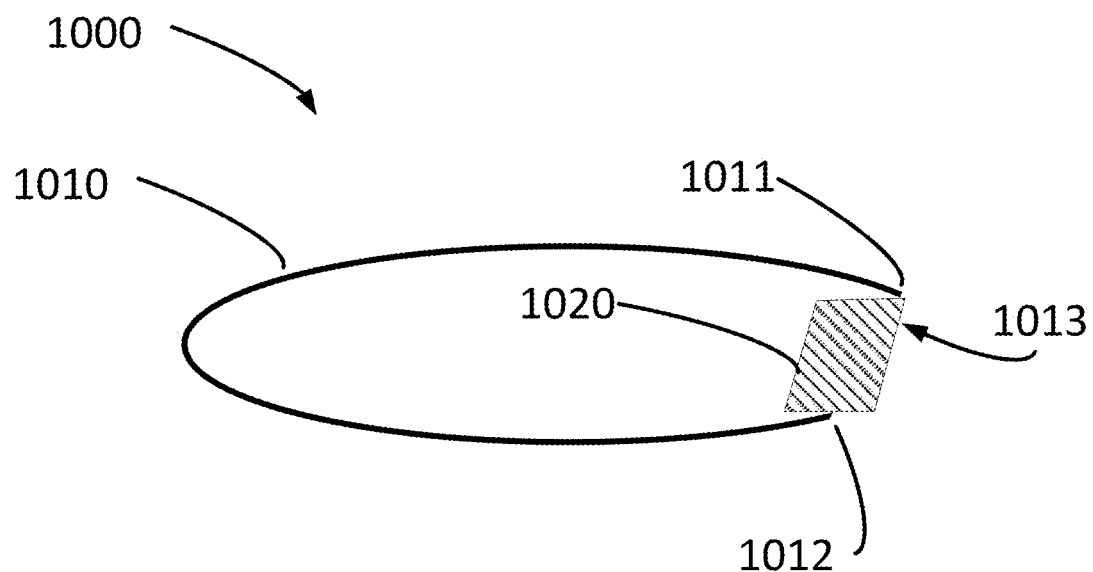
FIG. 10B schematically illustrates an embodiment of a non-linear resonator.

In some embodiments, the resonator coil 1010 is a split-ring resonator, in which the first end 1011 and the second end 1012 form the gap 1013 in the split ring. In other embodiments, the resonator coil 1010 is a conductive loop or helical coil as schematically illustrated in FIG. 10B, and in which the first end 1011 and the second end 1012 are ends of the coil 1010 and form gap 1013.

The non-linear resonator 1000 also includes a control coupler 1020 electrically coupled between the first end 1011 and the second end 1012. The control coupler 1020 has a controllably variable impedance.

For example, in some embodiments, the coupler 1020 has a capacitance that can be controllably changed between a first impedance state (e.g., a first capacitance) and a second impedance state (e.g., a second capacitance). Such a control coupler 1020 may be a varactor for example.

In other embodiments, the control coupler 1020 may be a transistor, such as a field-effect transistor, or a micro-electromechanical ("MEMS") switch. In some embodiments, the coupler 1020 is welded to the ends 1011, 1012 of the coil 1010.

The resonant frequency of the non-linear resonator 1000 is determined by the resonant frequency of the resonator coil 1010, and the impedance of the coupler 1020. Because the impedance of the coupler 1020 is controllably variable between the first impedance state and the second impedance state, the resonant frequency of the non-linear resonator 1000 is correspondingly controllably configurable into a first resonance state and a second resonance state. In other words, when the coupler 1020 is in a first impedance state, the non-linear resonator 1000 is in a first resonance state, and when the coupler 1020 is in a second impedance state, the non-linear resonator 1000 is in a second resonance state.

In illustrative embodiments, the controllable array assembly 1100 consists of an array 300 of linear helical resonators and a coupled varactor-loaded split ring resonator 1000, featuring a bi-stable nonlinear response under high power RF excitation.

FIG. 11A schematically illustrates an embodiment of a controllable array assembly (or nonlinear metamaterial assembly) 1100. FIG. 11B schematically illustrate another embodiment of a controllable array assembly 1100 and its constituent parts. Illustrative embodiments remain silent during the transmission phase of MRI, allowing for the uniform and optimal excitation of the specimen 99, and become active during the reception phase, leading to enhancement of the magnetic field and amplification of the signal-to-noise ratio of the response signal from the specimen 99.

The controllable array assembly 1100, in illustrative embodiments, is configured to magnify certain signals in the bore 102 of an MRI machine 100, and may be referred-to as a signal magnifying system. It should be noted that the controllable array assembly 1100 is not a part of the MRI machine 100, but is instead an accessory that can be used with the MRI machine 100.

The controllable array assembly 1100 includes an array 300 of metamaterial resonators. The array 300 of metamaterial resonators may be any of the arrays 300 of metamaterial resonators disclosed herein, for example. Illustrative embodiments of the array 300 include at least two metamaterial resonators, but may include more than two metamaterial resonators, such as a N×M array of such resonators, where N and M are integers (e.g., where N and/or M may be any of 2, 3, 4, 5, 6, 7, 8).

The controllable array assembly 1100 also includes a non-linear resonator 1000 (which may be referred-to as "control resonator" 1000) disposed adjacent to the array 300 of metamaterial resonators. The non-linear resonator 1000 and array 300 define a gap 1111 between them. In some embodiments, the gap 1111 may be 2 cm, for example. In other embodiments, however the gap 1111 may be greater than or less than 2 cm. For example, in some embodiments, the non-linear resonator 1000 may be disposed to be co-planar with the array 300, such that the gap 1111 is 0 cm (zero centimeters). FIG. 11E is a graph showing the magnetic field (B) enhancement ratio for points at different locations from the top surface of the array (LMM).

Illustrative embodiments of the controllable array assembly 1100 include a spacer layer 1110 disposed between the non-linear resonator 1000 and the array 300. In some embodiments, the spacer layer 1110 includes a non-metallic and non-magnetic material, such as plastic or foam, for example. In other embodiments, the spacer layer 1110 may be a vacuum, or a gas, such as air.

Figure 11C:
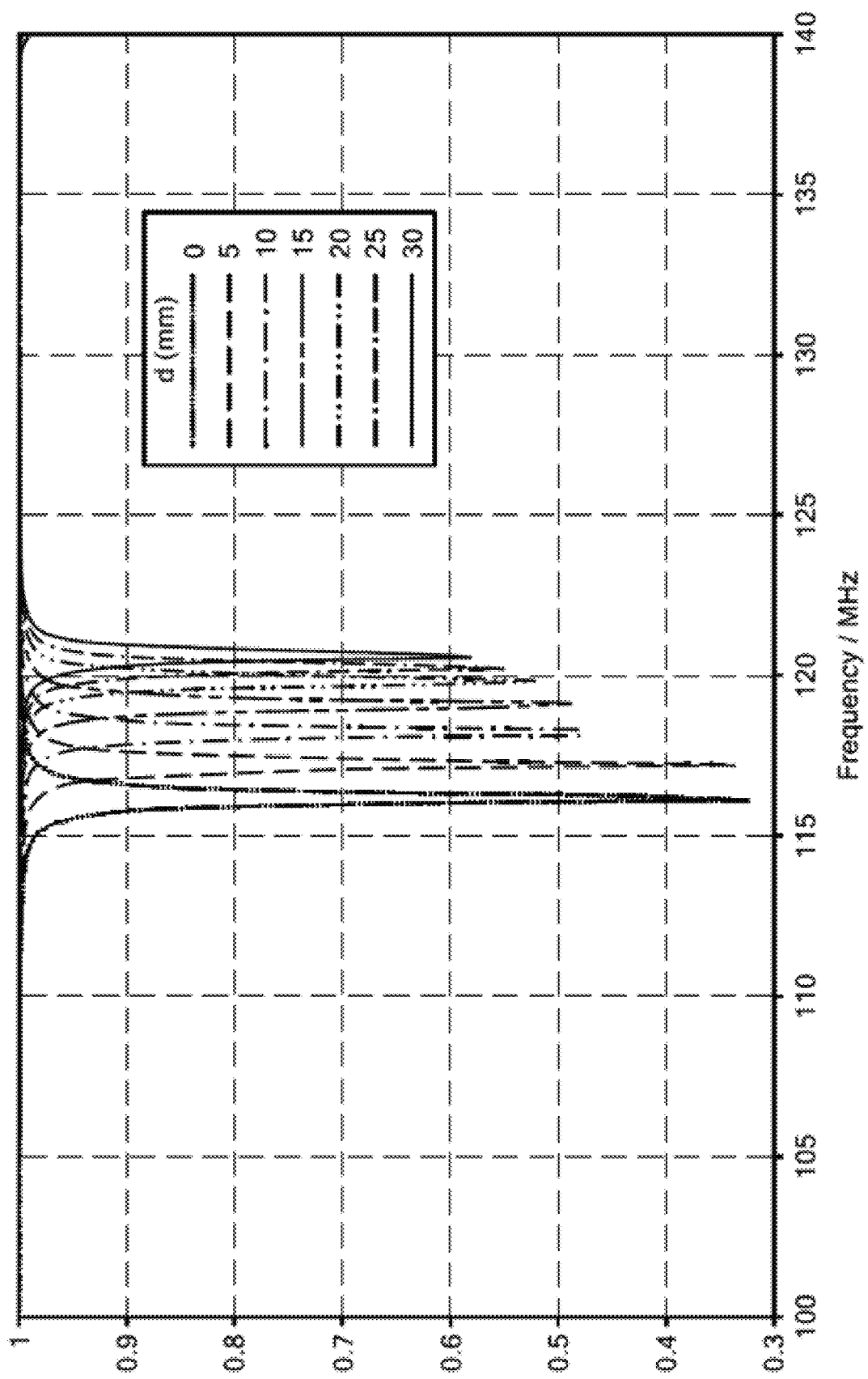
FIG. 11C is a graph showing the spectra of the controllable array assembly for different gaps between the array and the non-linear resonator.

FIG. 11C is a graph showing the spectra of the controllable array assembly 1100 for different gaps 1111 between the array 300 and the non-linear resonator 1000.

Figure 11D:
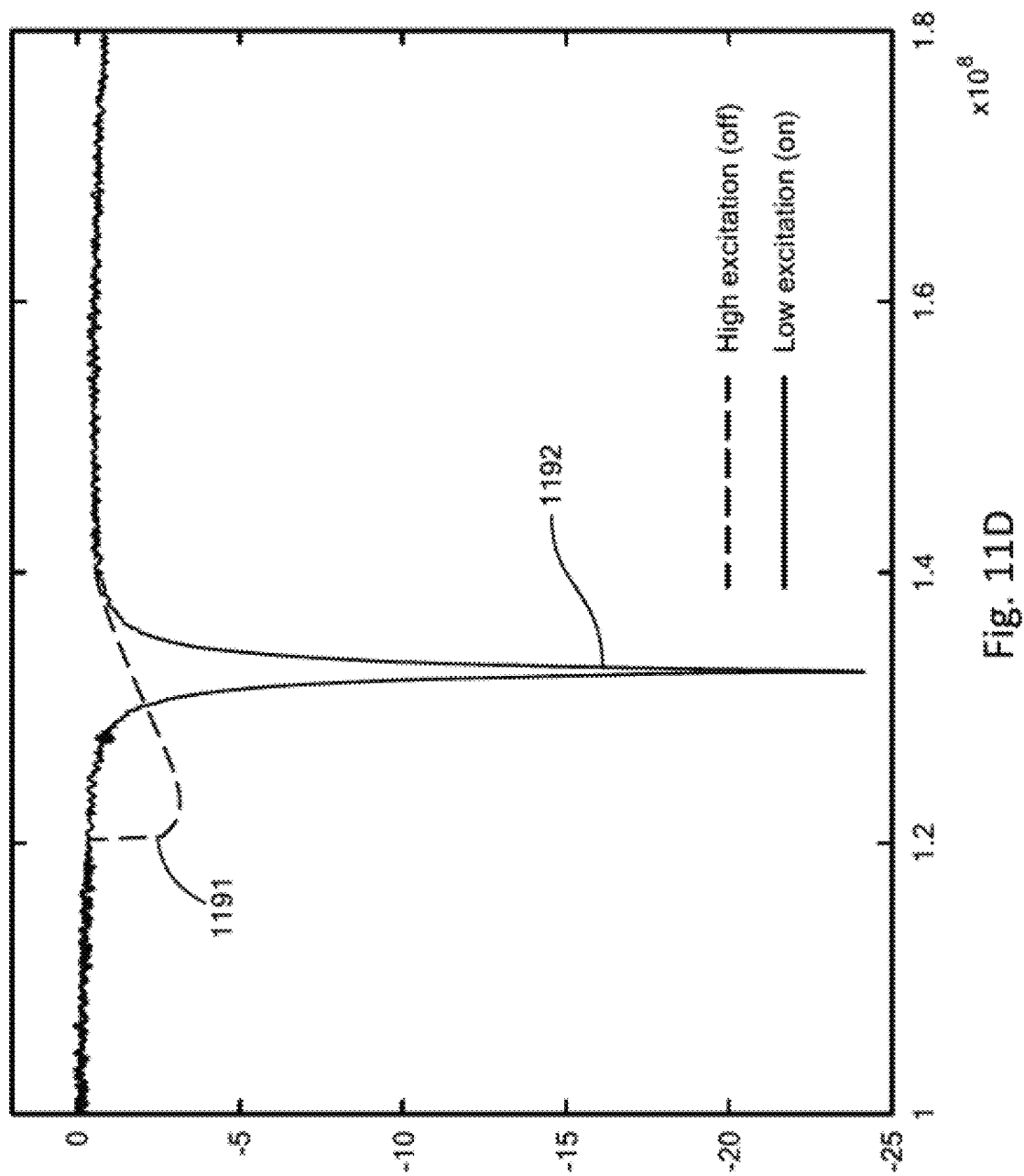
FIG. 11D is a graph showing the spectra of the controllable array assembly for high excitation, and for low excitation.
Figure 11E:
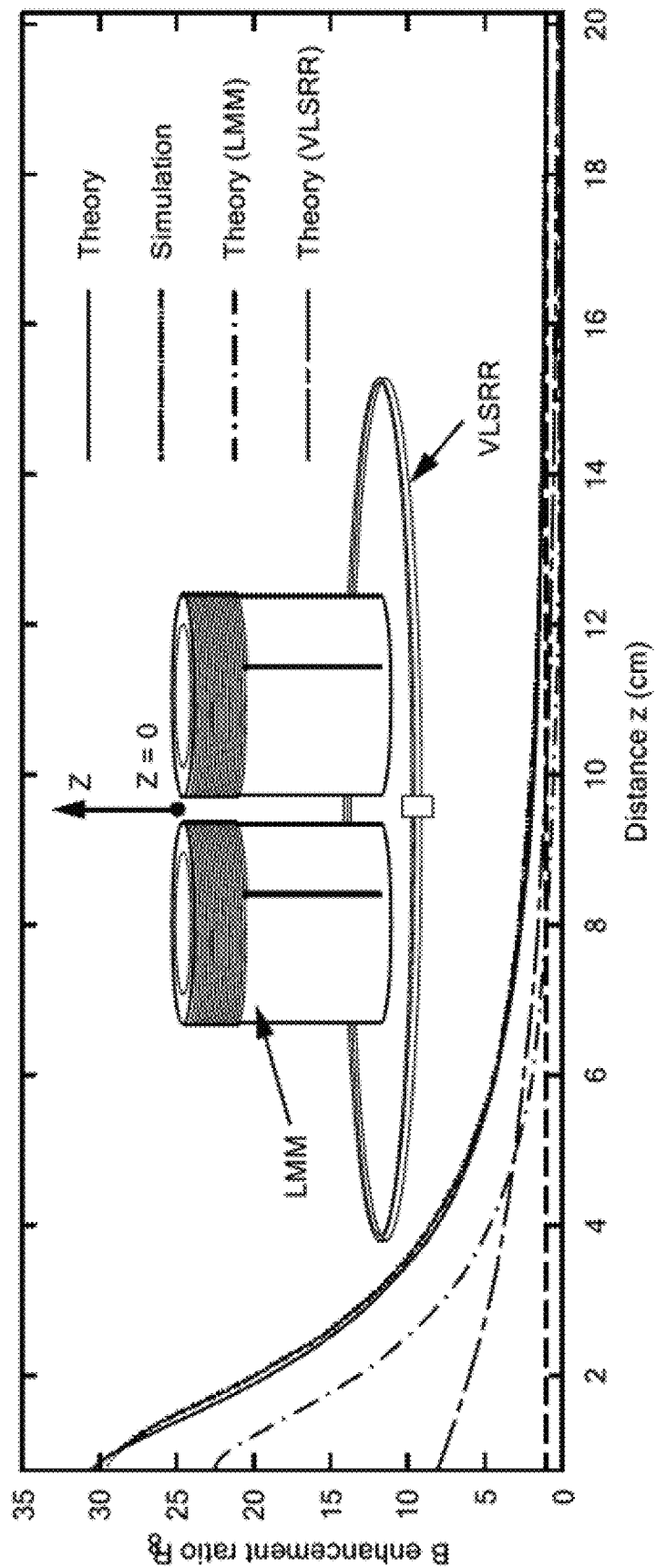
FIG. 11E is a graph showing the magnetic field (B) enhancement ratio for points at different locations from the top surface of the array (LMM)

FIG. 11D is a graph showing the spectra of the controllable array assembly 1100 for high excitation (i.e., during the transmission phase of the operation of the MRI machine 100 during which the MRI machine 100 provides an excitation signal to a specimen 99 in the bore 102 of the MRI machine), and for low excitation (i.e., during the reception phase of the operation of the MRI machine 100 during which the specimen 99 produces its response to the excitation signal). For high excitation (transmission phase of MRI operation), the resonance is off (line 1191), and for low excitation (reception phase of MRI operation), the resonance is on (line 1192), enhancing the magnetic field of the response signal produced by the specimen 99.

FIG. 12A, FIG. 12B, FIG. 12C, FIG. 12D, FIG. 12E, and FIG. 12F schematically illustrate another embodiment of a controllable array assembly 1100 and its constituent parts.

The response of the array 300 may be expressed by the following formula (Equation 1), in which $a_1$ represents the mode amplitude of the resonator, $1/\tau_{e1}$ and $1/\tau_{01}$ are the decay rates due to the radiation loss and ohmic loss, respectively, and $s_+$ represents the excitation signal:

$$\frac{da_1}{dt} = \left[ j\omega_{o1} - \frac{1}{\tau_{e1}} - \frac{1}{\tau_{01}} \right] a_1 + \sqrt{\frac{2}{\tau_{e1}}} s_+$$

Figure 12A:
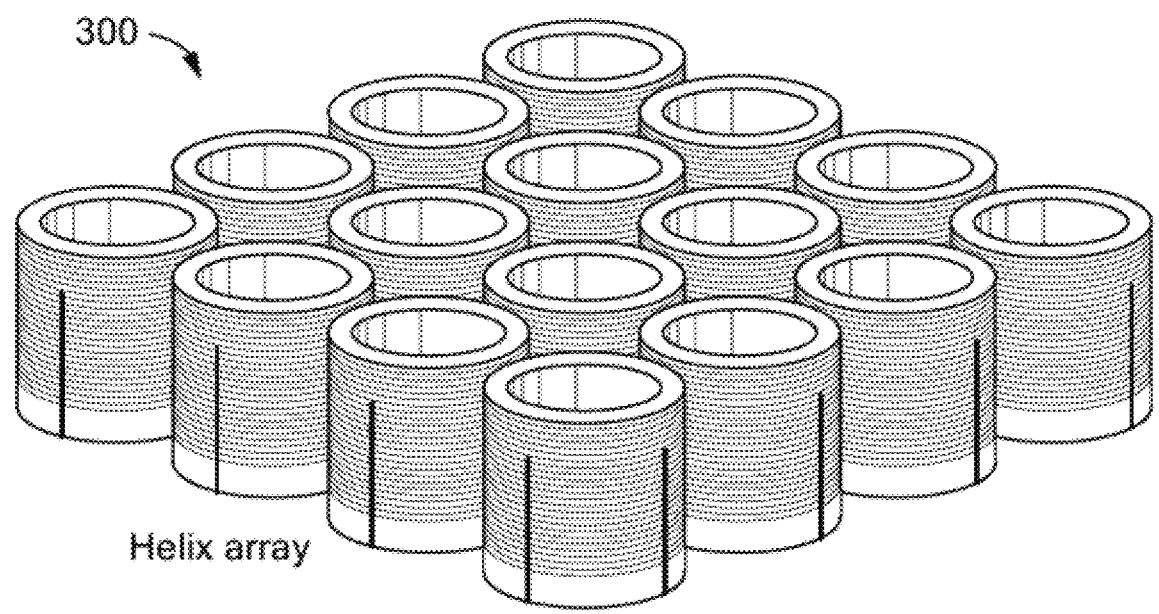
FIG. 12A, FIG. 12B, FIG. 12C, FIG. 12D, FIG. 12E, and FIG. 12F schematically illustrate another embodiment of a controllable array assembly.
Figure 12B:
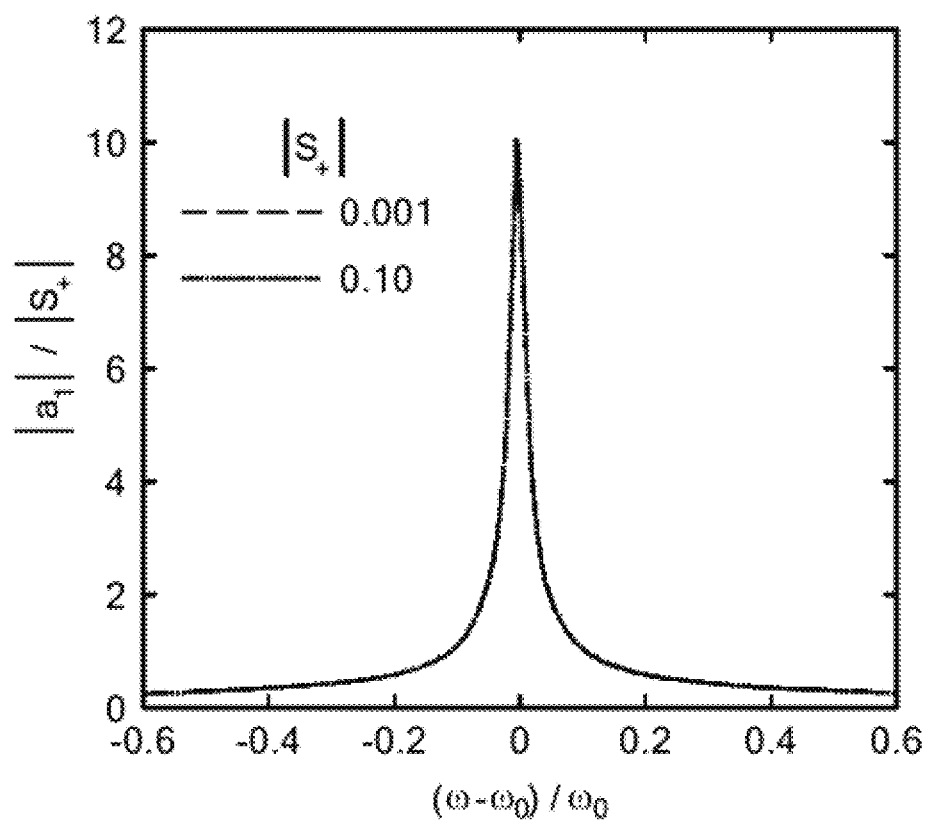

For an linear metamaterial consisting of an array 300 of helices, as shown in FIG. 12A, the response of its collective mode may be simply modeled using Eq. (1), with the oscillation strength of a resonator array maximized at the resonance frequency. The response of the resonator ($|a_1|/|s_+|$) is independent of the excitation strength, as illustrated by the results shown in FIG. 12B. The resonance of the metamaterial array 300 induces a magnetic field enhancement in the near field of the array 300. Of note, coupled mode theory ("CMT") provides a lumped parameter description of the response but neglects design details, therefore, this approach remains valid for linear metamaterial arrays 300 consisting of arbitrary numbers of unit cells, such as single unit cell, 2×1, or 4×4 unit cell configurations, to name but a few examples.

Figure 12C:
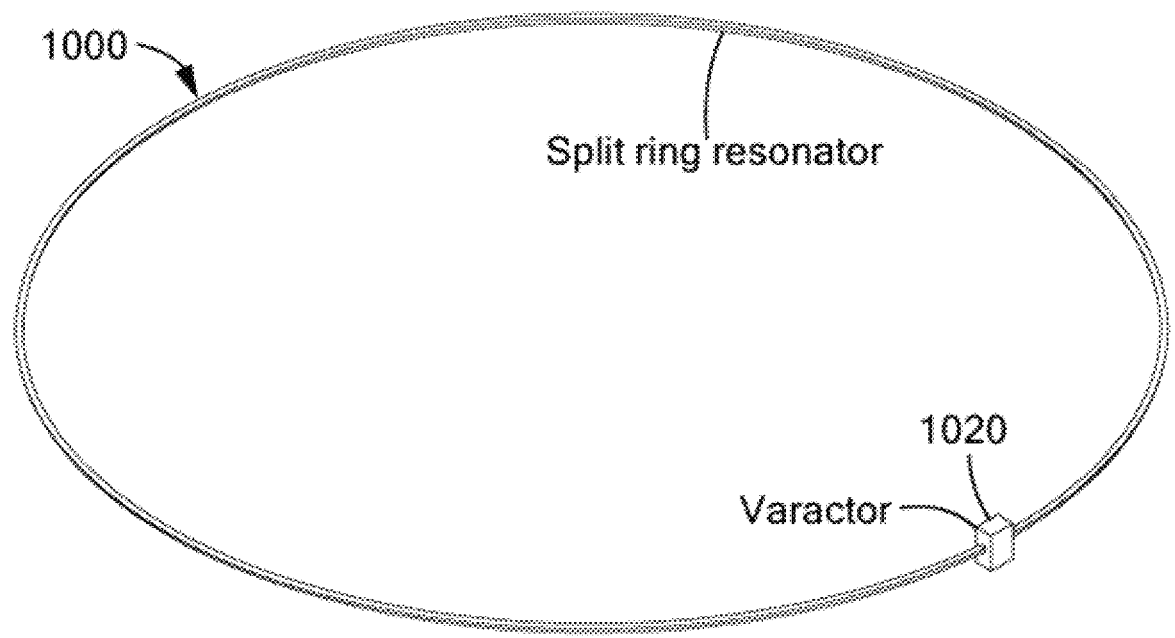

In contradistinction to the response of the linear metamaterials described above (e.g., arrays 300), in cases in which there is an existing nonlinear component 1000 within a resonator 1100, such as a varactor in a split-ring resonator (SRR, as shown in FIG. 12C), the response of the resonator 1100 is dependent upon the excitation strength. In the case of a varactor-loaded split ring resonator 1000 (VLSRR), its resonance frequency varies as a function of the oscillation strength in the resonator 1000. When the oscillation strength in the split ring resonator 1000 is relatively low, the varactor 1020 maintains its original capacitance. However, when the oscillation strength in the in the split ring resonator 1000 is higher (i.e., relatively high), the rectifying effect in the varactor 1020 acts as driving voltage to the varactor 1020 and increases its capacitance, which in turn decreases the resonance frequency of the in the split ring resonator 1000. The excitation power-dependent response of the in the split ring resonator 1000 is modeled by the following formula (Equation 2):

$$\frac{da_2}{dt} = \left[ j(\omega_{o2} - \lambda_0 |a_2|) - \frac{1}{\tau_{e2}} - \frac{1}{\tau_{02}} \right] a_2 + \sqrt{\frac{2}{\tau_{e2}}} s_+$$

where $a_2$ is the mode amplitude of the in the split ring resonator 1000, $\omega_{o2}$ is the original resonance frequency of the in the split ring resonator 1000, $1/\tau_{e2}$ and $1/\tau_{02}$ are the decay rates due to radiation and ohmic loss, respectively, and $\lambda_0$ is the nonlinear coefficient determined by the properties of the varactor 1020.

Figure 12D:
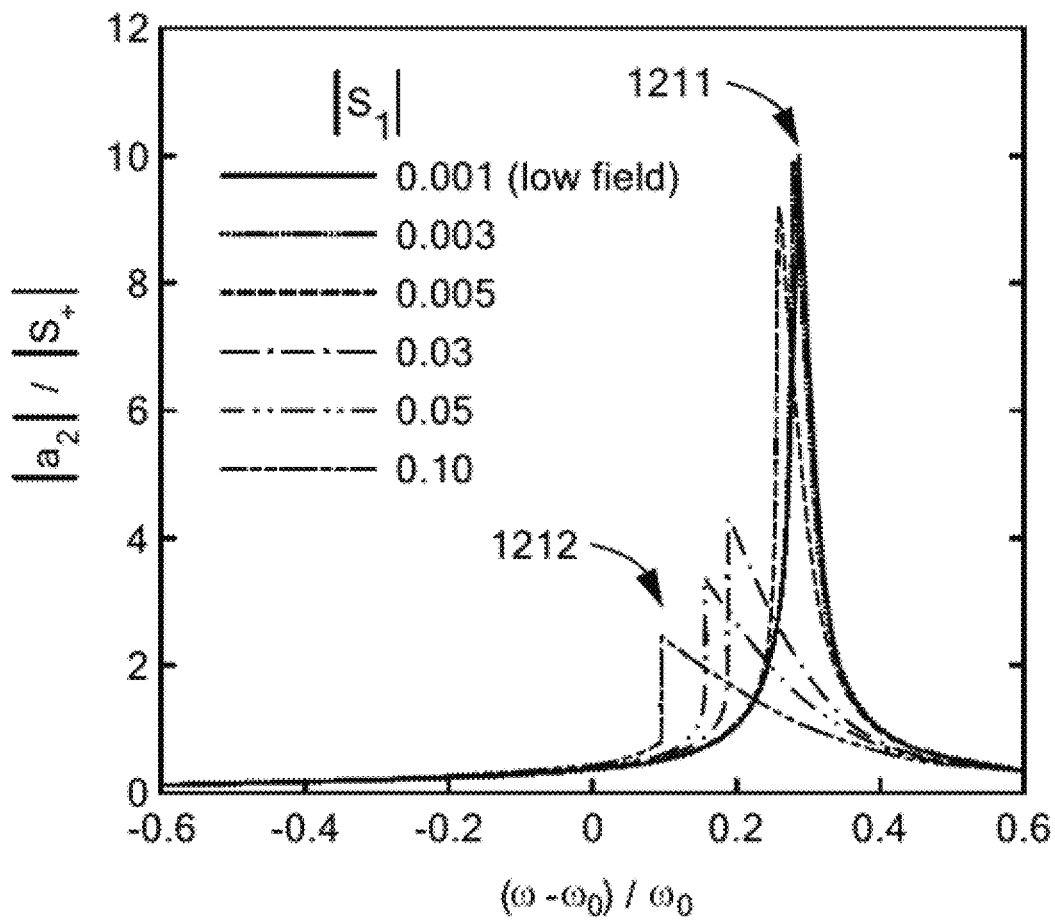

When the excitation strength is low (e.g. $|s_+|=0.001$), the split ring resonator 1000 behaves in a linear fashion with its peak amplitude (1211) at the designated resonance frequency ($\omega_{o2}$), as shown in FIG. 12D. As the excitation strength increases, the resonance frequency of the VLSRR shifts to lower frequencies (1212). When the excitation strength is sufficiently high, the split ring resonator 1000 displays an abrupt transition in the spectrum as the frequency increases. This is due to the bi-stable nonlinear behavior in the amplitude response of the split ring resonator 1000. Along with the frequency shift, the peak oscillation amplitude in the resonator decreases.

Figure 12E:
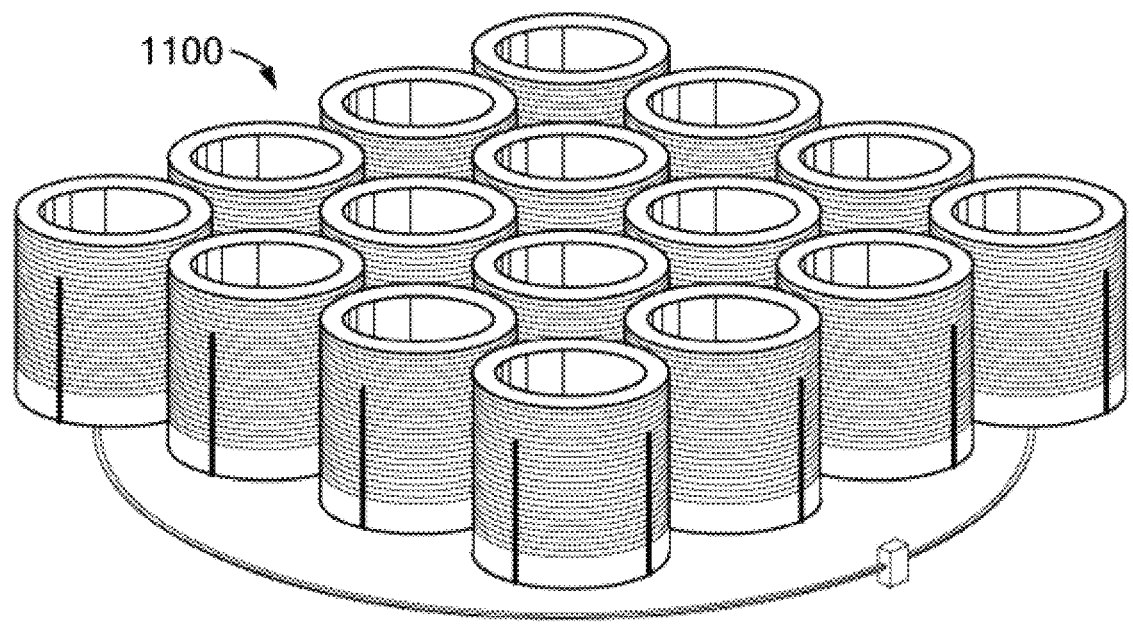

When a controllable array 1100 is composed of a helical resonator array 300 and a split ring resonator 1000, which are proximate to one another, a nonlinear metamaterial (NLMM) is formed, as shown in the embodiment of FIG. 12E. A coupling factor (k) is introduced into the system to describe the interaction between the resonator array 300 and the split ring resonator 1000 as follows (Equation 3):

$$\begin{bmatrix} \frac{da_1}{dt} \\ \frac{da_2}{dt} \end{bmatrix} = \begin{bmatrix} j\omega_{o1} - \frac{1}{\tau_{e1}} - \frac{1}{\tau_{ol}} & jk \\ jk & j[(1+\Delta\omega)\omega_{o1} - \lambda_0|a_2|] - \frac{1}{\tau_{e2}} - \frac{1}{\tau_{02}} \end{bmatrix}$$

$$\begin{bmatrix} a_1 \\ a_2 \end{bmatrix} + \begin{bmatrix} \sqrt{\frac{2}{\tau_{e1}}} \\ \sqrt{\frac{2}{\tau_{e2}}} \end{bmatrix} s_+$$

Figure 12F:
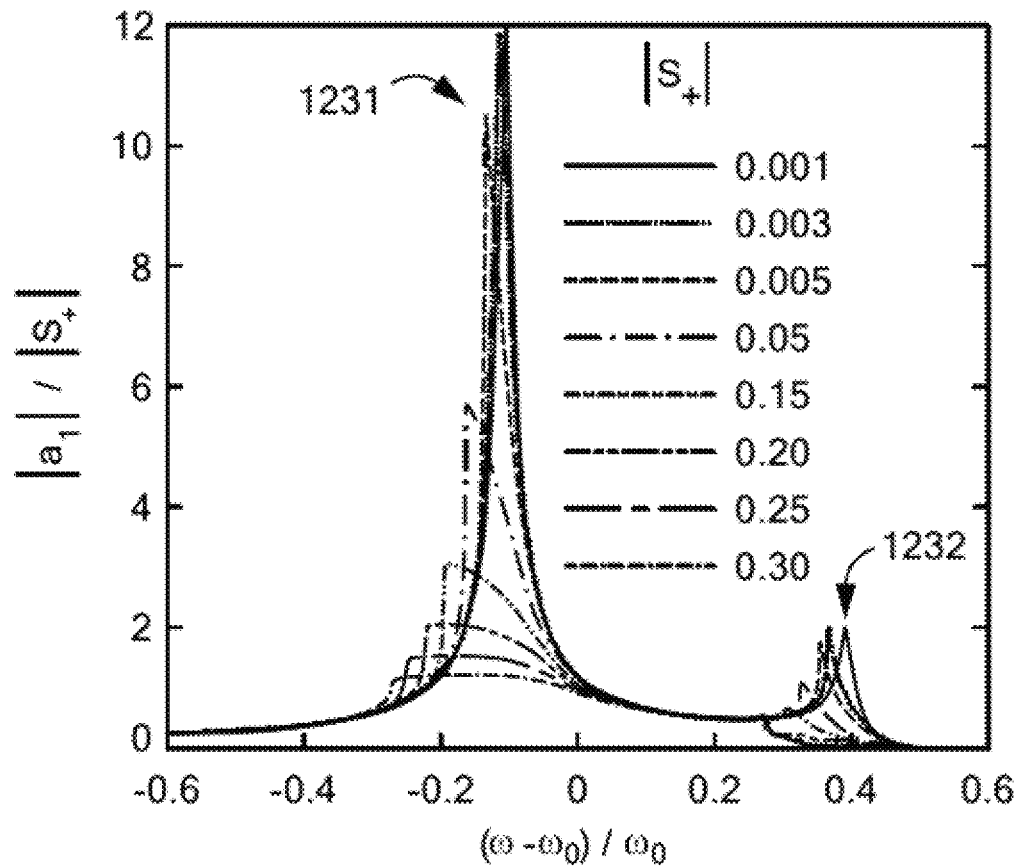

In this system 1100, two parameters, $\Delta\omega$ and k, are variables, while all other parameters may be determined by the material properties and structural design. The illustrative embodiment of FIG. 12E has a coupling factor of k=0.2, which indicates a moderate degree of coupling between the helical resonator array 300 and the split ring resonator 1000, and $\Delta\omega=0.3$ as an arbitrary resonance frequency difference. The calculated oscillation mode amplitudes for different excitation strengths are shown in FIG. 12F. Due to the coupling effect between the helical resonator array 300 and the split ring resonator 1000, two resonance peaks (1231; 1232) appear in the spectra of the low excitation condition. In the first mode, the resonance of the helical resonator array 300 and the split ring resonator 1000 are in phase, while they are out of phase in the second mode. Qualitatively, the strong oscillation amplitude in the first mode (peak 1231) yields a strong magnetic field enhancement in the vicinity of the controllable array 1100 when the excitation is low. As the excitation power increases, both resonance modes shift to lower frequencies and a bi-stable response appears when the excitation surpasses a critical excitation strength. The peak oscillation amplitude decreases dramatically (peak 1232), which yields a decrease in the magnetic field enhancement.

Figure 13:
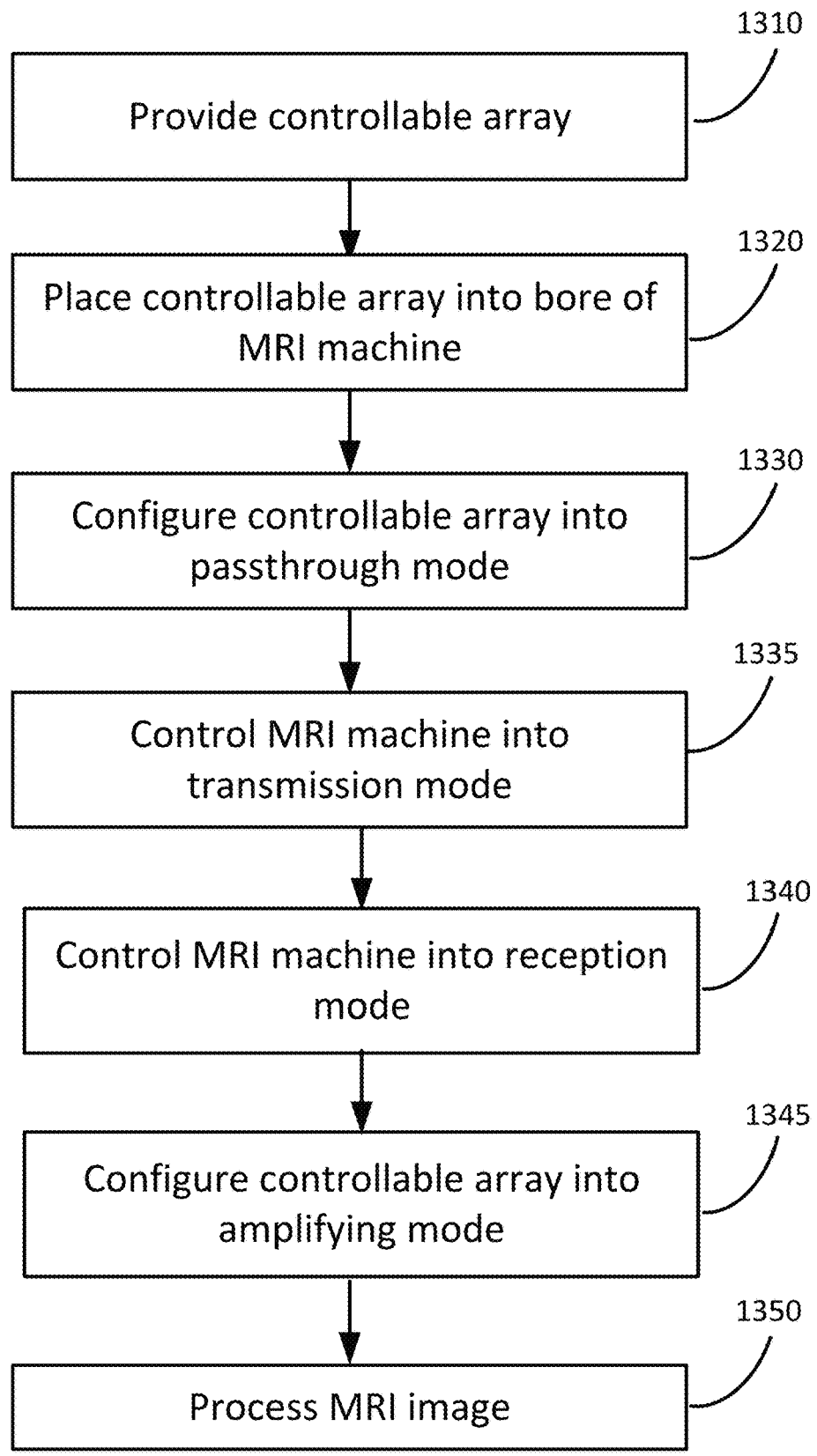
FIG. 13 is a flow chart illustrating an embodiment of operating a controllable array assembly.

FIG. 13 is a flowchart that illustrates operation of embodiments of the controllable array assembly 1100.

At step 1310, the method includes providing a controllable array assembly 1100. Illustrative embodiments of the controllable array assembly 1100 include a resonator array 300 configured to amplify signals the working frequency of an MRI machine 100, but for a coupling to the resonator array 300 of a control resonator 1000 in a first mode, as described below.

At step 1320, the method includes placing the controllable array assembly 1100 into the bore 102 of an MRI machine 100, if it is not already that location. In preferred embodiments, the controllable array assembly 1100 is placed in the bore 102 of the MRI machine 100 along with a specimen 99 to be imaged by the MRI machine 100.

Step 1330 includes configuring the controllable array assembly 1100 into a first mode (or "passthrough" mode), in which passthrough mode the controllable array assembly 1100 does not substantially amplify the excitation signal provided to the specimen 99 by the MRI machine 100.

To that end, step 1330 includes configuring the control coupler 1020 into a first impedance state (Z1), so as to configure the control resonator 1000 into a first resonance state. The control resonator 1000 couples to the resonator array 300 (e.g., to each resonator in the resonator array 300), to establish a passthrough resonance frequency (F1) for the controllable array assembly 1100. In this passthrough mode, the resonance frequency (F1) for the controllable array assembly 1100 is offset from (either greater than or less than) the working frequency ($\omega$) of the MRI machine 100, resulting in small amplification of a stimulus signal provided by body coils 120 of the MRI machine 100 to the specimen 99. In the passthrough mode, the resonator array 300 amplifies a stimulus signal, provided by body coils 120 of the MRI machine 100 to the specimen 99, less than it does in the amplifying mode, described below.

Step 1335 includes controlling the MRI machine 100 into the transmission mode, and providing an excitation signal from the MRI machine 100 to the specimen 99.

Step 1340 includes controlling the MRI machine 100 into the reception mode, and capturing with the MRI machine 100 the response signal generated by the specimen 99. In preferred embodiments, step 1345 is performed only after the MRI machine 100 transitions to reception mode.

Step 1345 includes configuring the controllable array assembly 1100 into a second mode (or "amplifying" mode), in which the controllable 1000 substantially amplifies the signal produced by the specimen and provided by the specimen to the MRI machine 100. In preferred embodiments, the step 1345 of configuring the controllable array assembly 1100 into the amplifying mode is not done when the MRI machine 100 is in transmitting mode.

To that end, step 1345 includes configuring the control coupler 1020 into a second impedance state (Z2), so as to configure the control resonator 1000 into a second resonance state. In this state, the control resonator 1000 couples to the resonator array 300 (e.g., to each resonator in the resonator array 300), to establish an amplifying resonance frequency for the controllable array assembly 1100. In this amplifying mode, the resonance frequency (F2) for the controllable array assembly 1100 is substantially equal to the frequency of response signals produced by the specimen 99 and received by the body coils 120 (and/or patient coils 130), so that the resonator array 300 amplifies the signals produced by the specimen 99 in the ways described above for arrays 300. In the amplifying mode, the resonator array 300 amplifies a stimulus signal, provided by body coils 120 of the MRI machine 100 to the specimen 99, more than it does in the passthrough mode, described above.

The following table summarizes the foregoing modes, for an MRI machine 100 having a working frequency "$\omega$."

| Mode | Control coupler 1020 impedance | Control Resonator 1000 resonant frequency | Controllable array assembly 1100 resonant frequency |
|---|---|---|---|
| Passthrough | Z1 | F1 | $\omega$ + or − offset |

-continued

| Mode | Control coupler 1020 impedance | Control Resonator 1000 resonant frequency | Controllable array assembly 1100 resonant frequency |
|---|---|---|---|
| Amplifying | Z2 | F2 | ω |

Step 1350 includes processing the signals received by the MRI machine 100 from the specimen, in response the excitation signal provided by the MRI machine 100 to the specimen.

The foregoing describes a signal magnifying accessory 1100 for use within a bore 102 of an MRI machine 100, the MRI machine having a transmitting coil 120 disposed to transmit, to a specimen 99 in the bore 102, an excitation signal having a transmission frequency in a transmitting mode, and reception coil (120 and/or 130) disposed to receive, from the specimen 99, a response signal having a response frequency in a receiving mode. The accessory 1100 includes a resonator array 300 having a plurality of metamaterial resonators, each of the metamaterial resonators having a resonant frequency, the metamaterial resonators disposed to inductively couple to one another in response to an applied electromagnetic signal.

The accessory 1100 also includes a non-linear control resonator 1000 having (i) a resonator coil 1010, and (ii) a controllable impedance 1020 coupled to the resonator coil. The control resonator 1000 has a first resonant frequency when the controllable impedance 1020 is in a first impedance state, and a second resonant frequency when the controllable impedance 1020 is in a second impedance state.

Illustrative embodiments of the accessory 1100 also have a spacer layer 1110 disposed between the array of resonators 300 and the control resonator 1000, the spacer layer 1100 defining a gap (d) 1111 between the array of resonators 300 and the non-linear control resonator 1000. The resonator coil 1000 and the controllable impedance 1020 are selected so that the control resonator 1000 is configured (i) to produce, in concert with the resonator array 300 when the MRI machine 100 is in the transmitting mode, a first array resonant frequency offset from the transmission frequency of the MRI machine 100; and (ii) to produce, in concert with the resonator array 300 when the MRI machine 100 is in a receiving mode, a second array resonant frequency equal to the response frequency, so as to magnify the response signal.

Isolator

Figure 14A:
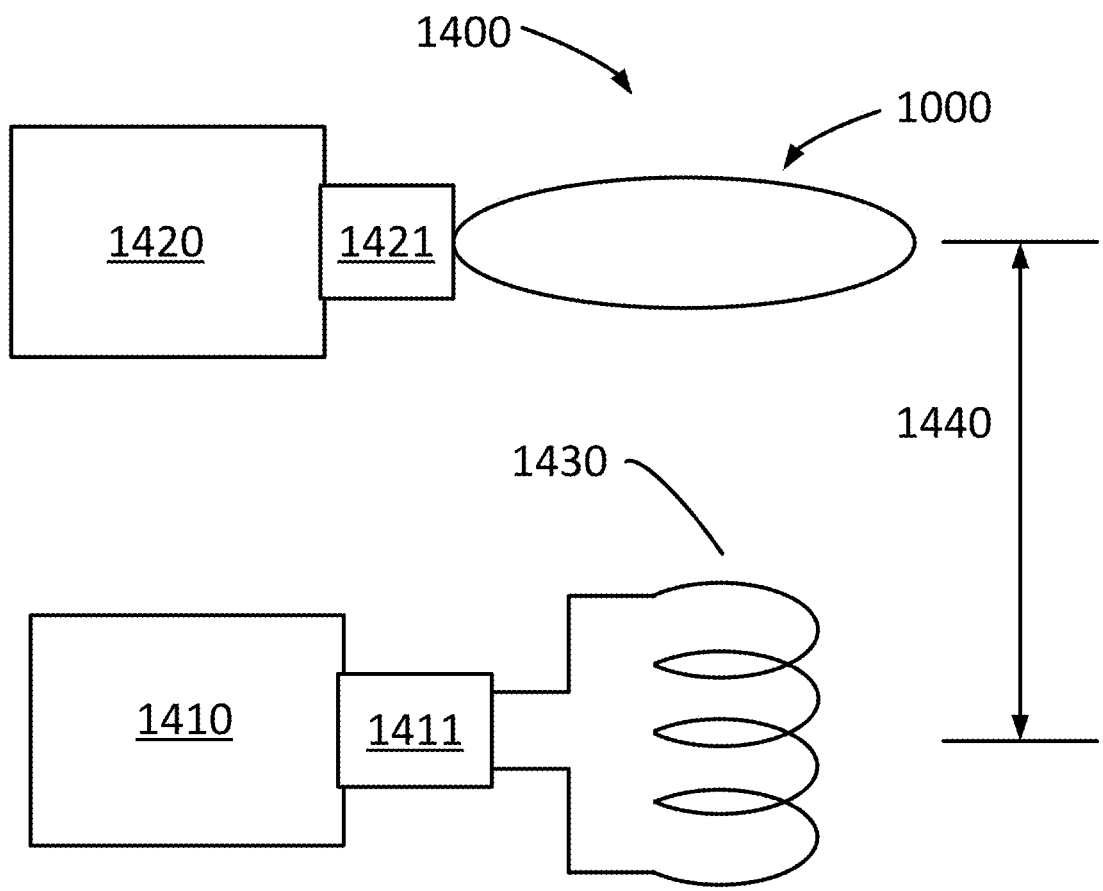
FIG. 14A schematically illustrates an embodiment of an isolator system.
Figure 14B:
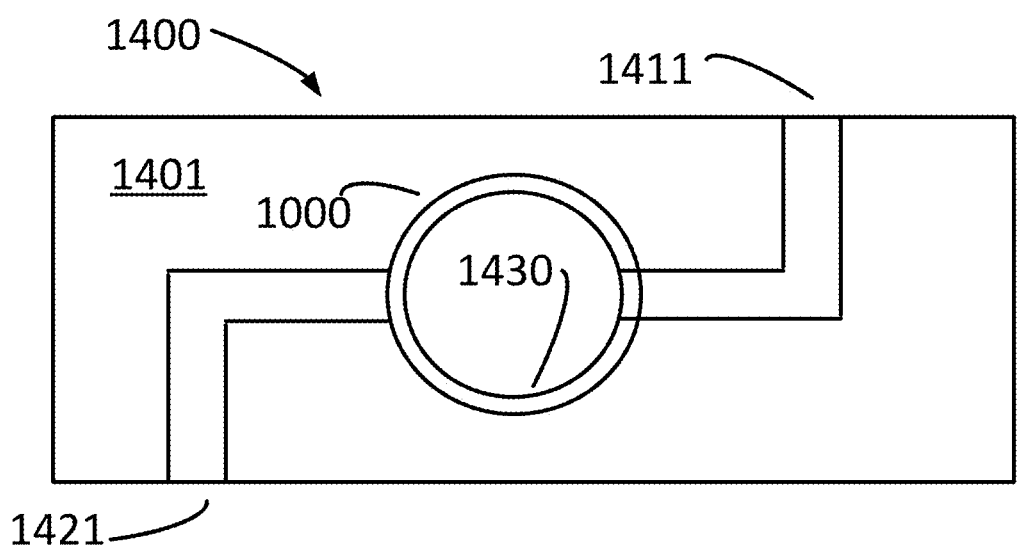
FIG. 14B schematically illustrates an embodiment of an isolator system on an integrated circuit.

FIG. 14A schematically illustrates an embodiment of a controllable isolator assembly 1400. FIG. 14B schematically illustrates an embodiment of a controllable isolator assembly 1400 on an integrated circuit 1401.

The controllable isolator assembly 1400 operates based on the nonlinear effect in strongly coupled resonators, which provide stark contrast between the forward and backward propagating RF signals. Illustrative embodiments include two resonators 1000, 1430 between two ports 1421, 1411, one of which (1000) is loaded with a varactor (e.g., 1020) that enables the nonlinear response. The varactor 1020 can be designed to be turned on and off automatically by the power accepted by the resonator 1000. For example, the resonator can be turned "off" for the signal from port 1421 to port 1411, prohibiting the transmission, while the resonator 1000 can be turned "on" for the signal from port 1411 to port 1421.

In illustrative embodiments, when the RF signal is incident from port 1421, the electric field across the varactor 1020 in the nonlinear resonator 1000 is high, which shifts the resonance frequency of the nonlinear resonator 1000 and decreases the resonance amplitude in the nonlinear resonator 1000. This will induce weak transmission of the signal from port 1421 to port 1411. However, when the RF signal is from port 1411, strong resonance is induced in the linear resonator 1430, but the resonance in the nonlinear resonator 1000 is relatively smaller, which cannot change the resonance frequency of the nonlinear resonator 1000. The transmission from port 1411 port 1421 is high in this condition.

Consequently, the controllable isolator assembly 1400 allows transmission of a first signal across a gap 1440 from a first resonator 1430 to a nonlinear resonator 1000, but suppresses or prohibits transmission of a second signal in the opposite direction—i.e., across the gap 1440 from the nonlinear resonator 1000 to the first resonator 1430.

To those ends, the first resonator 1430 has a characteristic resonance frequency (Fc). The first resonator 1430 in some embodiments is a linear resonator, such as a metamaterial resonator, to name but one example.

The nonlinear resonator 1000 is controllably configurable into a first resonance state in which the nonlinear resonator 1000 has a first resonant frequency (F1) equal to the characteristic resonant frequency of the first resonator 1430 (Fc=F1), and a second resonance state in which the nonlinear resonator 1000 has a second resonant frequency (F2) distinct from the first resonant frequency. For example, the nonlinear resonator 1000 has the first resonance frequency (F1) when its control coupler 1020 is in a first impedance state (Z1), and has the second resonance frequency (F2) when its control coupler 1020 is in a second impedance state (Z2).

When a signal having a frequency (e.g., a center frequency of carrier frequency) equal to the characteristic resonance frequency (Fc) is provided to the first resonator 1430, the first resonator 1430 resonates, and inductively induces a copy of the signal on the nonlinear resonator 1000. In illustrative embodiments, the signal on the first resonator 1430 is not strong enough to induce, across the isolator gap 1440, a change of impedance state in the control coupler 1020.

In contrast, when such a signal is provided to the nonlinear resonator 1000, the power in that signal impinges on the control coupler 1020 and causes the impedance of the control coupler 1020 to change to the second impedance state (Z2), thereby configuring the nonlinear resonator 1000 into a mode in which the nonlinear resonator has the second resonance frequency (F2). Because the second resonance frequency (F2) is not the same as the characteristic frequency (Fc) of the first resonator 1430 (or is at least further from the characteristic frequency (Fc) than is the first resonance frequency (F1)), the inductive coupling of the signal from the first resonator 1430 to the nonlinear resonator is dampened, relative to the inductive coupling from the nonlinear resonator 1000 to the first resonator 1430 as described above.

It should be noted that, although the nonlinear resonator 1000 and the linear resonator 1430 in FIG. 14A and FIG. 14B are represented as single devices, the embodiments are not limited to such single devices. For example, in illustrative embodiments, the nonlinear resonator 1000 may be a set of one or more nonlinear resonators, and/or the linear resonator 1430 may be a set of one or more linear resonators.

Figure 15:
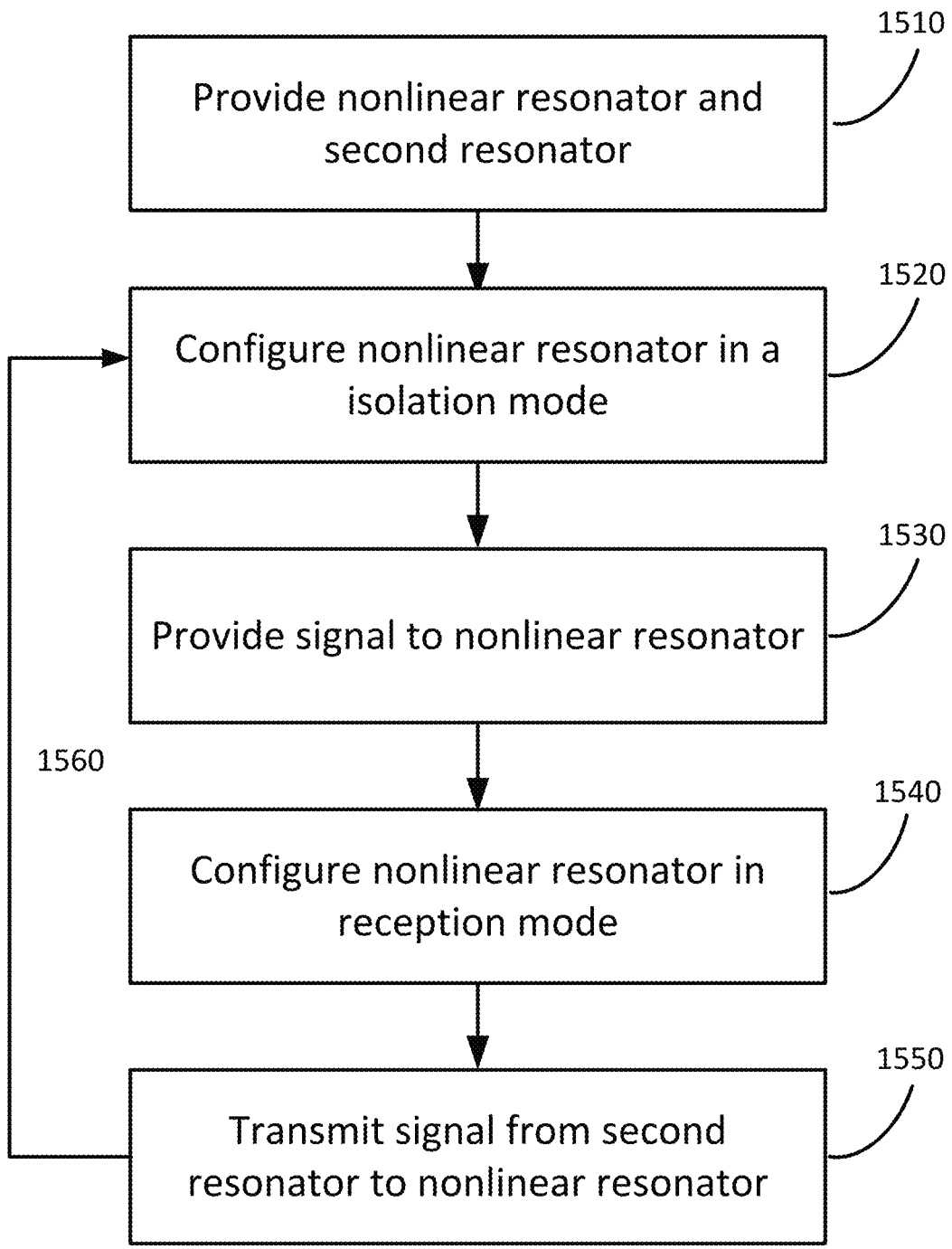
FIG. 15 is a flow chart illustrating an embodiment of operating an isolator.

FIG. 15 is a flow chart describing a method of operating an isolator 1400. The method includes, at step 1510, providing a nonlinear resonator 1000 and a second resonator 1430, as schematically illustrated in FIG. 14A and/or FIG.

14B, above. The second resonator 1430 has a characteristic resonant frequency. The nonlinear resonator has an isolation resonant frequency different from the characteristic resonant frequency, and a transmission resonant frequency equal to the characteristic resonant frequency. Step 1510 may include coupling the nonlinear resonator 1000 to a first port 1421, such a port 1421 coupled to a signal source, network or transceiver 1420.

Step 1520 includes configuring the nonlinear resonator 1000 into an isolation configuration (so that the isolator 1400 is in an "isolation mode,") in which the nonlinear resonator 1000 has the isolation resonant frequency. In the isolation configuration (and mode), the resonant coupling between the nonlinear resonator 1000 and the second resonator 1430 is weak (at least weaker than in the transmission mode described below), such that a signal provided to the nonlinear resonator 1000 at step 1530, for example by first port 1421, couples weakly if at all to the second resonator 1430.

At step 1540, the method configures the nonlinear resonator 1000 into transmission configuration (so that the isolator 1400 is in a "transmission mode"). In the transmission configuration (and mode), the nonlinear resonator 1000 has the transmission resonant frequency, and may be described as being in a "reception configuration"). In this configuration (and mode), the resonant coupling between the nonlinear resonator 1000 and the second resonator 1430 is strong (at least stronger than in the isolation mode described above), such that a signal provided to the nonlinear resonator 1000 at step 1550, for example by second port 1411, couples well to the nonlinear resonator 1000.

For example, in one embodiment the inventors evaluated transmission of a 300 MHz signal provided at −5 dBm. When the signal was provided to port 1421, transmission of the signal from port 1421 to port 1411 was weak because the nonlinear resonator 1000 was in the isolation configuration. In contrast, when the signal was provided to port 1411 and the nonlinear resonator 1000 was in the transmission configuration (or reception configuration), transmission of the signal from port 1411 to port 1421 was higher. The inventors found that the contrast in these two transmissions was 15 dB. In other words, transmission from port 1411 to port 1421 was 15 dB greater than transmission from port 1421 to port 1411. In other embodiments, the isolator 1400 may be configured (e.g., by specification and selection of the dimensions of the components; the gap 1440) to produce a contrast in transmission of at least 3 dB, 6 dB, 9 dB, or 12 dB, to name but a few examples. According to the foregoing illustrative embodiments, a nonlinear resonator 1000 and a linear resonator 1430 may be considered to be substantially isolated from one another if the contrast in transmission between them in an isolation mode and a transmission mode is at least 3 dB, 6 dB, 9 dB, 12 dB or 15 dB. A person of ordinary skill in the art, in possession of this specification, may specify the ratio that defines substantial isolation based, for example, on the needs for which an isolator 1400 is to be implemented.

Some embodiments of the method then configures the nonlinear isolator 1400 back into the isolation configuration (and mode), at step 1560.

As described, some embodiments include a circuit having a first resonator having a characteristic resonant frequency; and a non-linear resonator controllably configurable into a first resonance state in which the non-linear resonator has a first resonant frequency equal to the characteristic resonant frequency, and a second resonance state in which the non-linear resonator has a second resonant frequency distinct from the first resonant frequency. In illustrative embodiments, the first resonator is configured to couple to a first port and the non-linear resonator is configured to couple to a second port, and wherein in the first resonance state, the non-linear resonator is configured to inductively couple to the first resonator so as to communicatively couple a signal from the first resonator to the second port, and in the second resonance state, the non-linear resonator is configured to isolate the second port from the first resonator.

The following is a list of reference numbers used herein.
- 99: Specimen;
- 100: MRI machine in cross-section;
- 101: Table;
- 102: Bore of MRI machine;
- 110: Main field coils;
- 111: Shim coil;
- 115: Gradient coil;
- 120: Body coils;
- 130: Specimen coils;
- 140: MRI machine controller;
- 150: Computer;
- 151: Computer communications link;
- 300: Resonator array;
- 301: Unit cell;
- 302: Top of unit cell;
- 303: Middle of unit cell;
- 310: X-Pitch;
- 311: Y-Pitch;
- 400: Response of a resonator;
- 401: Center frequency;
- 402: Upper 3 dB point;
- 403: Lower 3 dB point;
- 405: Noise level;
- 410: Frequency delta;
- 450: Frequency below working frequency of MRI machine;
- 452: Working frequency of MRI machine;
- 454: Frequency above working frequency of MRI machine;
- 460: Resonance response of array tuned to frequency below working frequency of MRI machine;
- 461: Resonant frequency of array tuned to frequency below working frequency of MRI machine;
- 462: Resonance response of array tuned to working frequency of MRI machine;
- 463: Resonant frequency of array tuned to working frequency of MRI machine;
- 464: Resonance response of array tuned to frequency above working frequency of MRI machine;
- 465: Resonant frequency of array tuned to frequency above working frequency of MRI machine;
- 500: Helical resonator;
- 501: Top end of resonator;
- 502: Bottom end of resonator;
- 503: Interior of resonator;
- 510: Conductor;
- 511: End of conductor;
- 512: Electrically insulating covering;
- 513: Turn;
- 515: Conductor gap;
- 520: Core;
- 521: Core outside diameter;
- 522: Core inside diameter;
- 523: Outer surface of core;
- 525: Core height;
- 530: Groove;
- 550: Additional reactance;

560: Dish;
561: Coupling loop;
565: Water;
566: Surface of water;
567: Dry resonant frequency;
568: 10% water resonant frequency;
569: 20% water resonant frequency;
600: BC-SRR resonator;
601: Top surface of BC-SRR;
602: Bottom surface of BC-SRR;
610: First split-ring resonator;
611: First gap;
612-613: Opposing ends of first gap;
620: Second split-ring resonator;
621: Second gap;
650: High-permittivity substrate;
700: Flexible substrate;
799: Limb of specimen;
801: Coupler;
802: Interior of helical coil;
810: Semiconductor patch;
820: Switch;
1000: Non-linear resonator;
1010: Non-linear resonator loop;
1011, 1012: Ends of non-linear resonator loop;
1013: Gap;
1020: Non-linear resonator control coupler;
1100: Controllable array assembly;
1110: Spacer;
1111: Spacer Gap;
1400: Isolator system;
1401: Integrated circuit;
1410: First transceiver or network;
1411: First port;
1420: Second transceiver or network;
1421: Second port;
1430: Linear metamaterial resonator;
1440: Transmission gap.

Various embodiments may be characterized by the potential claims listed in the paragraphs following this paragraph (and before the actual claims provided at the end of this application). These potential claims form a part of the written description of this application. Accordingly, subject matter of the following potential claims may be presented as actual claims in later proceedings involving this application or any application claiming priority based on this application. Inclusion of such potential claims should not be construed to mean that the actual claims do not cover the subject matter of the potential claims. Thus, a decision to not present these potential claims in later proceedings should not be construed as a donation of the subject matter to the public.

Without limitation, potential subject matter that may be claimed (prefaced with the letter "P" so as to avoid confusion with the actual claims presented below) includes:

P1. A circuit comprising: first resonating means for resonating in response to an applied electromagnetic signal, the first resonating means having a characteristic resonant frequency; and a non-linear resonating means for selectively communicating in resonance with the first resonating means, the non-linear resonating means configurable into a first resonance state having a first resonant frequency equal to the characteristic resonant frequency, and a second resonance state having a second resonant frequency distinct from the first resonant frequency.

P2. A circuit according to P1, wherein when the non-linear resonating means is in the second resonance state, the non-linear resonating means is substantially communicatively isolated from the first resonating means.

P3. A signal magnifying accessory for use within a bore of an MRI machine, the MRI machine having a body coil disposed to transmit, to a specimen in the bore, an excitation signal having a transmission frequency in a transmitting mode, and to receive, from the specimen, a response signal having a response frequency in a receiving mode, the accessory comprising: a resonator array comprising a plurality of metamaterial resonators, each of the metamaterial resonators having a resonant frequency, the metamaterial resonators disposed to inductively couple to one another in response to an applied electromagnetic signal; a non-linear control means configured (i) to produce, in concert with the resonator array when the MRI machine is in the transmitting mode, a first array resonant frequency offset from the transmission frequency; and (ii) to produce, in concert with the resonator array when the MRI machine is in a receiving mode, a second array resonant frequency equal to the response frequency, so as to magnify the response signal.

P4. The signal magnifying accessory according to P3, wherein the plurality of metamaterial resonators comprises a plurality of helical coil resonators.

P5. The signal magnifying accessory according to P3, wherein the plurality of metamaterial resonators comprises a plurality of split-ring resonators.

P6. The signal magnifying accessory according to P3, wherein the plurality of metamaterial resonators comprises a plurality of broadside-coupled split-ring resonators.

P7. The signal magnifying accessory according to P3, wherein the non-linear control means comprises a split-ring resonator defining a gap, and a varactor electrically coupled within the gap.

The embodiments of the inventions described above are intended to be merely exemplary; numerous variations and modifications will be apparent to those skilled in the art. All such variations and modifications are intended to be within the scope of the present invention as defined in any appended claims.

What is claimed is:

1. A circuit comprising:
   a first resonator having a characteristic resonant frequency; and
   a non-linear resonator controllably configurable into a first resonance state in which the non-linear resonator has a first resonant frequency equal to the characteristic resonant frequency, and a second resonance state in which the non-linear resonator has a second resonant frequency distinct from the first resonant frequency;
   wherein the first resonator and the non-linear resonator are substantially isolated from one another in the isolation mode when the non-linear resonator is configured in the second resonance state.

2. The circuit of claim 1 wherein:
   the first resonator is configured to couple to a first port and the non-linear resonator is configured to couple to a second port, and wherein:
   in the first resonance state, the non-linear resonator is configured to inductively couple to the first resonator so as to communicatively couple a signal from the first resonator to the second port, and
   in the second resonance state, the non-linear resonator is configured to isolate the second port from the first resonator.

3. The circuit of claim 2 wherein:
   the non-linear resonator comprises a metamaterial resonator having a first end and a second end, and a coupler electrically disposed between the first end and the second end, wherein the coupler is controllably configurable into a plurality of impedance states, including:
- a first impedance state, which first impedance state configures the non-linear resonator into the first resonance state, and
- a second impedance state, which second impedance state configures the non-linear resonator into the second resonance state.

4. The circuit of claim 3 wherein the metamaterial resonator comprises a split-ring resonator.

5. The circuit of claim 3, wherein the coupler comprises a varactor, the varactor configured:
   (a) to have the second impedance state in response to a radio-frequency signal incident on the coupler from the second port, such that the non-linear resonator is in the second resonant state and the second port is isolated from the first resonator, and
   (b) to have the first impedance state in the absence of such radio-frequency signal at the carrier frequency from the second port, such that the non-linear resonator is in the first resonant state and is configured to communicatively couple the first resonator to the second port.

6. The circuit of claim 3, wherein the coupler comprises a varactor, the varactor configured:
   (a) to have the first impedance state in response to a radio-frequency signal incident on the coupler from the second port, such that the non-linear resonator is in the first resonant state and is configured to communicatively couple the second port to the first resonator, and
   (b) to have the second impedance state in the absence of such radio-frequency signal at the carrier frequency from the second port, such that the non-linear resonator is in the second resonant state and the second port is isolated from the first resonator.

7. The circuit of claim 3, wherein the coupler comprises a switch.

8. The circuit of claim 7, wherein the switch comprises a transistor.

9. The circuit of claim 2, wherein the first resonator is a linear resonator.

10. The circuit of claim 9, wherein the linear resonator is helix resonator.

* * * * *